United States Patent
Mikule et al.

(10) Patent No.: US 11,801,240 B2
(45) Date of Patent: Oct. 31, 2023

(54) COMBINATION THERAPIES AND USES THEREOF

(71) Applicant: Tesaro, Inc., Waltham, MA (US)

(72) Inventors: Keith W. Mikule, Boylston, MA (US); Zebin Wang, Wellesley, MA (US); Yinghui Zhou, Belmont, MA (US)

(73) Assignee: Tesaro, Inc., Wilmington, DE (US)

( * ) Notice: Subject to any disclaimer, the term of this patent is extended or adjusted under 35 U.S.C. 154(b) by 359 days.

(21) Appl. No.: 16/754,083

(22) PCT Filed: Oct. 5, 2018

(86) PCT No.: PCT/US2018/054606
§ 371 (c)(1),
(2) Date: Apr. 6, 2020

(87) PCT Pub. No.: WO2019/071123
PCT Pub. Date: Apr. 11, 2019

(65) Prior Publication Data
US 2020/0306236 A1  Oct. 1, 2020

Related U.S. Application Data
(60) Provisional application No. 62/569,239, filed on Oct. 6, 2017.

(51) Int. Cl.
| | |
|---|---|
| A61K 31/454 | (2006.01) |
| A61K 31/517 | (2006.01) |
| A61P 35/00 | (2006.01) |
| C07K 16/22 | (2006.01) |
| C07K 16/28 | (2006.01) |
| A61K 9/20 | (2006.01) |
| A61K 9/48 | (2006.01) |
| A61K 45/06 | (2006.01) |

(52) U.S. Cl.
CPC ............ *A61K 31/454* (2013.01); *C07K 16/22* (2013.01); *C07K 16/2863* (2013.01); *A61K 9/20* (2013.01); *A61K 9/48* (2013.01); *A61K 45/06* (2013.01)

(58) Field of Classification Search
CPC ...... A61K 31/454; A61K 31/517; A61P 35/00
USPC .............................................. 514/266.1, 322
See application file for complete search history.

(56) References Cited

U.S. PATENT DOCUMENTS

| | | |
|---|---|---|
| 7,595,048 B2 | 9/2009 | Honjo et al. |
| 8,071,623 B2 | 12/2011 | Jones et al. |
| 8,217,149 B2 | 7/2012 | Irving et al. |
| 8,436,185 B2 | 5/2013 | Foley et al. |
| 8,728,474 B2 | 5/2014 | Honjo et al. |
| 8,779,108 B2 | 7/2014 | Queva et al. |
| 8,952,136 B2 | 2/2015 | Carven et al. |
| 9,624,298 B2 | 4/2017 | Nastri et al. |
| 9,707,302 B2 | 7/2017 | Goldenberg et al. |
| 9,815,897 B2 | 11/2017 | King et al. |
| 10,738,117 B2 | 8/2020 | King et al. |
| 2009/0123419 A1 | 5/2009 | Sherman et al. |
| 2010/0003192 A1 | 1/2010 | Sherman et al. |
| 2012/0207856 A1 | 8/2012 | Ajay et al. |
| 2012/0269861 A1 | 10/2012 | Sherman et al. |
| 2015/0071910 A1 | 3/2015 | Kowanetz et al. |
| 2015/0344968 A1 | 12/2015 | Johnson |
| 2016/0075783 A1 | 3/2016 | King et al. |
| 2016/0296633 A1 | 10/2016 | Goldenberg et al. |
| 2016/0340428 A1 | 11/2016 | Yang |
| 2017/0000885 A1 | 1/2017 | Rhee et al. |
| 2017/0049767 A1 | 2/2017 | Blanchette et al. |
| 2018/0311224 A1 | 11/2018 | Hedley et al. |
| 2020/0016142 A1 | 1/2020 | McGurk et al. |
| 2020/0017462 A1 | 1/2020 | Wu et al. |
| 2020/0055837 A1 | 2/2020 | Stewart et al. |
| 2020/0289493 A1 | 9/2020 | Bobilev et al. |
| 2020/0299387 A1 | 9/2020 | Mikule |
| 2021/0008053 A1 | 1/2021 | Sun et al. |
| 2021/0106574 A1 | 4/2021 | Feng et al. |
| 2021/0322415 A1* | 10/2021 | Barry ................. A61K 31/502 |
| 2022/0048983 A1 | 2/2022 | Milenkova-Ilieva et al. |

FOREIGN PATENT DOCUMENTS

| | | |
|---|---|---|
| CN | 110831580 | 2/2020 |
| EA | 201992594 | 3/2020 |
| EP | 0325199 | 10/1993 |
| EP | 0357061 | 6/1994 |

(Continued)

OTHER PUBLICATIONS

ClinicalTrials.gov [online], "Avelumab in Patients With MSS, MSI-H and POLE-mutated Recurrent or Persistent Endometrial Cancer and of Avelumab/Talazoparib and Avelumab/Axitinib in Patients With MSS Recurrent or Persistent Endometrial Cancer", U.S. National Library of Medicine, Sep. 23, 2016, retrieved on Aug. 17, 2021, retrieved from URL <"https://clinicaltrials.gov/ct2/show/NCT02912572">, 13 pages.

ClinicalTrials.gov [online], "History of Changes for Study: NCT02849496: Veliparib and Atezolizumab Either Alone or in Combination in Treating Patients With Stage III-IV Triple Negative Breast Cancer", U.S. National Library of Medicine, Sep. 12, 2016, retrieved on Aug. 17, 2021, retrieved from URL <"https://clinicaltrials.gov/ct2/history/NCT02849496?V_3=View#StudyPageTop">, 11 pages.

Crafton et al., "PARP inhibition and gynecologic malignancies: A review of current literature and on-going trials", Gynecologic Oncology, Jul. 2016, 142(3): 588-596.

Evans et al., "PARP inhibitors in ovarian cancer: evidence, experience and clinical potential" Therapeutic Advances in Medical Oncology, Feb. 2017, 9(4):253-267.

(Continued)

*Primary Examiner* — Raymond J Henley, III
(74) *Attorney, Agent, or Firm* — Fish & Richardson P.C.

(57) ABSTRACT

The present disclosure relates to combination therapies containing one or more PARP inhibitors and one or more angiogenesis inhibitor. Also described herein are therapeutic uses of such combination therapies for treating various disorders and conditions. The combination therapies and uses thereof can be useful for preventing tumor cell growth, preventing tumor metastasis, inducing an immune response or enhancing an immune response.

31 Claims, 13 Drawing Sheets

(56) References Cited

FOREIGN PATENT DOCUMENTS

| | | |
|---|---|---|
| EP | 2007733 | 5/2016 |
| EP | 3621592 | 3/2020 |
| JP | 2011509252 | 3/2011 |
| JP | 2011509253 | 3/2011 |
| JP | 2017504623 | 2/2017 |
| WO | WO 2007/113596 | 10/2007 |
| WO | WO 2008/084261 | 7/2008 |
| WO | WO 2009/064738 | 5/2009 |
| WO | WO 2009/087381 | 7/2009 |
| WO | WO 2010/091140 | 8/2010 |
| WO | WO 2011/153383 | 12/2011 |
| WO | WO 2011/160063 | 12/2011 |
| WO | WO 2012/027224 | 3/2012 |
| WO | WO 2013/182645 | 12/2013 |
| WO | WO 2014/088983 | 6/2014 |
| WO | WO 2014/088984 | 6/2014 |
| WO | WO 2014/138101 | 9/2014 |
| WO | WO 2014/179664 | 11/2014 |
| WO | WO 2015/086473 | 6/2015 |
| WO | WO 2015/108986 | 7/2015 |
| WO | WO 2015/116868 | 8/2015 |
| WO | WO 2015/184145 | 12/2015 |
| WO | WO 2016/094391 | 6/2016 |
| WO | WO 2016/126858 | 8/2016 |
| WO | WO 2016/161270 | 10/2016 |
| WO | WO 2016/200835 | 12/2016 |
| WO | WO 2016/210108 | 12/2016 |
| WO | WO 2017/075091 | 5/2017 |
| WO | WO 2017/142871 | 8/2017 |
| WO | WO 2018/005818 | 1/2018 |
| WO | WO 2018/059437 | 4/2018 |
| WO | WO 2018/085468 | 5/2018 |
| WO | WO 2018/085469 | 5/2018 |
| WO | WO 2018/129553 | 7/2018 |
| WO | WO 2018/129559 | 7/2018 |
| WO | WO 2018/200517 | 11/2018 |
| WO | WO 2018/201096 | 11/2018 |
| WO | WO 2018/208968 | 11/2018 |
| WO | WO 2018/213732 | 11/2018 |
| WO | WO 2019/005762 | 1/2019 |
| WO | WO 2019/067634 | 4/2019 |
| WO | WO 2019/067978 | 4/2019 |
| WO | WO 2019/071123 | 4/2019 |
| WO | WO 2019/133697 | 7/2019 |
| WO | WO 2019/152989 | 8/2019 |

OTHER PUBLICATIONS

Landrum et al., "A phase I trial of pegylated liposomal doxorubicin (PLD), carboplatin, bevacizumab and veliparib in recurrent, platinum-sensitive ovarian, primary peritoneal, and fallopian tube cancer: An NRG Oncology/Gynecologic Oncology Group study", Gynecologic Oncology, Nov. 2015, 140(2):204-209.

Marchetti et al., "Olaparib, PARP1 inhibitor in ovarian cancer", Expert Opinion on Investigational Drugs, Jul. 2012, 21(10): 1575-1584.

McLachlan et al., "The current status of PARP inhibitors in ovarian cancer", Tumori: A Journal of Experimental and Clinical Oncology, Oct. 2016, 102(5): 433-444.

Akbar et al., "A compact vocabulary of paratope-epitope interactions enables predictability of antibody-antigen binding," Cell Reports, Mar. 2021, 34:108856, 21 pages.

Alberts et al., "Analyzing Protein Structure and Function," Molecular Biology of the Cell, 4th edition. New York: Garland Science, 2002, 2 pages.

AlHilli et al., "In vivo anti-tumor activity of the PARP inhibitor niraparib in homologous recombination deficient and proficient ovarian carcinoma," Gynecologic Oncology, 2016, 143: 379-388.

Almagro et al., "Humanization of Antibodies," Frontiers in Bioscience, 2008, 13:1619-1633.

Altshuler et al., "Generation of Recombinant Antibodies and Means for Increasing Their Affinity," Biochemistry (Moscow), 2010, 75(13):1584-1605.

CAS Registry No. 2022215-59-2 Substance Detail, CAS SciFinder, 2016, 5 pages.

ClinicalTrials.gov [online], "History of Changes for Study: NCT02660034: The Safety, Pharmacokinetics and Antitumor Activity of BGB-A317 in Combination With the BGB-290 in Subjects With Advanced Solid Tumors," U.S. National Library of Medicine, Aug. 13, 2017, retrieved from URL <"https://clinicaltrials.govict2/history/NCT02660034?V4=View#StudyPageTop">, 16 pages.

Dedes et al. , "Synthetic lethality of PARP inhibition in cancers lacking BRCA1 and BRCA2 mutations," Cell Cycle, 2011, 10(8): 1192-1199.

Dockery et al. "Rucaparib: the past, present, and future of a newly approved PARP inhibitor for ovarian cancer," OncoTargets and Therapy, 2017, 10: 3029-3037.

Edwards et al., "The Remarkable Flexibility of the Human Antibody Repertoire; Isolation of Over One Thousand Different Antibodies to a Single Protein, BLyS," J. Mol. Biol., 2003, 334:103-118.

Friedlander et al., "A Phase 1/1b Study of the Anti-PD-1 Monoclonal Antibody BGB-A317 (A317) in Combination with the PARP Inhibitor BGB-290 (290) in Advanced Solid Tumors," American Society of Clinical Oncology, Poster Presentation, Jun. 2, 2017, 1 page.

Hasegawa et al., "Single amino acid substitution in LC-CDR1 induces Russell body phenotype that attenuates cellular protein synthesis through eIF2a phosphorylation and thereby downregulates IgG secretion despite operational secretory pathway traffic," mAbs, 2017, 9(5): 854-873.

Konstantinopoulos et al., "Phase I/II study of niraparib plus pembrolizumab in patients with triple-negative breast cancer or recurrent ovarian cancer," Meeting Abstract I 2016 ASCO Annual Meeting, re-printed in Journal of Clinical Oncology, 2016, 34(15), Suppl., 4 pages.

Lippow et al., "Computational design of antibody-affinity improvement beyond in vivo maturation," Nature Biotechnology, 2007, 25(10): 1171-1176.

Lo et al., "Conformational epitope matching and prediction based on protein surface spiral features," BMC Genomics, 2021, 22(Suppl. 2): 116, 16 pages.

Marchalonis et al., "The antibody repertoire in evolution: Chance, selection, and continuity," Developmental & Comparative Immunology, 2006, 30:223-247.

Marks et al., "How repertoire data are changing antibody science," J. Biol. Chem., 2020, 295(29): 9823-9837.

Mendes-Pereira et al., "Synthetic lethal targeting of PTEN mutant cells with PARP inhibitors," EMBO Molecular Medicine, 2009, 1: 315-322.

Sulea et al., "Application of Assisted Design of Antibody and Protein Therapeutics (ADAPT) improves efficacy of a Clostridium difficile toxin A single-domain antibody," Scientific Reports, 2018, 8(260):1-11.

Vajda et al., "Progress toward improved understanding of antibody maturation," Current Opinion in Structural Biology, 2021, 67: 226-231.

Wilcoxen et al., "Homologous recombination deficiency (HRD) score enriches for niraparib sensitive high grade ovarian tumors.," Presented at ASCO, 2015, Abstract #5532, 1 page.

U.S. Appl. No. 62/356,461, filed Jun. 29, 2016, Hedley et al.

U.S. Appl. No. 62/402,427, filed Sep. 30, 2016, Hedley et al.

[No author listed] "Integrated genomic analyses of ovarian carcinoma," Nature, 2011, 474:609-15.

Ascierto et al., "Biomarkers for Immunostimulatory Monoclonal Antibodies in Combination Strategies for Melanoma and Other Tumor Types," Clin. Cancer. Res., 2013, 19(5):1009-1020.

Barber et al., "Restoring Function in Exhausted CD8 T Cells During Chronic Viral Infection," Nature, 2006, 439: 682-687.

Bennett et al., "Program death-1 Engagement Upon TCR Activation Has Distinct Effects on Costimulation and Cytokine-Driven Proliferation: Attenuation of ICOS, IL-4, and IL-21, but Not CD28, IL-7, and IL-15 Responses," J. Immunol., 2003, 170:711-8.

Berge et al., "Pharmaceutical Salts," J Pharmaceutical Sciences, 1977, 66(1):1-19.

(56) References Cited

OTHER PUBLICATIONS

Bertsias et al., "Genetic, Immunologic, and Immunohistochemical Analysis of the Programmed Death 1/programmed Death Ligand 1 Pathway in Human Systemic Lupus Erythematosus,"Arthritis Rheum., 2009, 60(1):207-218.
Blank et al., "PD-L1/B7H-1 Inhibits the Effector Phase of Tumor Rejection by T Cell Receptor (TCR) Transgenic CD8+ T Cells," Cancer Res., 2004, 64(3):1140-1145.
Bois et al., "A phase I and pharmacokinetic study of novel taxane BMS-188797 and cisplatin in patients with advanced solid tumors," Br. J Cancer, 2006, 94(1):79-84.
Brown et al, "Blockade of Programmed death-1 Ligands on Dendritic Cells Enhances T Cell Activation and Cytokine Production," J. Immunol., 2003, 170(3):1257-1266.
Curtin, "Parp Inhibitors and Cancer Therapy," Lands Bioscience and Springer Bioscience, 2006: 218-233.
Dann et al., "BRCA 1/2 mutations and expression: response to platinum chemotherapy in patients with advanced stage epithelial ovarian cancer," Gynecol. Oncol., 2012, 125(3):677-82.
Dong et al., "Tumor-associated B7-H1 Promotes T-cell Apoptosis: A Potential Mechanism of Immune Evasion," Nat. Med., 2002, 8(8):793-800.
Eisenhauer et al., "New response evaluation criteria in solid tumors: Revised RECIST guideline (version 1.1.)," Eur. J. of Cancer, 2009, 45(2):228-247.
Flies et al., "Blockade of the B7-H1/PD-1 Pathway for Cancer Immunotherapy," Yale J. Biol. Med., 2011, 84(4):409-421.
Freeman et al., "Engagement of the PD-1 Immunoinhibitory Receptor bv a Novel B7 Family Member Leads to Negative Regulation of Lymphocyte Activation," J. Exp. Med., 2000, 192(7): 1027-1034.
Gill et al., "Combination of PARP Inhibitor with Temozolamide Drive PARP1 Trapping and Apoptosis in Ewing's Sarcoma," PLOS One, 2015, 10(10):e0140988.
Greenwald et al., "The B7 Family Revisited," Annu. Rev. Immunol., 2000, 23:515-548.
Hamanishi et al., "Programmed Cell Death 1 Ligand 1 and Tumor-Infiltrating CD8+ T Lymphocytes Are Prognostic Factors of Human Ovarian Cancer," Proc. Natl. Acad. Sci. USA, 2007, 104(9):3360-335.
Hennessy et al., "Somatic Mutations in BRCA1 and BRCA2 Could Expand the Number of Patients That Benefit From Poly (ADP Ribose) Polymerase Inhibitors in Ovarian Cancer," J Clin Oncol. 2010, 28(22):3570-3576.
Hirano et al., "Blockade of B7-H1 and PD-1 by Monoclonal Antibodies Potentiates Cancer Therapeutic Immunity," Cancer Res., 2005, 65(3):1089-1096.
Ishida et al., "Induced Expression of PD-1, a Novel Member of the Immunoglobulin Gene Superfamily, Upon Programmed Cell Death," Embo J., 1992, 11(11):3887-95.
Iwai et al., "Involvement of PD-L1 on Tumor Cells in the Escape From Host Immune System and Tumor Immunotherapy by PD-L1 Blockade," Proc. Natl. Acad. Sci. USA, 2002, 99(9):12293-12297.
Iwai et al., "PD-1 Blockade Inhibits Hematogenous Spread of Poorly Immunogenic Tumor Cells by Enhanced Recruitment of Effector T Cells," Int. Immunol., 2005, 17(2):133-144.
Kelley et al., "Targeting DNA repair pathways for cancer treatment: what's new?," Future Oncol., 2014, 10(7):1215-37.
Kroner et al., "A PD-1 Polymorphism Is Associated With Disease Progression in Multiple Sclerosis," Ann. Neurol., 2005, 58(1): 50-57.
Latchman et al., "PD-L2 Is a Second Ligand for PD-1 and Inhibits T Cell Activation," Nat. Immunol., 2001 2(3): 261-238.
Ledermann et al., "Olaparib maintenance therapy in patients with platinum-sensitive relapsed serous ovarian cancer: a preplanned retrospective analysis of outcomes by BRCA status in a radomised phase 2 trial," The Lancet, 2014, 15(8):852-61.
Ledermann et al., "Olaparib Maintenance Therapy in Platinum-Sensitive Relapsed Ovarian Cancer," New England Journal of Medicine, 2012, 366:1382-92.

Mansoor et al., "Niraparib Maintenance Therapy in Platinum-Sensitive Recurrent Ovarian Cancer," The New England Journal of Medicine, 2016, 375(22):2154-2164.
Meyers et al., "Optimal Alignments in Linear Space," Comput. Appl. Biosci., 1989, 4(1):11-17.
Ni et al., "PD-1 Gene Haplotype Is Associated With the Development of Type 1 Diabetes Mellitus in Japanese Children," Hum. Genet., 2007, 121(2):223-232.
Nielsen et al., "Association of a Putative Regulatory Polymorphism in the PD-1 Gene With Susceptibility to Type 1 Diabetes," Tissue Antigens, 2003, 62(6):492-497.
Nishimura et al., "Development of Lupus-Like Autoimmune Diseases by Disruption of the PD-1 Gene Encoding an ITIM Motif-Carrying Immunoreceptor," Immunity, 1999, 11(2):141-151.
Okazaki et al., "New Regulatory Co-Receptors: Inducible Co-Stimulator and PD-1," Curr. Opin. Immunol., 14(6):779-82.
Parry et al., "CTLA-4 and PD-1 Receptors Inhibit T-cell Activation by Distinct Mechanisms," Mol. Cell. Biol., 2005, 25(21):9543-9553.
Patnaik et al., "Phase I study of MK-3475 (anti-PD-1 monoclonal antibody) in patients with advanced solid tumors," Journal of Clinical Oncology, 2012, 30(15):Abstract #2512.
PCT International Search Report and Written Opinion in International Appln. No. PCT/US2018/054606, dated Mar. 28, 2019, 15 pages.
PCT International Search Report and Written Opinion in International Appln. No. PCT/US2018/053542, dated Dec. 14, 2018, 8 pages.
PCT Invitation to Pay Additional Fees in International Appln. No. PCT/US2018/054606, dated Feb. 5, 2019, 10 pages.
PCT Invitation to Pay Additional Fees in International Appln. No. PCT/US2018/067653, dated Apr. 2, 2019, 18 pages.
Pfisterer et al., "Gemcitabine plus carboplatin compared with carboplatin in patients with platinum-sensitive recurrent ovarian cancer: an intergroup trial of the AGO-OV AR, the NCIC CTG, and the EORTC GCG," J Clin. Oncol., 2006, 24(29):4699-707.
Popova et al., "Ploidy and large-scale genomic instability consistently identify basal-like breast carcinomas with BRCA1/2 inactivation," Cancer Res, 2012, 72:5454-62.
Porichis et al., "Role of PD-1 in HIV Pathogenesis and as Target for Therapy," Curr. HIV/AIDS Rep., 2012, 9(1):81-90.
Rustin et al., "Definitions for Response and Progression in Ovarian Cancer Clinical Trials Incorporating RECIST 1.1 and CA 125 Agreed by the Gynecological Cancer Intergroup (GCIG)," Int J Gynecol Cancer, 2011, 21:419-423.
Sharpe et al., "The Function of Programmed Cell Death 1 and Its Ligands in Regulating Autoimmunity and Infection," Nat. Immunol., 2007, 8(3):239-245.
Tahoori et al., "Association of Programmed Cell death-1 (PDCD-1) Gene Polymorphisms With Rheumatoid Arthritis in Iranian Patients," Clin. Exp. Rheumatol., 2011, 29(5):763-767.
Tang et al., "Programmed Death 1 Pathway Inhibition in Metastatic Renal Cell Cancer and Prostate Cancer," Current Oncology Reports, 2013, 15(2):98-104.
Tentori et al., "Pharmacological Strategies to Increase the Antitumor Activity of Methylating Agents," Current Medicinal Chemistry, 2002, 9(13):1285-1301.
Topalian et al., "Safety, Activity, and Immune Correlates of anti-PD-1 Antibody in Cancer," New England J. Med., 2012, 366(26):2443-2454.
Turner et al., "Hallmarks of 'BRCAness' in sporadic cancers," Nat. Rev. Cancer, 2004, 4(10):814-19.
Weber, "Immune Checkpoint Proteins: A New Therapeutic Paradigm for Cancer—Preclinical Background: CTLA-4 and PD-1 Blockade," Semin. Oncol., 2010, 37(5):430-439.
Yamazaki et al., "Expression of Programmed Death 1 Ligands by Murine T Cells and APC," J. Immunol., 2002, 169(10):5538-5545.
Lee et al., "Safety and Clinical Activity of the Programmed Death-Ligand 1 Inhibitor Durvalumab in Combination With Poly (ADP-Ribose) Polymerase Inhibitor Olaparib or Vascular Endothelial Growth Factor Receptor 1-3 Inhibitor Cediranib in Women's Cancers: A Dose-Escalation, Phase I Study", Journal of Clinical Oncology, Jul. 2017, 35(19):2193-2202.

(56) References Cited

OTHER PUBLICATIONS

PCT International Preliminary Report on Patentability in International Application No. PCT/US2018/053542, dated Mar. 31, 2020, 5 pages.
PCT International Preliminary Report on Patentability in International Application No. PCT/US2018/054606, dated Apr. 8, 2020, 7 pages.
PCT International Preliminary Report on Patentability in International Application No. PCT/US2018/067653, dated Jun. 30, 2020, 11 pages.
PCT International Preliminary Report on Patentability in International Application No. PCT/US2019/049346, dated Mar. 9, 2021, 15 pages.
PCT International Search Report and Written Opinion in International Application No. PCT/US2018/067653, dated May 27, 2019, 18 pages.
Adams et al, "Phase 2 study of pembrolizumab (pembro) monotherapy for previously treated metastatic triple-negative breast cancer (mTNBC): KEYNOTE-086 cohort A", Journal of Clinical Oncology, May 2017, 35(15)1008 (abstract only).
Agata et al., "Expression of the PD-1 antigen on the surface of stimulated mouse T and B lymphocytes", International Immunology, May 1996, 8(5):765-772.
American Cancer Society. Cancer Facts & Figures 2016. Atlanta: American Cancer Society 2016; retrieved on Oct. 26, 2020, retrieved from URL: http://www.cancer.org/acs/groups/content/@research/documents/document/acspc-047079.pdf, 3 pages.
Andreae et al., "Maturation and activation of dendritic cells induced by lymphocyte activation gene-3 (CD223)," J. Immunol., 2002, 168:3874-3880.
Anonymous, "History of Changes for Study: NCT03308942," Jun. 18, 2018, retrieved on Oct. 26, 2020, retrieved from URL: https://clinicaltrials.gov/ct2/history/NCT03308942?V_5=View#StudyPageTop, 15 pages.
Anonymous, "TESARO announces expansion to second stage of JASPER trial of ZEJULA in combination with TSR-042 in non-small cell lung cancer," Sep. 4, 2018, retrieved on Oct. 26, 2020, retrieved from URL: https://www.globenewswire.com/news-release/2018/09/04/1565255/0/en/TESARO-Announces-Expansion-to-Second-Stage-of-JASPER-Trial-of-ZEJULA-in-Combination-With-TSR-042-in-Non-Small-Cell-Lung-Cancer.html, 4 pages.
Baixeras et al., "Characterization of the lymphocyte activation gene 3-encoded protein. A new ligand for human leukocyte antigen class II antigens," J. Exp. Med., 1992, 176:327-337.
Bhatia et al., "Immunobiology of Merkel cell carcinoma: implications for immunotherapy of a polyomavirus-associated cancer," Curr. Oncol. Rep., 2011, 13(6):488-497.
Blackburn et al., "Coregulation of CD8+ T cell exhaustion by multiple inhibitory receptors during chronic viral infection," Nat. Immunol., 2009, 10:29-37.
Boland et al., "Microsatellite instability in colorectal cancer", Gastroenterology, 2010, 138(6):2073-2087.
Brinkman et al., "The making of bispecific antibodies," Mabs, 2017, 9(2):182-212.
ClinicalTrials.gov [online], "Niraparib in Combination With Pembrolizumab in Patients With Triple-negative Breast Cancer or Ovarian Cancer (TOPACIO)", Jan. 18, 2016, retrieved on Feb. 16, 2021, retrieved from URL <"https://clinicaltrials.gov/ct2/show/NCT02657889?term=NCT+02657889&draw=2&rank=1">, 10 pages.
Davies et al., "Antibody-antigen complexes," Annual Rev Biochem., 1990, 59:439-473.
De la Chapelle et al., "Clinical Relevance of Microsatellite Instability in Colorectal Cancer", Journal of Clinical Oncology, 2010, 28(20):3380-3387.
Domagala et al., "BRCA1/2-negative hereditary triple-negative breast cancers exhibit BRCAness : Hereditary triple-negative breast cancer and BRCAness", International Journal of Cancer, Apr. 2017, 140(7):1545-1550.
Dougherty et al., "Biological and clinical evidence for somatic mutations in BRCA1 and BRCA2 as predictive markers for olaparib response in high-grade serous ovarian cancers in the maintenance setting", Oncotarget, Jul. 2017, 8(27):43653-43661.
Du Bois et al., "Addition of Epirubicin As a Third Drug to Carboplatin-Paclitaxel in First-Line Treatment of Advanced Ovarian Cancer: A Prospectively Randomized Gynecologic Cancer Intergroup Trial by the Arbeitsgemeinschaft Gynaekologische Onkologie Ovarian Cancer Study Group and the Groupe d'Investigateurs Nationaux pour l'Etude des Cancers Ovariens", Journal of Clinical Oncology, Mar. 2006, 24(7):1127-1135.
Duggan et al., "Microsatellite Instability in Sporadic Endometrial Carcinoma", Journal of the National Cancer Institute, Aug. 1994, 86(16):1216-1221.
Dutcher et al., "A phase II study of interleukin-2 and lymphokine-activated killer cells in patients with metastatic malignant melanoma," J. Clin. Oncol., 1989, 7:477-485.
Erdal et al., "A prosurvival DNA damage-induced cytoplasmic interferon response is mediated by end resection factors and is limited by Trex1," Genes Dev. 2017, 31:353-369.
Foa et al., "Treatment of acute myeloid leukemia patients with recombinant interleukin 2: a pilot study," Br. J. Haematol., 1991, 77:491-496.
Gadducci et al., "PARP inhibitors alone and in combination with other biological agents in homologous recombination deficient epithelial ovarian cancer: From the basic research to the clinic", Critical Reviews in Oncology/Hematology, Jun. 2017, 114:153-165.
Gelmon et al., "Olaparib in patients with recurrent high-grade serous or poorly differentiated ovarian carcinoma or triple-negative breast cancer: a phase 2, multicentre, open-label, non-randomized study," Lancet Oncol., 2011, 12:852-861.
Goyal et al., "Hereditary cancer syndromes: utilizing DNA repair deficiency as therapeutic target", Familial Cancer, Feb. 2016, 15:359-366.
Grosso et al., "LAG-3 regulates CD8+ T cell accumulation and effector function in murine self-and tumor-tolerance systems," J. Clin. Invest., 2007, 117:3383-92.
Guo et al., "Combined TIM-3 blockade and CD137 activation affords the long-term protection in a murine model of ovarian cancer," Journal of Translational Medicine, 2013, 11:215.
Gurin et al., "Causes and Consequences of Microsatellite Instability in Endometrial Carcinoma", Molecular Biology and Genetics, Jan. 1999, 59(2):462-466.
Hamanishi et al., "Safety and Antitumor Activity of Anti-PD-1 Antibody, Nivolumab, in Patients With Platinum-Resistant Ovarian Cancer", Journal of Clinical Oncology, Sep. 2015, 33:4015-4022.
Heong et al., "Update on immune checkpoint inhibitors in gynecological cancers", Journal of Gynecological Oncology, Mar. 2017, 28(2):e20, 19 pages.
Higuchi et al., "CTLA-4 Blockade Synergizes Therapeutically with PARP Inhibition in BRCA1-Deficient Ovarian Cancer," Cancer Immunol Res., 2015, 3:1257-1268.
Huang et al., "CTLA4 blockade induces frequent tumor infiltration by activated lymphocytes regardless of clinical responses in humans," Clin. Can. Res., 2011, 17:4101-4109.
Huang et al., "Role of LAG-3 in regulatory T cells," Immunity, 2004, 21:503-513.
Huang et al., "The PARP1 inhibitor BMN 673 exhibits immunoregulatory effects in a Brca1(−/−) murine model of ovarian cancer," Biochem Biophys Res Commun., 2015, 463:551-556.
Huard et al., "Characterization of the major histocompatibility complex class II binding site on LAG-3 protein," Proc. Nail. Acad. Sci. USA, 1997, 94(11):5744-5749.
Huard et al., "Lymphocyte-activation gene 3/major histocompatibility complex class II interaction modulates the antigenic response of CD4+ T lymphocytes," Eur. J. Immunol., 1994, 24:3216-3221.
Huard et al., "T cell major histocompatibility complex class II molecules down-regulate CD4+ T cell clone responses following LAG-3 binding," Eur. J. Immunol., 1996, 26:1180-1186.
Javle et al., "The role of PARP in DNA repair and its therapeutic exploitation", British Journal of Cancer, Oct. 2011, 105(8):1114-1122.
Jiao et al., "PARP inhibitor upregulates PD-L1 expression and enhances cancer-associated immunosuppression," Clinical Cancer Research, 2017, 23(14):3711-3720.

(56) References Cited

OTHER PUBLICATIONS

Kim et al., "PD-L1 expression on immune cells, but not on tumor cells, is a favorable prognostic factor for head and neck cancer patients," Sci. Rep., 2016, 6:36956.

Konstantinopoulos et al., "Dose-finding combination study of niraparib and pembrolizumab in patients (pts) with metastatic triple-negative breast cancer (TNBC) or recurrent platinum-resistant epithelial ovarian cancer (OC) (TOPACIO/Keynote-162)", Annals of Oncology, Sep. 2017, 28(5):V406-V407.

Konstantinopoulos et al., "Topacio: Preliminary activity and safety in patients (pts) with platinum-resistant ovarian cancer (PROC) in a phase 1/2 study of niraparib in combination with pembrolizumab", Gynecologic Oncology, Jun. 2018, 149(Suppl. 1):246.

Konstantinopoulos, "Pembrolizumab Plus Niraparib Shows Promise in Ovarian Cancer", SGO Annual Meeting, Mar. 27, 2018, retrieved on Feb. 16, 2021, retrieved from URL <"https://www.onclive.com/view/pembrolizumab-plus-niraparib-shows-promise-in-ovarian-cancer">, 3 pages.

Le et al., "PD-1 Blockade in Tumors with Mismatch-Repair Deficiency," N. Engl. J. Med., 2015, 372(26):2509-2520.

Lotze et al., "Interleukin 2," K.A. Smith, Academic Press, Inc., San Diego, Calif., 1988, 237.

Malmqvist, "Biospecific interaction analysis using biosensor technology," Nature, 1993, 361:186-187.

McCans, "Germline BRCA mutation testing to determine eligibility for olaparib maintenance therapy in women with platinum-sensitive relapsed ovarian cancer (including fallopian tube or primary peritoneal cancer) with high grade serous features or a high grade serous component. Applicant Submitted Proposed Protocol", MSAC Application 1380, Dec. 2014, 32 pages.

Moschetta et al., "BRCA somatic mutations and epigenetic BRCA modifications in serous ovarian cancer", Annals of Oncology, Aug. 2016, 27(8):1449-1455.

Mouw et al., "DNA Damage and Repair Biomarkers of Immunotherapy Response," Cancer Discov., 2017, 7:675-693.

Murali, "Classification of endometrial carcinoma: more than two types," Lancet Oncol., 2014, 15(7):e268-78.

Myers et al., "Optimal alignments in linear space", CABIOS, 1988, 4(1):11-17.

Ngiow et al., "Anti-TIM3 antibody promotes T cell IFN-γ-mediated antitumor immunity and suppresses established tumors," Cancer Res., 2011, 71:3540-3551.

Ngiow et al., "Prospects for TIM3-Targeted Antitumor Immunotherapy," Cancer Res., 2011, 71(21):6567-6571.

Nichino et al., "Developing a common language for tumor response to immunotherapy: immune-related response criteria using unidimensional measurements," Clin. Cancer Res., 2013, 19(14):3936-43.

Nomi et al., "Clinical significance and therapeutic potential of the programmed death-1 ligand/programmed death-1 pathway in human pancreatic cancer," Clin Cancer Res., 2007, 13:2151-2157.

PCT International Preliminary Report on Patentability dated Nov. 19, 2019 for PCT/US2018/033437, 12 pages.

PCT International Search Report and Written Opinion in International Appln. PCT/US2019/049346, dated Apr. 9, 2020, 19 pages.

PCT International Search Report dated Oct. 17, 2018 for PCT/US2018/033437, 6 pages.

Pearson, "Using the FASTA program to search protein and DNA sequence databases," Methods Mol. Biol., 1994, 24:307-331.

Pearson, "Using the FASTA program to search protein and DNA sequence databases," Methods Mol. Biol., 1994, 25:365-389.

Popat et al., "Systematic Review of Microsatellite Instability and Colorectal Cancer Prognosis", Journal of Clinical Oncology, Jan. 2005, 23(3):609-618.

Rom-Jurek et al., "Regulation of Programmed Death Ligand 1 (PD-L1) Expression in Breast Cancer Cell Lines In Vitro and in Immunodeficient and Humanized Tumor Mice" Int. J. Mol. Sci., 2018, 16:563.

Rosenberg et al., "A progress report on the treatment of 157 patients with advanced cancer using lymphokine-activated killer cells and interleukin-2 or high-dose interleukin-2 alone," New England Journal of Medicine, 1987, 316(15):889-897.

Rosenberg et al., "The development of new immunotherapies for the treatment of cancer using interleukin-2. A review," Ann. Surgery, 1988, 208:121.

Sakuishi et al., "Targeting Tim-3 and PD-1 pathways to reverse T cell exhaustion and restore anti-tumor immunity," J. Exp. Med., 2010, 207:2187-2194.

Sandhu et al., "The poly(ADP-ribose) polymerase inhibitor niraparib (MK4827) in BRCA mutation carriers and patients with sporadic cancer: a phase 1 dose-escalation trial," Lancet Oncol, 2013, 14:882-892.

Sharma et al., "Primary, Adaptive, and Acquired Resistance to Cancer Immunotherapy," Cell, 2017, 168(4):707-723.

Shukuya et al., "Predictive Markers for the Efficacy of Anti-PD-1/PD-L1 Antibodies in Lung Cancer," Journal of Thoracic Oncology, 2016, 11(7):976-988.

Sierro et al., "The CD4-like molecule LAG-3, biology and therapeutic applications," Expert Opin. Ther. Targets., 2011, 15(1):91-101.

Smith, "Interleukin-2: inception, impact, and implications," Science, 1988, 240(4856):1169-1176.

Udall et al., "PD-L1 diagnostic tests: a systematic literature review of scoring algorithms and test-validation metrics," Diagnostic Pathology, 2018, 13:12.

Umar et al., "Revised Bethesda Guidelines for Hereditary Nonpolyposis Colorectal Cancer (Lynch Syndrome) and Microsatellite Instability", Journal of the National Cancer Institute, Feb. 2004, 96(4):261-268.

Westrop et al., "Opportunities for immunotherapy in microsatellite instable colorectal cancer," Cancer Immunol. Immunother., 2016, 65(10):1249-1259.

Woo et al., "Immune inhibitory molecules LAG-3 and PD-1 synergistically regulate T-cell function to promote tumoral immune escape," Cancer Res., 2012, 72:917-927.

Woof et al., "Human antibody-Fc receptor interactions illuminated by crystal structures," Nat. Rev. Immunol., 2004, 4:89-99.

Workman et al., "Negative regulation of T cell homeostasis by lymphocyte activation gene-3 (CD223)," J. Immunol., 2005, 174:688-695.

Written Opinion of the International Searching Authority dated Oct. 17, 2018 for PCT/US2018/033437, 11 pages.

Zhu et al., "Programmed death-1 pathway blockade produces a synergistic antitumor effect: combined application in ovarian cancer", Journal of Gynecologic Oncology, Sep. 2017, 28(5):e64.

American Cancer Society, Cancer Facts & Figures, 2018, 76 pages.

Anderson et al., "TIM-3 in autoimmunity," Current Opinion in Immunology, Dec. 2006, 18:665-669.

Anderson, "Tim-3, a negative regulator of anti-tumor immunity," Current Opinion in Immunology, Apr. 2012, 24(2):213-216.

Ayers et al., "IFN-γ-related mRNA profile predicts clinical response to PD-1 blockade," J. Clin. Invest., 2017, 127(8):2930-2940.

Bohnsack et al., "Adaptation of the immune-related response criteria: iRecist," ESMO, 2014, ABSTRACT 4958.

Chiba et al., "Tumor-infiltrating DCs suppress nucleic acid-mediated innate immune responses through interactions between the receptor TIM-3 and the alarmin HMGB1," Nature Immunology, Jul. 2012, 13:832-842.

ClinicalTrials.gov [online], "A Study of Niraparib Combined With Bevacizumab Maintenance Treatment in Participants With Advanced Ovarian Cancer Following Response on Front-Line Platinum-Based Chemotherapy," U.S. National Library of Medicine, Oct. 31, 2017, retrieved on Mar. 18, 2022, retrieved from URL <https://clinicaltrials.gov/ct2/show/NCT03326193>, 13 pages.

ClinicalTrials.gov [online], "Niraparib in Combination With Cabozantinib (XL184) in Patients With Advanced Urothelial Cancer (Nicaragua) (Nicaragua)," U.S. National Library of Medicine, Feb. 7, 2018, retrieved on Mar. 18, 2022, retrieved from URL <https://clinicaltrials.gov/ct2/show/NCT03425201>, 12 pages.

ClinicalTrials.gov [online], "Niraparib Versus Niraparib-bevacizumab Combination in Women With Platinum-sensitive Epithelial Ovarian Cancer (AVANOVA)," U.S. National Library of

(56) References Cited

OTHER PUBLICATIONS

Medicine, Feb. 3, 2015, retrieved on Mar. 18, 2022, retrieved from URL <https://clinicaltrials.gov/ct2/show/NCT02354131>, 10 pages.
ClinicalTrials.gov [online], "Platine, Avastin and OLAparib in 1st Line (PAOLA-1)," U.S. National Library of Medicine, Jun. 23, 2015, retrieved on Mar. 18, 2022, retrieved from URL <https://www.clinicaltrials.gov/ct2/show/NCT02477644>, 11 pages.
DeKruyff et al., "T Cell/Transmembrane, Ig, and Mucin-3 Allelic Variants Differentially Recognize Phosphatidylserine and Mediate Phagocytosis of Apoptotic Cells," The Journal of Immunology, Feb. 2010, 184(4):1918-1930.
Han et al., "Tim-3: an activation marker and activation limiter of innate immune cells," Frontiers in Immunology, Dec. 2013, 4(449):1-7.
Hastings et al., "TIM-3 is Expressed on Activated Human CD4+ T Cells and Regulates Th1 and Th17 Cytokines," European Journal of Immunol., Oct. 2009, 39(9):2492-2501.
Huang et al., "CEACAM1 regulates TIM-3-mediated tolerance and exhaustion," Nature, 2014, 517(7534):386-390.
Kane, "TIM Proteins and Immunity," Journal of Immunology, Mar. 2010, 184(6):2743-2749.
Killmurray, "Niraparib/Bevacizumab Combo Continues to Show Prolonged PFS in Patients With Advanced Ovarian Cancer," Targeted Oncology, Mar. 20, 2021, retrieved on Mar. 18, 2022, retrieved from URL <https://www.targetedonc.com/view/niraparib-bevacizumab-combo-continues-to-show-prolonged-pfs-in-patients-with-advanced-ovarian-cancer>, 3 pages.
Liberal et al., "The Impaired Immune Regulation of Autoimmune Hepatitis Is Linked to a Defective Galectin-9/Tim-3 Pathway," Hepatology, 2012, 56(2):677-686.
Miller et al., "The status of poly(adenosine diphosphate-ribose) polymerase (PARP) inhibitors in ovarian cancer, part 2: extending the scope beyond olaparib and BRCA1/2 mutations," Clinical Advances in Hematology & Oncology, 2016, 14(9):704-711.
Mirza et al., "Niraparib plus bevacizumab versus niraparib alone for platinum-sensitive recurrent ovarian cancer (NSGO-AVANOVA2/ENGOT-ov24): a randomised, phase 2, superiority trial," Lancet Oncology, Aug. 29, 2019, pp. 1-11.
Monney et al., "Th1-specific cell surface protein Tim-3 regulates macrophage activation and severity of an autoimmune disease," Nature, Jan. 2002, 415:536-541.
Nakayama et al., "Tim-3 mediates phagocytosis of apoptotic cells and cross-presentation," Blood, Apr. 2009, 113(16):3821-3830.
Richter et al., "On the role of the inhibitory receptor LAG-3 in acute and chronic LCMV infection," International Immunology, Oct. 2009, 22(1):13-23.
Sakuishi et al., "Emerging Tim-3 functions in anti-microbial and tumor immunity," Trends in Immunology, Aug. 2011, 32(8):345-349.
Schmid et al., "New perspectives in ovarian cancer treatment," Maturitas, Feb. 2014, 77(2):128-136.
Sternberg, "Niraparib-Bevacizumab Combo Improves Clinical Outcomes in Recurrent Ovarian Cancer," Cancer Network, Jun. 5, 2020, retrieved on Mar. 18, 2022, retrieved from URL <https://www.cancernetwork.com/view/niraparib-bevacizumab-combo-improves-clinical-outcomes-recurrent-ovarian-cancer>, 2 pages.
U.S. Food and Drug Administration, "ZEJULA (niraparib) capsules: Highlights of Prescribing Information," Mar. 2021, 37 pages.
Wu et al., "Blockade of Tim-3 signaling restores the virus-specific CD8+ T-cell response in patients with chronic hepatitis B", European Journal of Immunology, 2012, 42(5):1180-1191.
Zhu et al., "The Tim-3 ligand galectin-9 negatively regulates T helper type 1 immunity," Nature Immunology, 2005, 6:1245-1252.
Hao et al., "A new oral polybosphate adenosine ribose polymerase inhibitor—niraparib," Clinical Medication Journal, Jun. 2017, 15(6): 13-17 (with English translation).
Jones et al., "Discovery of 2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and -2 Mutant Tumors," Journal of Medicinal Chemistry, Oct. 2009, 52(22): 7170-7185.
Qu, "Clinical analysis of 26 cases of ovarian cancer treated with bevacizumab," China Health Care & Nutrition, Dec. 2014, No. 4 (II): 1882 (with English translation).
Sameni et al., "Cabozantinib (XL184) inhibits growth and invasion of preclinical TNBC models," Clinical Cancer Research, Oct. 2015, 22(4): 923-934.
Vergote et al., "A phase 2 randomised discontinuation trial of cabozantinib in patients with ovarian carcinoma," European Journal of Cancer, 2017, 83: 229-236.
Zhao et al., "A case of triple-negative breast cancer treated with bevacizumab," Journal of Practical Oncology, Jun. 2009, 24(3): 291-292 (with English translation).
Brown et al, "Combining DNA damaging therapeutics with immunotherapy: more haste, less speed", British Journal of Cancer, Nov. 9, 2017, 118 (3):312-324.
ClinicalTrials.gov [online], "A Phase I/II Study of MEDI4736 in Combination With Olaparib in Patients With Advanced Solid Tumors. (MEDIOLA)," U.S. National Library of Medicine, Apr. 12, 2016, retrieved on Jul. 6, 2022, retrieved from URL<https://clinicaltrials.gov/ct2/show/NCT02734004>, 17 pages.
clinicaltrials.gov [online], "Phase I/II Study of the Anti-Programmed Death Ligand-1 Durvalumab Antibody (MEDI4736) in Combination With Olaparib and/or Cediranib for Advanced Solid Tumors and Advanced or Recurrent Ovarian, Triple Negative Breast, Lung, Prostate and Colorectal Cancer," NCT02484404, last updated on Nov. 1, 2022, retrieved on Nov. 9, 2022, retrieved from URL<https://www.clinicaltrials.gov/ct2/show/NCT02484404>, 15 pages.
Clinicaltrials.gov [online],"Niraparib in Combination With Pembrolizumab in Patients With Triple-negative Breast Cancer or Ovarian Cancer (TOPACIO)," NCT02657889, last updated Oct. 26, 2021, retrieved on Nov. 28, 2022, retrieved from URL<https://clinicaltrials.gov/ct2/show/NCT02657889>, 13 pages.
Extended European Search Report and Written Opinion dated Feb. 11, 2021, for EP Patent Application No. 18797986.9, 16 pages.
Hamanishi et al., "Immune Checkpoint Inhibition in Ovarian Cancer," International Immunology, Apr. 7, 2016, 28(7): 339-348.
Hamanishi et al., "PD1/PDL1 Blockade in Cancer Treatment: Perspectives and Issues," Int. J. Clin. Oncol., Feb. 22, 2016, 21: 462-473.
International Search Report and Written Opinion in International Appln. No. PCT/US2018/031876, dated Aug. 6, 2018, 14 pages.
Isnansetyo et al., "Cytotoxicity of Fucoidan from Three Tropical Brown Algae Against Breast and Colon Cancer Cell Lines," Pharmacogn J., 2017, 9(1):14-20.
Kuo et al., "Casuarinin from the Bark of Terminalia arjuna Induces Apoptosis and Cell Cycle Arrest in Human Breast Adenocarcinoma MCF-7 Cells," Planta Med., 2005, 71(3):237-243.
Liu et al, What is the Place of PARP Inhibitors in Ovarian Cancer Treatment?, Curr Oncol Rep. 2016, 18:29, 9 pages.
Mantovani et al., "The chemokine system in cancer biology and therapy," Science Direct, Feb. 2010, 21(1):27-39.
Mirza et al., "Abstract: A phase I study of bevacizumab in combination with niraparib in patients with platinum-sensitive epithelial ovarian cancer: The ENGOT-OV24/AVANOVA1 trial," Journal of Clinical Oncology, May 20, 2016, 34(15_Suppl):5555.
Morales et al., "Review of poly (ADP-ribose) polymerase (PARP) mechanisms of action and rationale for targeting in cancer and other diseases," Crit. Rev. Eukaryot., 2014, Gene Expr. 24, 15-28.
Morris et al, "A Comprehensive Clinical Guide" Cancer, 2005, Chapter 6, pp. 41-44.
Robillard et al., "Abstract 3650: Preclinical evaluation of the PARP inhibitor rucaparib in combination with PD-1 and PD-L1 inhibition in a syngeneic BRCA1 mutant ovarian cancer model," Cancer Research, Jul. 1, 2017, 77(13_Supplement):3650.
Stolze et al., "Comparative analysis of KRAS codon 12, 13, 18, 61 and 117 mutations using human MCF10A isogenic cell lines," Science Reports, Feb. 23, 2015, 9 pages.
Vela et al., "Chemokine receptor-specific antibodies in cancer immunotherapy: achievements and challenges," Frontiers in Immunology, Jan. 30, 2015, 6(12):1-15.

(56) References Cited

OTHER PUBLICATIONS

Yehia et al., "The Clinical Spectrum of PTEN Mutations," Annu. Rev. Med., Jan. 27, 2020, 71:103-16.
Matulonis et al., "NRG/GOG 186K: A randomized phase II study of NCI-supplied cabozantinib versus weekly paclitaxel in the treatment of persistent or recurrent epithelial ovarian, fallopian tube, or primary peritoneal cancer-final results," Gynecol. Oncol., 2016, 141(1):207.
Mirza et al., "ENGOT-OV24-NSGO/ AVANOVA: Niraparib versus bevacizumab-niraparib combination versus bevacizumab and niraparib as sequential therapy in women with platinumsensitive epithelial ovarian, fallopian tube, or peritoneal cancer," Journal of Clinical Oncology, 2015, 33(15), SUPPL. 1, Abstract Only, 4 pages.
Mirza MR et al., "ENGOT-OV24-NSGO/ AVANOVA: Niraparib versus bevacizumab-niraparib combination versus bevacizumab and niraparib as sequential therapy in women with platinumsensitive epithelial ovarian, fallopian tube, or peritoneal cancer," Journal of Clinical Oncology, 2015, 33(15), SUPPL. 1, Abstract Only, 4 pages.
Yelamos et al., "Enhancing tumor-targeting monoclonal antibodies therapy by PARP inhibitors," OncoImmunology, 2016, 5(1):e1065370, 9 pages.

\* cited by examiner

COMBINATION THERAPIES AND USES THEREOF

CROSS-REFERENCE TO RELATED APPLICATIONS

The present application is a 35 U.S.C. § 371 National Stage Application of International Application No. PCT/US2018/054606, filed on Oct. 5, 2018, which claims benefit of U.S. Provisional Application No. 62/569,239, filed Oct. 6, 2017, each of which is hereby incorporated by reference in its entirety.

BACKGROUND

Niraparib is an orally active and potent poly (ADP-ribose) polymerase, or PARP, inhibitor. Niraparib and pharmaceutically acceptable salts thereof, are disclosed in International Publication No. WO2007/113596 and European Patent No. EP2007733B1; International Publication No. WO2008/084261 and U.S. Pat. No. 8,071,623; and International Publication No. WO2009/087381 and U.S. Pat. No. 8,436,185. Methods of making niraparib and pharmaceutically acceptable salts thereof are disclosed in International Publication Nos. WO2014/088983 and WO2014/088984. Methods to treat cancer with niraparib and pharmaceutically acceptable salts thereof are disclosed in U.S. Provisional Patent Application Nos. 62/356,461 and 62/402,427. The contents of each of the foregoing references are incorporated herein by reference in their entirety.

Cancer is a serious public health problem, with about 595,690 people in the United States of America expected to die of cancer in 2016. Modern strategies for the development of novel cancer therapies include agents targeting specific molecular defects that characterize certain cancer cells in order to increase treatment efficacy and reduce toxicities. In breast cancer, targeted therapies have long been effective, as agents targeting hormone receptors in tumors expressing them and as antibodies or tyrosine kinase inhibitors targeting overexpressed or amplified HER2 molecules. Breast tumors expressing none of these are called triple-negative breast cancers (TNBC), which comprise about 15% of breast cancers overall, about 70% of breast cancers in individuals harboring a germline BRCA1 mutation, and 20% in BRCA2 mutation carriers [1, 2, 3, 4]. The discovery of the family of nuclear enzymes poly [ADP-ribose]polymerases (PARPs) and their role in DNA-damage repair pathways opened the possibility of developing a new class of antineoplastic drugs with the ability to interfere with the DNA damage repair systems of cancer cells—PARP inhibitors.

SUMMARY

Provided herein is a method of treating a subject with a disease or condition comprising administering to the subject a first agent that inhibits poly [ADP-ribose] polymerase (PARP); and a second agent, wherein the second agent comprises an angiogenesis inhibitor. Also provided herein is a method of preventing a tumor cell growth in a subject with a disease or condition comprising administering to the subject a first agent that inhibits poly [ADP-ribose]polymerase (PARP); and a second agent, wherein the second agent comprises an angiogenesis inhibitor. Also provided herein is a method of preventing tumor metastasis in a subject with a disease or condition comprising administering to the subject a first agent that inhibits poly [ADP-ribose] polymerase (PARP); and a second agent, wherein the second agent comprises an angiogenesis inhibitor. Also provided herein is a method of inducing an immune response in a subject with a disease or condition comprising administering to the subject a first agent that inhibits poly [ADP-ribose] polymerase (PARP); and a second agent, wherein the second agent comprises an angiogenesis inhibitor. Also provided herein is a method of enhancing an immune response in a subject with a disease or condition comprising administering to the subject a first agent that inhibits poly [ADP-ribose] polymerase (PARP); and a second agent, wherein the second agent comprises an angiogenesis inhibitor.

In some embodiments, the first agent inhibits PARP1, or PARP2, or both.

In some embodiments, the first agent is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; a toxin; or any combination thereof.

In some embodiments, the first agent is a small molecule.

In some embodiments, the first agent is selected from the group consisting of: ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof.

In some embodiments, the first agent is selected from the group consisting of: niraparib, olaparib, rucaparib, talazoparib, veliparib, and salts or derivatives thereof.

In some embodiments, the first agent is niraparib or a pharmaceutically acceptable salt or derivative thereof.

In some embodiments, the angiogenesis inhibitor reduces the production of a pro-angiogenic factor, inhibits an interaction between a pro-angiogenic factor and a pro-angiogenic receptor, inhibits a function of a pro-angiogenic factor, inhibits a function of a pro-angiogenic factor receptor, reduces of blood flow by disruption of blood vessels, inhibits vessel sprouting, or any combinations thereof.

In some embodiments, the pro-angiogenic factor comprises FGF1-14, FGF15/19, FGF18-23, PDGF, VEGF-A, VEGF-B, VEGF-C, VEGF-D, PIGF (placental growth factor), VEGF-E (Orf-VEGF), *Trimeresurus flavoviridis* svVEGF, VEGFR-1, VEGFR-2, VEGFR-3, angiogenin, angiopoietin-1, angiopoietin-2, Tie-1, Tie-2, MMP, Dll4, SEMA3s, ephrins, leptin, chemokines, transforming growth factor-β (TGF-β), or any combination thereof.

In some embodiments, the angiogenesis inhibitor is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; a toxin; or any combination thereof.

In some embodiments, the angiogenesis inhibitor is selected from the group consisting of bevacizumab, itraconazole, carboxyamidotriazole, TNP-470, fumagillin, CM101, IL-12, platelet factor-4, suramin, SU5416, thrombospondin, angiostatic steroids, heparin, cartilage-derived angiogenesis inhibitory factor, matrix metalloproteinase inhibitor, angiostatin, endostatin, 2-methoxyestradiol, tecogalan, tetrathiomolybdate, thrombospondin, thalidomide, prolactin, αVβ3 inhibitor, lenalidomide, linomide, ramucirumab, tasquinimod, ranibizumab, sorafenib, sunitinib, pazopanib, everolimus, tissue inhibitors of metalloproteases (TIMP1 and TIMP2), bFGF soluble receptor, transforming growth factor beta, interferon alpha, soluble KDR and FLT-1 receptors, placental proliferin-related protein, pazopanib, sunitinib, sorafenib, axitinib, ponatinib, cabozantinib, regorafenib, vandetanib, lenvatinib, semaxanib, SU6668, vatalanib, tivozanib, cediranib, protamine, heparin, steroids, ascorbic acid ethers, sulfated polysaccharide DS 4152, fumagillin, AGM 12470, neovastat, R04929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, OMP-21M18, navicixizumab (OMP-305B83), Flt2-11, CBO-P11, Je-11, V1, and any combination thereof.

In some embodiments, the angiogenesis inhibitor inhibits a DLL4/Notch signaling pathway.

In some embodiments, the angiogenesis inhibitor inhibiting the DLL4/Notch signaling pathway is a gamma-secretase inhibitor (GSI), a siRNA, or a monoclonal antibody against a Notch receptor or ligand.

In some embodiments, the angiogenesis inhibitor inhibiting a DLL4/Notch signaling pathway is selected from the group consisting of R04929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, and any combination thereof.

In some embodiments, the angiogenesis inhibitor inhibits a vascular endothelial growth factor (VEGF)/vascular endothelial growth factor receptor (VEGFR) pathway.

In some embodiments, the angiogenesis inhibitor is selected from the group consisting of Akt Inhibitor, calcineurin autoinhibitory peptide, ET-18-OCH3, Go 6983, NG-Nitro-L-arginine methyl ester, p21-activated kinase Inhibitor, cPLA2α inhibitor, PI-103, PP2, SB 203580, U0126, VEGFR tyrosine kinase inhibitor V, VEGFR2 kinase inhibitor VI, VEGFR2 kinase inhibitor III, ZM 336372, and any combination thereof.

In some embodiments, the angiogenesis inhibitor inhibits a VEGF family protein and/or a VEGFR family protein.

In some embodiments, the VEGF family protein comprises VEGF-A, VEGF-B, VEGF-C, VEGF-D, PlGF (placental growth factor), VEGF-E (Orf-VEGF), *Trimeresurus flavoviridis* svVEGF, or any combination thereof.

In some embodiments, the VEGFR family protein comprises VEGFR-1, VEGFR-2, VEGFR-3, or any combination thereof.

In some embodiments, the angiogenesis inhibitor comprises a VEGF inhibitor, a VEGFR inhibitor, or a combination thereof.

In some embodiments, the angiogenesis inhibitor induces homologous recombinant (HR) deficiency.

In some embodiments, the angiogenesis inhibitor induces hypoxia.

In some embodiments, the angiogenesis inhibitor induces homologous recombinant (HR) deficiency by hypoxia.

In some embodiments, the VEGF inhibitor is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; a toxin; or any combination thereof.

In some embodiments, the VEGF inhibitor is an antibody or a fragment thereof.

In some embodiments, the VEGF inhibitor is bevacizumab, ranibizumab, OPT-302, ziv-aflibercept, or any combinations thereof.

In some embodiments, the VEGF inhibitor is a small organic or inorganic molecule.

In some embodiments, the small organic or inorganic molecule is Flt2-11, CBO-P11, Je-11, V1, or any combination thereof.

In some embodiments, the VEGFR inhibitor is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; a toxin; a tyrosine kinase inhibitor; or any combination thereof.

In some embodiments, the VEGFR inhibitor is a tyrosine kinase inhibitor.

In some embodiments, the tyrosine kinase inhibitor is pazopanib, sunitinib, sorafenib, axitinib, ponatinib, cabozantinib, regorafenib, vandetanib, lenvatinib, semaxanib, SU6668, vatalanib, tivozanib, cediranib, or any combination thereof.

In some embodiments, the VEGFR inhibitor is an antibody or a fragment thereof.

In some embodiments, the VEGFR inhibitor is ramucirumab.

In some embodiments, a first agent is niraparib, and a second agent is cabozantinib.

In some embodiments, a first agent is niraparib, and a second agent is bevacizumab.

In some embodiments, administering comprises administering the first and second agent sequentially.

In some embodiments, administering comprises administering the first and second agent simultaneously.

In some embodiments, administering comprises administering the first agent before administering the second agent.

In some embodiments, administering comprises administering the second agent before administering the first agent.

In some embodiments, the subject is a mammalian subject.

In some embodiments, the subject is a mouse.

In some embodiments, the subject is a human.

In some embodiments, the disease or condition is cancer.

In some embodiments, the cancer is selected from the group consisting of carcinoma, squamous carcinoma, adenocarcinoma, sarcomata, endometrial cancer, breast cancer, ovarian cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, neuroma, and combinations thereof.

In some embodiments, the cancer is breast cancer.

In some embodiments, the breast cancer is triple negative breast cancer.

In some embodiments, the cancer is ovarian cancer.

In some embodiments, the cancer is colorectal cancer.

In some embodiments, a first agent is niraparib, and a second agent is cabozantinib.

In some embodiments, a first agent is niraparib, and a second agent is bevacizumab.

In some embodiments, administering the first agent, the second agent, or both comprises administering the first agent, the second agent, or both ocularly, oral, parenterally, topically, bronchially, buccally, intradermally, interdermally, transdermally, enterally, intra-arterially, intradermally, intragastrically, intramedullarily, intramuscular, intranasally, intraperitoneally, intrathecally, intravenously, intraventricularly, within a specific organ (e.g., intrahepaticly), mucosally, nasally, orally, rectally, subcutaneously, sublingually, topically, tracheally, vaginally, vitreally, or any combination thereof.

In some embodiments, administering comprises administering a composition formulated for oral administration comprising the first agent.

In some embodiments, the composition is a capsule.

In some embodiments, the composition is a tablet.

In some embodiments, the composition (e.g., a capsule or tablet) further comprises one or more pharmaceutically acceptable excipients.

In some embodiments, the one or more pharmaceutically acceptable excipients comprises lactose monohydrate, magnesium stearate, or a combination thereof.

In some embodiments, a therapeutically effective amount of the first or second agent is administered.

In some embodiments, the subject has previously been treated with one or more different cancer treatment modalities.

In some embodiments, the subject has previously been treated with one or more of radiotherapy, chemotherapy, or immunotherapy.

In some embodiments, the subject has been treated with one, two, three, four, or five lines of prior therapy.

In some embodiments, the prior therapy is a cytotoxic therapy.

In some embodiments, the method further comprises administering a third agent to the subject, or performing a therapy on the subject selected from the group consisting of surgery, radiotherapy, or a combination thereof.

In some embodiments, the third agent comprises a radiotherapeutic agent, an anti-immunosuppressive agent or immunostimulatory agent, a chemotherapeutic agent, or a combination thereof.

In some embodiments, the anti-immunosuppressive agent or immunostimulatory agent comprises an anti-PD-1 agent, an anti-PD-L1 agent, an anti-CTLA4 agent, an anti-TIM-3 agent, an anti-LAG-3 agent, a GITR (glucocorticoid-induced TNFR-related protein) stimulating agent, an anti-IDO agent, an anti-ICOS agent, an anti-OX40 agent, an anti-CSF1R agent, a chemokine signaling agent, a cytokine signal stimulating agent, or any combination thereof.

In some embodiments, the anti-PD-1 agent is selected from the group consisting of pembrolizumab, nivolumab, PDR001, REGN2810 (SAR-439684), BGB-A317, BI 754091, IBI308, INCSHR-1210, JNJ-63723283, JS-001, MEDI0680 (AMP-514), MGA-012, PF-06801591, REGN-2810, TSR-042, atezolizumab, avelumab, CX-072, durvalumab, FAZ053, LY3300054, PD-L1 millamolecule, and any combinations thereof.

In some embodiments, the anti-PD-L1 agent is selected from the group consisting of atezolizumab, durvalumab, avelumab, LY3300054, and any combinations thereof.

In some embodiments, the GITR stimulating agent is selected from the group consisting of DTA-1, mGITRL, pGITRL, and any combinations thereof.

In some embodiments, the anti-CTLA4 agent is selected from the group consisting of ipilimumab, tremelimumab, and a combination thereof.

In some embodiments, the third agent is an anti-immunosuppressive agent or immunostimulatory agent selected from the group consisting of a flavonoid (e.g., flavonoid glycoside), lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin.

In some embodiments, the third agent is a chemotherapeutic agent selected from the group consisting of aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, vinorelbine, and any combinations thereof.

In some embodiments, a therapeutically-effective amount of a therapeutic agent is administered to a subject. The therapeutic agent can be a first, a second, or a third agent. In some embodiments, the therapeutically-effective amount is from about 0.1 milligram per kilogram of body weight per day (mg/kg/day) to about 1 mg/kg/day, from 1 mg/kg/day to about 5 mg/kg/day, from 5 mg/kg/day to about 10 mg/kg/day, from 10 mg/kg/day to about 15 mg/kg/day, from 15 mg/kg/day to about 20 mg/kg/day, from 20 mg/kg/day to about 25 mg/kg/day, from 25 mg/kg/day to about 30 mg/kg/day, from 30 mg/kg/day to about 35 mg/kg/day, or from 35 mg/kg/day to about 40 mg/kg/day. In some embodiments, the therapeutically-effective amount is from 0.1 mg/kg/day to about 40 mg/kg/day. In some embodiments, the therapeutically-effective amount is from 10 mg/kg/day to about 50 mg/kg/day, or from 50 mg/kg/day to about 100 mg/kg/day.

In some embodiments, a first agent is administered at a dose that is equivalent to about 300 mg of niraparib. In some embodiments, the first agent is administered at a reduced dose. In some embodiments, the reduced dose is equivalent to 200 mg of niraparib. In some embodiments, the reduced dose is equivalent to 100 mg~150 mg, or 150 mg~200 mg of niraparib. In some embodiments, the first agent (e.g. niraparib) is administered at an increased dose if the subject's hemoglobin≥9 g/dL, platelets≥100,000/μL and neutrophils≥1500/μL for all labs performed during one or more treatment cycles. In some embodiments, the dose of the first agent (e.g. niraparib) is increased after two cycles of treatment.

Provided herein is a pharmaceutical composition comprising any of the first agents described herein and any of the second agents described herein. In some embodiments, the pharmaceutical composition further comprises any of the third agents described herein.

Provided herein is a kit comprising any of the first agents described herein and any of the second agents described herein. In some embodiments, the kit further comprises any of the third agents described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Definitions

Figure 1:
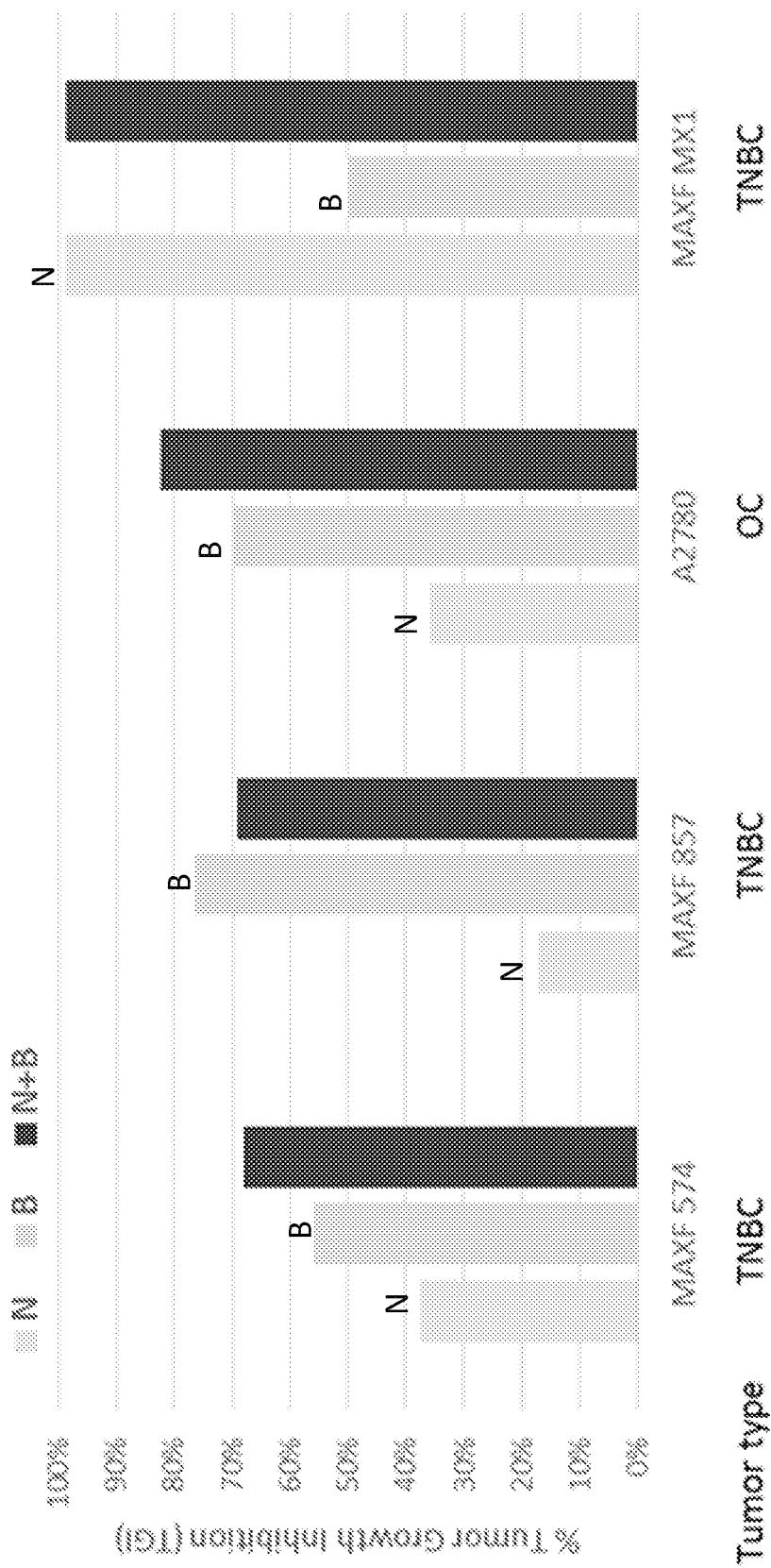
FIG. 1 depicts an exemplary study of niraparib and bevacizumab combination treatment in both ovarian and triple negative breast cancer (TNBC) models.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

As used herein, the term "administration" typically refers to the administration of a composition to a subject or system. Those of ordinary skill in the art will be aware of a variety of routes that may, in appropriate circumstances, be utilized for administration to a subject, for example a human subject. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

As used herein, the terms "dosage form" or "unit dosage form" refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a regimen that has been determined to correlate with a desired or beneficial outcome when administered to a relevant population (e.g., with a therapeutic regimen). Those of ordinary skill in the art appreciate that the total amount of a therapeutic composition or agent administered to a particular subject is determined by one or more attending physicians and may involve administration of multiple dosage forms.

As used herein, the term "regimen" refers to a set of unit doses (typically more than one) that are administered individually to a subject, typically separated by one or more periods of time. In some embodiments, a given therapeutic agent is administered according to a regimen, which may involve one or more doses. In some embodiments, a regimen comprises a plurality of doses each of which is separated in time from other doses. In some embodiments, individual doses are separated from one another by a time period of the same length; in some embodiments, a regimen comprises a plurality of doses, wherein the doses are separated by time periods of different length. In some embodiments, a regimen comprises doses of the same amount. In some embodiments, a regimen comprises doses of different amounts. In some embodiments, a regimen comprises at least one dose, wherein the dose comprises one unit dose of the therapeutic agent. In some embodiments, a regimen comprises at least one dose, wherein the dose comprises two or more unit doses of the therapeutic agent.

As used herein, the term "effective amount" refers to the amount of a therapeutic agent disclosed herein which treats, upon single or multiple dose administration, a subject with a disease or condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to: the species of the subject; its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the therapeutic agent disclosed herein is expected to vary from about 0.1 milligram per kilogram of body weight per day (mg/kg/day) to about 40 mg/kg/day. Specific amounts can be determined by the skilled person.

As used herein, the term "patient", "subject", or "test subject" refers to any organism, including a human or non-human, to which provided therapeutic agent or agents described herein are administered in accordance with the present disclosure e.g., for experimental, diagnostic, prophylactic, and/or therapeutic purposes. Typical subjects include animals (e.g., mammals such as mice, rats, rabbits, canines, felines, horses, cattle, pigs, deer, non-human primates, and humans; insects; worms; birds; reptiles; amphibians; etc.). In embodiments, the subject is a human. In some embodiments, the subject is a mouse. In some embodiments, a subject may be suffering from, and/or susceptible to a disease, disorder, and/or condition (e.g., cancer). In some embodiments, a patient is a human that has been diagnosed with a cancer. In some embodiments, a patient is a human possessing one or more female reproductive organs.

"Diluents" is a diluting agent and is also referred to as a filler, dilutant or thinner. "Diluents" increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like. Combinations of one or more diluents can also be used.

The term "excipient" means a pharmacologically inactive component such as a diluent, lubricant, surfactant, carrier, or the like. Excipients that are useful in preparing a pharmaceutical composition are generally safe, non-toxic and are acceptable for human pharmaceutical use. Reference to an excipient includes both one and more than one such excipient. Co-processed excipients are also covered under the scope of present disclosure.

"Filling agents" or "fillers" can refer to "diluents" and include compounds such as lactose, lactose monohydrate, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, magnesium stearate, calcium hydroxide, talc, sodium stearyl fumarate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Those skilled in the art are well familiar with antibody structure and sequence elements, recognize "variable" and "constant" regions in provided sequences, and understand that there may be some flexibility in definition of a "boundary" between such domains such that different presentations of the same antibody chain sequence may, for example, indicate such a boundary at a location that is shifted one or a few residues relative to a different presentation of the same antibody chain sequence. Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]).

As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, an antibody agent utilized in accordance with the present disclosure is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]). In many embodiments, an antibody agent is or comprises a polypeptide whose amino acid sequence includes one or more structural elements recognized by those skilled in the art as a complementarity determining region (CDR); in some embodiments, an antibody agent is or comprises a polypeptide whose amino acid sequence includes at least one CDR (e.g., at least one heavy chain CDR and/or at least one light chain CDR) that is substantially identical to one found in a reference antibody. In some embodiments, an included CDR is substantially identical to a reference CDR in that it is either identical in sequence or contains between 1-5 amino acid substitutions as compared with the reference CDR. In some embodiments, an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments, an included CDR is substantially identical to a reference CDR in that it shows at least 96%, 96%, 97%, 98%, 99%, or 100% sequence identity with the reference CDR. In some embodiments, an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an included CDR is substantially identical to a reference CDR in that at least one amino acid within the included CDR is substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

As used herein, the term "combination therapy" refers to a clinical intervention in which a subject is exposed to two or more therapeutic regimens (e.g., two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

As used herein, the term "angiogenesis" means any growth of blood vessels or any neo- or re-vascularization of a tissue. The growth may or may not be stimulated by cytokines, such as cytokine-mediated activation of blood vessel endothelial cells.

As used herein, the terms "metastasis" and "metastases" refer to the movement of a tumor cell from its primary site by any means or by any route, including local invasion, lymphatic spread, vascular spread or transcoelomic spread.

The terms "enhance" or "enhancing" refers to an increase or prolongation of either the potency or duration of a desired effect of a composition described herein, or a diminution of any adverse symptomatology that is consequent upon the administration of the therapeutic agent or agents. Thus, in regard to enhancing the effect of niraparib disclosed herein, the term "enhancing" refers to the ability to increase or prolong, either in potency or duration, the effect of other therapeutic agents that are used in combination with niraparib disclosed herein. An "enhancing-effective amount," as used herein, refers to an amount of niraparib or other therapeutic agent which is adequate to enhance the effect of another therapeutic agent or niraparib in a desired system. When used in a patient, amounts effective for this use will depend on the severity and course of the disease, disorder or condition, previous therapy, the patient's health status and response to the drugs, and the judgment of the treating physician.

Overview

The present disclosure provides a combination therapy for a disease such as cancer. In the case of cancer therapy, the amalgamation of anti-cancer drugs can enhance efficacy compared to the monotherapy approach because it can target key pathways in a characteristically synergistic or an additive manner. This approach can potentially reduce drug resistance, while simultaneously providing therapeutic anti-cancer benefits, such as reducing tumor growth and metastatic potential, arresting mitotically active cells, reducing cancer stem cell populations, and inducing apoptosis.

The present disclosure provides combination therapies of PARP inhibitors and angiogenesis inhibitors. This combination benefit may be related to angiogenesis inhibitor-mediated conditional genetic instability. For example, angiogenesis inhibition can induce hypoxia, which could in turn downregulate homologous recombinant (HR) repair genes such as RAD51 and BRCA1. In addition, acute hypoxia and reoxygenation can induce both single strand and double strand DNA break within tumor cells as a result of increased levels of reactive oxygen species (ROS). Therefore, when cells are under hypoxic stress exerted by angiogenesis inhibitors, increased DNA damage and deficiency of the HR repair pathway may lead to heightened sensitivity to PARP inhibitors.

Provided herein is a method of treating a subject with a disease or condition, comprising administering to the subject a first agent and a second agent. Also provided herein is a method of preventing tumor cell growth in a subject with a disease or condition, comprising administering to the subject a first agent and a second agent. Further, provided herein is a method of preventing tumor metastasis in a subject with a disease or condition, comprising administering to the subject a first agent and a second agent. In a fourth aspect, provided herein is a method of inducing an immune response in a subject with a disease or condition comprising administering to the subject a first agent and a second agent. In a fifth aspect, provided herein is a method of enhancing an immune response in a subject with a disease or condition comprising administering to the subject a first agent and a second agent.

In various embodiments, the first agent provided herein inhibits poly [ADP-ribose]polymerase (PARP). In some cases, the first agent is selected from the group consisting of: niraparib, olaparib, rucaparib, talazoparib, and veliparib, or salts or derivatives thereof. In various embodiments, the second agent provided herein comprises an angiogenesis inhibitor. In some cases, the angiogenesis inhibitor can reduce the production of a pro-angiogenic factor, inhibit an interaction between a pro-angiogenic factor and a pro-angiogenic receptor, inhibit a function of a pro-angiogenic factor, and/or inhibit a function of a pro-angiogenic factor receptor. In some cases, the angiogenesis inhibitor is selected from the group consisting of bevacizumab, itraconazole, carboxyamidotriazole, TNP-470, fumagillin, CM101, IL-12, platelet factor-4, suramin, SU5416, thrombospondin, angiostatic steroids, heparin, cartilage-derived angiogenesis inhibitory factor, matrix metalloproteinase inhibitor, angiostatin, endostatin, 2-methoxyestradiol, tecogalan, tetrathiomolybdate, thrombospondin, thalidomide, prolactin, αVβ3 inhibitor, lenalidomide, linomide, ramucirumab, tasquinimod, ranibizumab, sorafenib, sunitinib, pazopanib, everolimus, tissue inhibitors of metalloproteases (TIMP1 and TIMP2), bFGF soluble receptor, transforming growth factor beta, interferon alpha, soluble KDR and FLT-1 receptors, placental proliferin-related protein, pazopanib, sunitinib, sorafenib, axitinib, ponatinib, cabozantinib, regorafenib, vandetanib, lenvatinib, semaxanib, SU6668, vatalanib, tivozanib, cediranib, protamine, heparin, steroids, ascorbic acid ethers, sulfated polysaccharide DS 4152, fumagillin, AGM 12470, neovastat, R04929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, OMP-21M18, navicixizumab (OMP-305B83), Flt2-11, CBO-P11, Je-11, V1, and any combination thereof.

In some embodiments, the methods further comprise administering a third agent.

Also provided herein is a pharmaceutical composition comprising the first and second agent disclosed herein. In some embodiments, the pharmaceutical composition further comprises the third agent. Also provided herein is a kit comprising the first and the second agent disclosed herein. In some embodiments, the kit further comprises the third agent.

Indications

In some embodiments, the disease or condition that can be treated with the methods disclosed herein is cancer. Cancer is an abnormal growth of cells which tend to proliferate in an uncontrolled way and, in some cases, to metastasize (spread). Cancer is not one disease. It is a group of more than 100 different and distinctive diseases. Cancer can involve any tissue of the body and have many different forms in each body area. Most cancers are named for the type of cell or organ in which they start. A tumor can be cancerous or benign. A benign tumor means the tumor can grow but does not spread. A cancerous tumor is malignant, meaning it can grow and spread to other parts of the body. If a cancer spreads (metastasizes), the new tumor bears the same name as the original (primary) tumor. The frequency of a particular cancer may depend on gender. While skin cancer is the most common type of malignancy for both men and women, the second most common type in men is prostate cancer and in women, breast cancer.

The methods of the disclosure can be used to treat any type of cancer known in the art. Non-limiting examples of cancers to be treated by the methods of the present disclosure can include melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. Additionally, the disease or condition provided herein includes refractory or recurrent malignancies whose growth may be inhibited using the methods of the invention. In some embodiments, a cancer to be treated by the methods of the present disclosure is selected from the group consisting of carcinoma, squamous carcinoma, adenocarcinoma, sarcomata, endometrial cancer, breast cancer, ovarian cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, neuroma, and combinations thereof. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, tongue, larynx, and gullet), and adenocarcinoma (for example, prostate, small intestine, endometrium, cervical canal, large intestine, lung, pancreas, gullet, rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma. In some embodiments, a cancer to be treated by the methods of the present disclosure is breast cancer. In some embodiments, a cancer to be treated by the methods of the present disclosure is triple negative breast cancer (TNBC). In some embodiments, a cancer to be treated by the methods of the present disclosure is ovarian cancer. In some embodiments, a cancer to be treated by the methods of the present disclosure is colorectal cancer.

In some embodiments, a patient or population of patients to be treated with combination therapy of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma. In some embodiments, a patient or population of patients to be treated with combination therapy of the present disclosure have a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), or Multiple myeloma ("MM").

Specific examples of cancers that can be prevented and/or treated in accordance with present disclosure include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangio sarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; colorectal cancer, KRAS mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acrallentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In embodiments, a cancer is breast cancer, ovarian cancer, cervical cancer, epithelial ovarian cancer, fallopian tube cancer, primary peritoneal cancer, endometrial cancer, prostate cancer, testicular cancer, pancreatic cancer, esophageal cancer, head and neck cancer, gastric cancer, bladder cancer, lung cancer (e.g., adenocarcinoma, NSCLC and SCLC), bone cancer (e.g., osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g., liposarcoma), bladder cancer, liver cancer (e.g., hepatocellular carcinoma), kidney cancer (e.g., renal cell carcinoma), myeloid disorders (e.g., AML, CML, myelodysplastic syndrome and promyelocytic leukemia), and lymphoid disorders (e.g., leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma) may be treated with compounds and methods described herein.

In some embodiments, a cancer is a gynecologic cancer (e.g., breast cancer or a cancer of the female reproductive system such as ovarian cancer, fallopian tube cancer, cervical cancer, vaginal cancer, vulvar cancer, uterine cancer, or primary peritoneal cancer). In some embodiments, cancers of the female reproductive system include, but are not limited to, ovarian cancer, cancer of the fallopian tube(s), peritoneal cancer, and breast cancer.

In embodiments, a cancer is an ovarian cancer. The term 'ovarian cancer' is often used to describe epithelial cancers that begin in the ovary, in the fallopian tube, and from the lining of the abdominal cavity, call the peritoneum. In embodiments, a cancer is epithelial ovarian cancer. In embodiments, a cancer is fallopian tube cancer. In embodiments, a cancer is primary peritoneal cancer.

In embodiments, a cancer is a breast cancer. Breast cancer is the second most common cancer in the world with approximately 1.7 million new cases in 2012 and the fifth most common cause of death from cancer, with approximately 521,000 deaths. Of these cases, approximately 15% are triple-negative, which do not express the estrogen receptor, progesterone receptor (PR) or HER2. In some embodiments, triple negative breast cancer (TNBC) is characterized as breast cancer cells that are estrogen receptor expression negative (<1% of cells), progesterone receptor expression negative (<1% of cells), and HER2-negative. In embodiments, a breast cancer is associated with homologous recombination repair deficiency/homologous repair deficiency ("HRD").

Role of poly [ADP-ribose] polymerases (PARPs)

Poly [ADP-ribose] polymerases (PARPs) are a family of enzymes that cleave NAD+, releasing nicotinamide, and successively add ADP-ribose units to form ADP-ribose polymers. Accordingly, activation of PARP enzymes can lead to depletion of cellular NAD+ levels (e.g., PARPs as NAD+ consumers) and mediates cellular signaling through ADP-ribosylation of downstream targets. PARP-1 is a zinc-finger DNA-binding enzyme that is activated by binding to DNA double or single strand breaks. It was known that anti-alkylating agents could deplete the NAD+ content of tumor cells, and the discovery of PARPs explained this phenomenon. Anti-alkylating agents induce DNA strand breaks, which activates PARP-1, which is a part of the DNA repair pathway. Poly ADP-ribosylation of nuclear proteins by PARP-1 converts DNA damage into intracellular signals that can either activate DNA repair (e.g., by the base excision repair (BER) pathway); or trigger cell death in the presence of DNA damage that is too extensive and cannot be efficiently repaired.

PARP-2 contains a catalytic domain and is capable of catalyzing a poly(ADP-ribosyl)ation reaction. PARP-2 can display auto-modification properties similar to PARP-1. The protein is localized in the nucleus in vivo and may account for the residual poly [ADP-ribose]synthesis observed in PARP-1-deficient cells, treated with alkylating agents or hydrogen peroxide. Some agents that inhibit PARP (e.g., agents primarily aimed at inhibiting PARP-1) may also inhibit PARP-2 (e.g., niraparib).

The role of PARP enzymes in DNA damage response (e.g., repair of DNA in response to genotoxic stress) has led to the compelling suggestion that PARP inhibitors may be useful anti-cancer agents. PARP inhibitors may be particularly effective in treating cancers resulting from germ line or sporadic deficiency in the homologous recombination DNA repair pathway, such as BRCA-1 and/or BRCA-2 deficient cancers.

Pre-clinical ex vivo and in vivo experiments suggest that PARP inhibitors are selectively cytotoxic for tumors with homozygous inactivation of BRCA-1 and/or BRCA-2 genes, which are known to be important in the homologous recombination (HR) DNA repair pathway. The biological basis for the use of PARP inhibitors as single agents in cancers with defects in BRCA-1 and/or BRCA-2 can be the requirement of PARP-1 and PARP-2 for base excision repair (BER) of the damaged DNA. Upon formation of single-strand DNA breaks, PARP-1 and PARP-2 can bind at sites of lesions, become activated, and catalyze the addition of long polymers of ADP-ribose (PAR chains) on several proteins associated with chromatin, including histones, PARP itself, and various DNA repair proteins. This can result in chromatin relaxation and fast recruitment of DNA repair factors that access and repair DNA breaks. Normal cells can repair up to 10,000 DNA defects daily and single strand breaks can be the most common form of DNA damage. Cells with defects in the BER pathway can enter S phase with unrepaired single strand breaks. Pre-existing single strand breaks can be converted to double strand breaks as the replication machinery passes through the break. Double strand breaks present during S phase may be repaired by the error-free HR pathway. Cells with inactivation of genes required for HR, such as BRCA-1 and/or BRCA-2, accumulate stalled replication forks during S phase and may use error-prone non-homologous end joining (NHEJ) to repair damaged DNA. Both the inability to complete S phase (because of stalled replication forks) and error-prone repair by NHEJ, can contribute to cell death.

Treatment with PARP inhibitors may selectively kill a subset of cancer cells with deficiencies in DNA repair pathways (e.g., inactivation of BRCA-1 and/or BRCA-2). For example, a tumor arising in a patient with a germline BRCA mutation can have a defective homologous recombination DNA repair pathway and would be increasingly dependent on BER, a pathway blocked by PARP inhibitors, for maintenance of genomic integrity. This mechanism of inducing death by use of PARP inhibitors to block one DNA repair pathway in tumors with pre-existing deficiencies in a complementary DNA repair pathways is referred to as synthetic lethality.

The therapeutic potential of PARP inhibitors is further expanded by the observation that PARP inhibitors not only have monotherapy activity in HR-deficient tumors, but are also effective in preclinical models in combination with other agents such as cisplatin, carboplatin, alkylating and methylating agents, radiation therapy, and topoisomerase I inhibitors. In contrast to the rationale for monotherapy in which PARP inhibition alone is sufficient for cell death in HR-deficient cancers (due to endogenous DNA damage), PARP may be required for repair of DNA damage induced by standard cytotoxic chemotherapy. In some cases, PARP may be required to release trapped topoisomerase I/irinotecan complexes from DNA. Temozolomide-induced DNA damage can be repaired by the BER pathway, which may require PARP to recruit repair proteins. Combination therapies that enhance or synergize the cancer therapy without significantly increasing toxicity can provide substantial benefit to cancer patients, including ovarian cancer patients.

PARP Inhibitors

PARP inhibitors can have activity against tumors with existing DNA repair defects, such as BRCA1 and BRCA2. Treatment with PARP inhibitors (e.g., PARP-1/2 inhibitors) may selectively kill a subset of cancer cell types by exploiting their deficiencies in DNA repair. Human cancers exhibit genomic instability and an increased mutation rate due to underlying defects in DNA repair. These deficiencies can render cancer cells more dependent on the remaining DNA repair pathways and targeting these pathways can have a much greater impact on the survival of the tumor cells than on normal cells.

In some embodiments, agents that inhibit PARP include agents that inhibit PARP-1 and/or PARP-2. In some embodiments, agent that inhibits PARP is selected from the group consisting of ABT-767, AZD 2461, BGB-290, BGP 15, CEP 9722, E7016, E7449, fluzoparib, INO1001, JPI 289, MP 124, niraparib, olaparib, ONO2231, rucaparib, SC 101914, talazoparib, veliparib, WW 46, and salts or derivatives thereof. In some embodiments, a PARP inhibitor is niraparib, olaparib, rucaparib, talazoparib, veliparib, or any combination thereof. In some embodiments, agent that inhibits PARP is selected from the group consisting of ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, a PARP inhibitor can be prepared as a pharmaceutically acceptable salt. In some embodiments, an agent that inhibits PARP is niraparib or a salt or derivative thereof. One of skill in the art will appreciate that such salt forms can exist as solvated or hydrated polymorphic forms.

In one aspect, pharmaceutical compositions provided herein in various embodiments comprise a PAPR inhibitor and a second agent. In some embodiments, the second agent is an angiogenesis inhibitor. In some embodiments, the angiogenesis inhibitor inhibits VEGF/VEGFR pathway. In some embodiments, the angiogenesis inhibitor is a VEGF and/or VEGFR inhibitor. In another aspect, methods provided herein comprise administering a PARP inhibitor and a second agent, wherein the second agent comprises an angiogenesis inhibitor.

Niraparib

Niraparib is an orally active and potent poly [ADP-ribose] polymerase (PARP) inhibitor. Niraparib and pharmaceutically acceptable salts thereof, are disclosed in International Publication No. WO2007/113596 and European Patent No. EP2007733B1; International Publication No. WO2008/084261 and U.S. Pat. No. 8,071,623; and International Publication No. WO2009/087381 and U.S. Pat. No. 8,436,185. Methods of making niraparib and pharmaceutically acceptable salts thereof are disclosed in International Publication Nos. WO2014/088983 and WO2014/088984. Methods to treat cancer with niraparib and pharmaceutically acceptable salts thereof are disclosed in U.S. Provisional Patent Application Nos. 62/356,461 and 62/402,427. The contents of each of the foregoing references are incorporated herein by reference in their entirety.

In some embodiments, the present invention relates to use of niraparib in combination with one or more additional pharmaceutically active agents affecting activity within the tumor microenvironment. Niraparib, (3S)-3-[4-{7-(aminocarbonyl)-2H-indazol-2-yl}phenyl]piperidine, is an orally available, potent, poly (adenosine diphosphate [ADP]-ribose) polymerase (PARP)-1 and -2 inhibitor. Niraparib has the following structure:

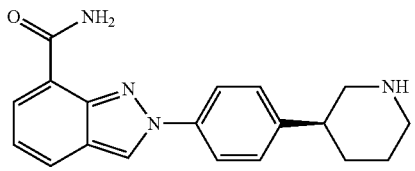 [SMILES: NC(=O)c1cccc2cn(-c3ccc([C@@H]4CCCNC4)cc3)nc12]

The empirical molecular formula for niraparib is $C_{26}H_{30}N_4O_5S$ and its molecular weight is 510.61. Niraparib tosylate monohydrate drug substance is a white to off-white, non-hygroscopic crystalline solid. Niraparib solubility is pH independent below the pKa of 9.95, with an aqueous free base solubility of 0.7 mg/mL to 1.1 mg/mL across the physiological pH range. See WO 2008/084261 (published on Jul. 17, 2008) and WO 2009/087381 (published Jul. 16, 2009), the entirety of each of which is hereby incorporated by reference. Niraparib can be prepared according to Scheme 1 of WO 2008/084261. As used herein, the term "niraparib" can mean any of the free base compound ((3S)-3-[4-{7-(aminocarbonyl)-2H-indazol-2-yl}phenyl]piperidine), a salt form, including pharmaceutically acceptable salts, of (3S)-3-[4-{7-(aminocarbonyl)-2H-indazol-2-yl}phenyl]piperidine (e.g., (3S)-3-[4-{7-(aminocarbonyl)-2H-indazol-2-yl}phenyl]piperidine tosylate), or a solvated or hydrated form thereof (e.g., (3S)-3-[4-{7-(aminocarbonyl)-2H-indazol-2-yl}phenyl]piperidine tosylate monohydrate). In some embodiments, such forms may be individually referred to as "niraparib free base", "niraparib tosylate" and "niraparib tosylate monohydrate", respectively. Unless otherwise specified, the term "niraparib" includes all forms of the compound (3S)-3-[4-{7-(aminocarbonyl)-2H-indazol-2-yl}phenyl]piperidine.

In some embodiments, niraparib can be prepared as a pharmaceutically acceptable salt. One of skill in the art will appreciate that such salt forms can exist as solvated or hydrated polymorphic forms. In some embodiments, niraparib is prepared in the form of a hydrate.

In certain embodiments, niraparib is prepared in the form of a tosylate salt. In some embodiments, niraparib is prepared in the form of a tosylate monohydrate.

The crystalline tosylate monohydrate salt of niraparib is being developed as a monotherapy agent for tumors with defects in the homologous recombination (HR) deoxyribonucleic acid (DNA) repair pathway and as a sensitizing agent in combination with cytotoxic agents and radiotherapy.

Provided herein are compositions containing niraparib or its pharmaceutically acceptable salts. The compositions may further include one or more additional active ingredients which impact efficacy of niraparib.

In some embodiments, the niraparib is a pharmaceutically acceptable salt of niraparib. In some embodiments, the pharmaceutically acceptable salt is niraparib tosylate monohydrate.

The formulation can comprise one or more components, including niraparib. The components can be combined to create granules that are then compressed to form tablets.

The niraparib may be present in the formulation as a pharmaceutically acceptable salt. For example, the niraparib can be niraparib tosylate monohydrate.

The niraparib formulations described herein can be administered and dosed in accordance with good medical practice, taking into account the clinical condition of the individual patient, the site and method of administration, scheduling of administration, and other factors known to medical practitioners. In human therapy, the dosage forms described herein deliver niraparib formulations that maintain a therapeutically effective amount of niraparib in plasma the while reducing the side effects associated with an elevated $C_{max}$ blood plasma level of niraparib.

Pharmaceutically Acceptable Salts

In some embodiments, the niraparib used in a composition disclosed herein is the form of a free base, pharmaceutically acceptable salt, prodrug, analog or complex. In some instances, the niraparib comprises the form of a pharmaceutically acceptable salt. In some embodiments, with respect to niraparib in a composition, a pharmaceutically acceptable salt includes, but is not limited to, 4-methylbenzenesulfonate salts, sulfate salts, benzenesulfate salts, fumarate salts, succinate salts, and stereoisomers or tautomers thereof. In some embodiments, with respect to niraparib in a composition, a pharmaceutically acceptable salt includes, but is not limited to, tosylate salts. In some embodiments, with respect to niraparib in a composition, a pharmaceutically acceptable salt includes, but is not limited to, tosylate monohydrate salts.

Additional Pharmaceutically Acceptable Excipients

In some aspects, the pharmaceutical composition disclosed herein further comprises one or more pharmaceutically acceptable excipients. In some embodiments, the one or more pharmaceutically acceptable excipient is present in an amount of about 0.1-99% by weight. Exemplary pharmaceutically acceptable excipients for the purposes of pharmaceutical compositions disclosed herein include, but are not limited to, binders, disintegrants, superdisintegrants, lubricants, diluents, fillers, flavors, glidants, sorbents, solubilizers, chelating agents, emulsifiers, thickening agents, dispersants, stabilizers, suspending agents, adsorbents, granulating agents, preservatives, buffers, coloring agents and sweeteners or combinations thereof. Examples of binders include microcrystalline cellulose, hydroxypropyl methylcellulose, carboxyvinyl polymer, polyvinylpyrrolidone, polyvinylpolypyrrolidone, carboxymethyl cellulose calcium, carboxymethylcellulose sodium, ceratonia, chitosan, cottonseed oil, dextrates, dextrin, ethylcellulose, gelatin, glucose, glyceryl behenate, galactomannan polysaccharide, hydroxyethyl cellulose, hydroxyethylmethyl cellulose, hydroxypropyl cellulose, hypromellose, inulin, lactose, magnesium aluminum silicate, maltodextrin, methylcellulose, poloxamer, polycarbophil, polydextrose, polyethylene glycol, polyethylene oxide, polymethacrylates, sodium alginate, sorbitol, starch, sucrose, sunflower oil, vegetable oil, tocofersolan, zein, or combinations thereof. Examples of disintegrants include hydroxypropyl methylcellulose (HPMC), low substituted hydroxypropyl cellulose (L-HPC), croscarmellose sodium, sodium starch glycolate, lactose, magnesium aluminum silicate, methylcellulose, polacrilin potassium, sodium alginate, starch, or combinations thereof. Examples of a lubricant include stearic acid, sodium stearyl fumarate, glyceryl behenate, calcium stearate, glycerin monostearate, glyceryl palmitostearate, magnesium lauryl sulfate, mineral oil, palmitic acid, myristic acid, poloxamer, polyethylene glycol, sodium benzoate, sodium chloride, sodium lauryl sulfate, talc, zinc stearate, potassium benzoate, magnesium stearate or combinations thereof. Examples of diluents include talc, ammonium alginate, calcium carbonate, calcium lactate, calcium phosphate, calcium silicate, calcium sulfate, cellulose, cellulose acetate, corn starch, dextrates, dextrin, dextrose, erythritol, ethylcellulose, fructose, fumaric acid, glyceryl palmitostearate, isomalt, kaolin, lactitol, lactose, magnesium carbonate, magnesium oxide, maltodextrin, maltose, mannitol, microcrystalline cellulose, polydextrose, polymethacrylates, simethicone, sodium alginate, sodium chloride, sorbitol, starch, sucrose, sulfobutylether β-cyclodextrin, tragacanth, trehalose, xylitol, or combinations thereof. In some embodiments, the pharmaceutically acceptable excipient is hydroxypropyl methylcellulose (HPMC). In some embodiments, the pharmaceutically acceptable excipient is low substituted hydroxypropyl cellulose (L-HPC). In some embodiments, the pharmaceutically acceptable excipient is lactose. In some embodiments, the pharmaceutically acceptable excipient is lactose monohydrate. In some embodiments, the pharmaceutically acceptable excipient is magnesium stearate. In some embodiments, the pharmaceutically acceptable excipient is lactose monohydrate and magnesium stearate.

Various useful fillers or diluents include, but are not limited to calcium carbonate (Barcroft™, MagGran™, Millicarb™, Pharma-Carb™, Precarb™, Sturcal™, Vivapres Ca™), calcium phosphate, dibasic anhydrous (Emcompress Anhydrous™, Fujicalin™), calcium phosphate, dibasic dihydrate (Calstar™, Di-Cafos™, Emcompress™), calcium phosphate tribasic (Tri-Cafos™, TRI-TAB™), calcium sulphate (Destab™, Drierite™, Snow White™, Cal-Tab™, Compactrol™), cellulose powdered (Arbocel™, Elcema™, Sanacet™), silicified microcrystailine cellulose, cellulose acetate, compressible sugar (Di-Pac™), confectioner's sugar, dextrates (Candex™, Emdex™), dextrin (Avedex™, Caloreen™, Primogran W™), dextrose (Caridex™, Dextrofin™, Tab fine D-IOO™), fructose (Fructofin™, Krystar™), kaolin (Lion™, Sim 90™), lactitol (Finlac DC™, Finlac MCX™), lactose (Anhydrox™, CapsuLac™, Fast-Flo™, FlowLac™, GranuLac™, InhaLac™, Lactochem™, Lactohaie™, Lactopress™, Microfme™, Microtose™, Pharmatose™, Prisma Lac™, Respitose™, SacheLac™, SorboLac™, Super-Tab™, Tablettose™, Wyndale™, Zeparox™), lactose monohydrate, magnesium carbonate, magnesium oxide (MagGran MO™), maltodextrin (C*Dry MD™, Lycatab DSH™, Maldex™, Maitagran™, Maltrin™, Maltrin QD™, Paselli MD 10 PH™, Star-Dri™), maltose (Advantose 100™), mannitol (Mannogem™, Pearlitol™), microcrystalline cellulose (Avicel PH™, Celex™, Celphere™, Ceolus KG™, Emcocel™, Pharmacel™, Tabulose™, Vivapur™), polydextrose (Litesse™), simethicone (Dow Corning Q7-2243 LVA™, Cow Coming Q7-2587™, Sentry Simethicone™), sodium alginate (Keltone™, Protanal™), sodium chloride (Alberger™), sorbitol (Liponec 70-NC™, Liponic 76-NCv, Meritol™, Neosorb™, Sorbitol Instant™, Sorbogem™), starch (Flufiex W™, Instant Pure-Cote™, Melojei™, Meritena Paygel 55™, Perfectamyl D6PH™, Pure-Cote™, Pure-Dent™, Pure-Gel™, Pure-Set™, Purity 21™, Purity 826™, Tablet White™), pregelatinized starch, sucrose, trehalose and xylitol, or mixtures thereof.

Various useful disintegrants include, but are not limited to, alginic acid (Protacid™, Satialgine H8™), calcium phosphate, tribasic (TRI-TAB™), carboxymethylcellulose calcium (ECG 505™), carboxymethylcellulose sodium (Akucell™, Finnfix™, Nymcel Tylose CB™), colloidal silicon dioxide (Aerosil™, Cab-O-Sil™, Wacker HDK™), croscarmellose sodium (Ac-Di-Sol™, Pharmacel XL™, Primellose™, Solutab™, Vivasol™), crospovidone (Collison CL™, Collison CL-M™, Polyplasdone XL™), docusate sodium, guar gum (Meyprodor™, Meyprofm™, Meyproguar™), low substituted hydroxypropyl cellulose, magnesium aluminum silicate (Magnabite™, Neusilin™, Pharmsorb™, Veegum™), methylcellulose (Methocel™, Metolose™), microcrystalline cellulose (Avicel PH™, Ceoius KG™, Emcoel™, Ethispheres™, Fibrocel™, Pharmacel™, Vivapur™), povidone (Collison™, Plasdone™) sodium alginate (Kelcosol™, Ketone™, ProtanalrM), sodium starch glycolate, polacrilin potassium (Amberlite IRP88™), silicified microcrystalline cellulose (ProSotv™), starch (Aytex P™, Fluftex W™, Melojel™, Meritena™, Paygel 55™, Perfectamyl D6PH™, Pure-Bind™, Pure-Cote™, Pure-Dent™, Purity 21™, Purity 826™, Tablet White™) or pre-gelatinized starch (Lycatab PGS™, Merigel™, National 78-1551™, Pharma-Gel™, Prejel™, Sepistab ST 200™, Spress B820™, Starch 1500 G™, Tablitz™, Unipure LD™), or mixtures thereof.

Various useful lubricants include, but are not limited to, calcium stearate (HyQual™), glycerine monostearate (Imwitor™ 191 and 900, Kessco GMS5™, 450 and 600, Myvaplex 600P™, Myvatex™, Rita GMS™, Stepan GMS™, Tegin™, Tegin™ 503 and 515, Tegin 4100™, Tegin M™, Unimate GMS™), glyceryl behenate (Compritol 888 ATO™), glyceryl palmitostearate (Precirol ATO 5™), hydrogenated castor oil (Castorwax MP 80™, Croduret™, Cutina HR™, Fancol™, Simulsol 1293™), hydrogenated vegetable oil 0 type I (Sterotex™, Dynasan P60™, Hydrocote™, Lipovol HS-K™, Sterotex HM™), magnesium lauryl sulphate, magnesium stearate, medium-chain triglycerides (Captex 300™, Labrafac CC™, Miglyol 810™, Neobee M5™, Nesatol™, Waglinol 3/9280™), poloxamer (Pluronic™, Synperonic™), polyethylene 5 glycol (Carbowax Sentry™, Lipo™, Lipoxol™, Lutrol E™, Pluriol E™), sodium benzoate (Antimol™), sodium chloride, sodium lauryl sulphate (Elfan 240™, Texapon Kl 2P™), sodium stearyl fumarate (Pruv™), stearic acid (Hystrene™, Industrene™, Kortacid 1895™, Pristerene™), talc (Altaic™, Luzenac™, Luzenac Pharma™, Magsil Osmanthus™, 0 Magsil Star™, Superiore™), sucrose stearate (Surfhope SE Pharma D-1803 F™) and zinc stearate (HyQual™) or mixtures thereof. Examples of suitable lubricants include, but are not limited to, magnesium stearate, calcium stearate, zinc stearate, stearic acid, talc, glyceryl behenate, polyethylene glycol, polyethylene oxide polymers, sodium lauryl sulfate, magnesium lauryl sulfate, sodium oleate, sodium stearyl fumarate, DL-leucine, colloidal silica, and others as known in the art. In some embodiments a lubricant is magnesium stearate.

Various useful glidants include, but are not limited to, tribasic calcium phosphate (TRI-TAB™), calcium silicate, cellulose, powdered (Sanacel™, Solka-Floe™), colloidal silicon dioxide (Aerosil™, Cab-O-Sil M-5P™, Wacker HDK™), magnesium silicate, magnesium trisilicate, starch (Melojel™, Meritena™, Paygel 55™, Perfectamyl D6PH™, Pure-Bind™, Pure-Cote™, Pure-Dent™, Pure-Gel™, Pure-Set™, Purity 21™, Purity 826™, Tablet White™) and talc (Luzenac Pharma™, Magsil Osmanthus™, Magsil Star™, Superiore™), or mixtures thereof.

Pharmaceutically acceptable surfactants include, but are limited to both non-ionic and ionic surfactants suitable for use in pharmaceutical dosage forms. Ionic surfactants may include one or more of anionic, cationic or zwitterionic surfactants. Various useful surfactants include, but are not limited to, sodium lauryl sulfate, monooleate, monolaurate, monopalmitate, monostearate or another ester of olyoxyethylene sorbitane, sodium dioctylsulfosuccinate (DOSS), lecithin, stearyic alcohol, cetostearylic alcohol, cholesterol, polyoxyethylene ricin oil, polyoxyethylene fatty acid glycerides, poloxamer, or any other commercially available co-processed surfactant like SEPITRAP® 80 or SEPITRAP® 4000 and mixtures thereof.

Angiogenesis

Angiogenesis refers to the generation of new blood vessels into a tissue or organ. Under normal physiological conditions, humans or animals only undergo angiogenesis in very specific restricted situations. For example, angiogenesis is normally observed in wound healing, fetal and embryonal development and formation of the corpus luteum, endometrium and placenta. The control of angiogenesis is a highly regulated system of pro-angiogenic factors and anti-angiogenic factors.

The control of angiogenesis can be altered in certain disease states and, in many cases, the pathological damage associated with the disease is related to uncontrolled angiogenesis. Both controlled and uncontrolled angiogenesis can proceed in a similar manner. Endothelial cells and pericytes, surrounded by a basement membrane, can form capillary blood vessels. Angiogenesis can begin with the erosion of the basement membrane by enzymes released by endothelial cells and leukocytes. The endothelial cells, which line the lumen of blood vessels, then protrude through the basement membrane. Angiogenic stimulants, such as pro-angiogenic factors, induce the endothelial cells to migrate through the eroded basement membrane. The migrating cells form a "sprout" off the parent blood vessel, where the endothelial cells undergo mitosis and proliferate. This process can refer to "vessel sprouting". The endothelial sprouts merge with each other to form capillary loops, creating the new blood vessel. In the disease state, prevention of angiogenesis could avert the damage caused by the invasion of the new microvascular system. The angiogenesis signaling pathway can primarily be regulated through tyrosine kinase receptors, therefore, the controlling mechanisms of angiogenesis can be the paracrine regulation of tyrosine kinase receptors, primarily on endothelial cells.

Pro-angiogenic factors can include fibroblast growth factors (FGF) and vascular endothelial growth factors (VEGF)

which function as endothelial cell mitogens. Besides FGFs and VEGFs, the VEGF receptors (VEGF-R1, -R2 and -R3), and placental growth factors (PlGF) are also pro-angiogenic factors. In addition, several factors, such as the angiopoietins, ephrins, leptin and chemokines, can play a role in angiogenesis.

The fibroblast growth factor (FGF) family with its prototype members FGF-1 (acidic FGF, or aFGF) and FGF-2 (basic FGF, or bFGF) consists of at least 22 known members, including FGF1-14, FGF15/19 (FGF15 is the mouse ortholog of human FGF19, and there is no human FGF15), FGF18-23. Most are single-chain peptides of 16-18 kDa and display high affinity to heparin and heparan sulfate. In general, FGFs can stimulate a variety of cellular functions by binding to cell surface FGF-receptors in the presence of heparin proteoglycans. The FGF-receptor family is composed of seven members, and all the receptor proteins are single-chain receptor tyrosine kinases that become activated through autophosphorylation induced by a mechanism of FGF-mediated receptor dimerization. Receptor activation can give rise to a signal transduction cascade that leads to gene activation and diverse biological responses, including cell differentiation, proliferation, and matrix dissolution, thus initiating a process of mitogenic activity critical for the growth of endothelial cells, fibroblasts, and smooth muscle cells. FGF-1, unique among all 22 members of the FGF family, can bind to all seven FGF-receptor subtypes, making it the broadest-acting member of the FGF family, and a potent mitogen for the diverse cell types needed to mount an angiogenic response in damaged (hypoxic) tissues, where upregulation of FGF-receptors occurs. FGF-1 stimulates the proliferation and differentiation of all cell types necessary for building an arterial vessel, including endothelial cells and smooth muscle cells; this fact distinguishes FGF-1 from other pro-angiogenic growth factors, such as vascular endothelial growth factor (VEGF), which primarily drives the formation of new capillaries.

Vascular endothelial growth factor (VEGF) can be another contributor to angiogenesis, increasing the number of capillaries in a given network. Initial in vitro studies demonstrated bovine capillary endothelial cells can proliferate and show signs of tube structures upon stimulation by VEGF and bFGF. In vitro studies have demonstrated that VEGF can be a potent stimulator of angiogenesis because, in the presence of this growth factor, plated endothelial cells will proliferate and migrate, eventually forming tube structures resembling capillaries. VEGF can cause a massive signaling cascade in endothelial cells. Binding to VEGF receptor-2 (VEGFR-2) can start a tyrosine kinase signaling cascade that stimulates the production of factors that variously stimulate vessel permeability (eNOS, producing NO), proliferation/survival (bFGF), migration (ICAMs/VCAMs/MMPs) and finally differentiation into mature blood vessels. Mechanically, VEGF can be upregulated with muscle contractions as a result of increased blood flow to affected areas. The increased flow can also cause a large increase in the mRNA production of VEGF receptors 1 and 2. The increase in receptor production indicates that muscle contractions could cause upregulation of the signaling cascade relating to angiogenesis. As part of the angiogenic signaling cascade, NO can be a contributor to the angiogenic response because inhibition of NO can reduce the effects of pro-angiogenic growth factors.

The vascular endothelial growth factor (VEGF) and its receptor (VEGFR) can play roles not only in physiological but also in most pathological angiogenesis, such as cancer. VEGF belongs to the platelet-derived growth factor (PDGF) supergene family characterized by 8 conserved cysteines and functions as a homodimer structure. VEGF family protein can include VEGF-A, VEGF-B, VEGF-C, VEGF-D, PlGF (placental growth factor), VEGF-E (Orf-VEGF), Trimeresurus flavoviridis svVEGF. VEGF-A can regulate angiogenesis and vascular permeability by activating 2 receptors, VEGFR-1 (Flt-1) and VEGFR-2 (KDR/Flk1 in mice). On the other hand, VEGF-C/VEGF-D and their receptor, VEGFR-3 (Flt-4), may mainly regulate lymphangiogenesis. The VEGF family includes other variants, one of which is the virally encoded VEGF-E and another is specifically expressed in the venom of the habu snake (Trimeresurus flavoviridis). VEGFRs are distantly related to the PDGFR family; however, they are unique with respect to their structure and signaling system. Unlike members of the PDGFR family that can stimulate the PI3K-Akt pathway toward cell proliferation, VEGFR-2, the signal transducer for angiogenesis, may utilize the PLCγ-PKC-MAPK pathway for signaling. The VEGF-VEGFR system can be targeted for anti-angiogenic therapy in cancer and can also be targeted for pro-angiogenic therapy in the treatment of neuronal degeneration and ischemic diseases.

Notch signaling can be involved in tumor pathologic angiogenesis. Whole transcriptome sequencing revealed that Hey1, a Notch target, can play a fundamental role in neoplastic vasculature development. Inhibition of Notch signaling can decrease the production of new blood vessels. Notch1 in connection with VEGF-A can have a significant prognostic impact, indicating that Notch pathway can increase the possibility of metastasis and poor outcome through regulating tumor angiogenesis via crosstalk with VEGF-A in cancer such as lung cancer. Blockade of the DLL4-Notch pathway may be associated with decreased angiogenesis and tumor growth. Combined targeting treatments of DLL4 and vascular endothelial growth factor (VEGF) signaling pathway can result in enhanced tumor growth inhibition and a marked decrease in tumor perfusion. Targeting Notch signaling may benefit patients with cancer.

Other pro-angiogenic factors include angiogenin, angiopoietins (Ang1 and Ang2), angiopoietin receptors Tie-1 and Tie-2, matrix metalloproteinase (MMP), delta-like ligand (Dll4), Class 3 Semaphorins (SEMA3s), ephrins, leptin, transforming growth factor-3, and chemokines.

In some embodiments, the methods provided herein comprise administering a PARP inhibitor and an angiogenesis inhibitor. In some embodiments, the pharmaceutical compositions or kits provided herein comprise a PARP inhibitor and an angiogenesis inhibitor. In some embodiments, the angiogenesis inhibitor inhibits a pro-angiogenic factor, wherein the pro-angiogenic factor comprises FGF1-14, FGF15/19, FGF18-23, PDGF, VEGF-A, VEGF-B, VEGF-C, VEGF-D, PlGF (placental growth factor), VEGF-E (Orf-VEGF), Trimeresurus flavoviridis svVEGF, VEGFR-1, VEGFR-2, VEGFR-3, angiogenin, angiopoietin-1, angiopoietin-2, Tie-1, Tie-2, MMP, Dll4, SEMA3s, ephrins, leptin, chemokines, transforming growth factor-β (TGF-β) or any combination thereof.

Angiogenesis Inhibition

Persistent, unregulated angiogenesis can occur in a multiplicity of disease states, tumor metastasis and abnormal growth by endothelial cells and can support the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

Tumor cells release various pro-angiogenic factors (e.g., angiogenin, vascular endothelial growth factor (VEGF), fibroblast growth factor (FGF), and transforming growth factor-β (TGF-β). These can stimulate endothelial cell proliferation, migration and invasion resulting in new vascular structures sprouting from nearby blood vessels. Cell adhesion molecules, such as integrins, can be critical to the attachment and migration of endothelial cells to the extracellular matrix.

Tumor growth and metastasis depend on new growth in the vascular network supporting the tumor. VEGF can be secreted by tumor cells and act on endothelial cells to stimulate angiogenesis during tumor growth. Angiogenesis inhibitors such as VEGF inhibitors (e.g., bevacizumab) can increase numbers of antigen-specific T cells in solid tumors and enhance the efficiency of immunotherapy. For example, combination treatment of bevacizumab with either atezolizumab (inhibiting PD-L1) or ipilimumab (inhibiting CTLA-4) increases the number of intratumoral CD8+ cells. Other examples of VEGF inhibitors which may activate antigen-specific T cells in tumor microenvironments include pazopanib, sunitinib, sorafenib, axitinib, ponatinib, regorafenib, cabozantinib, vandetanib, ramucirumab, lenvatinib and ziv-aflibercept.

Angiogenesis can be prominent in solid tumor formation and metastasis. Angiogenic factors have been found associated with several solid tumors such as rhabdomyosarcomas, retinoblastoma, Ewing's sarcoma, neuroblastoma, and osteosarcoma. A tumor cannot expand without a blood supply to provide nutrients and remove cellular wastes. Tumors in which angiogenesis may be important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

Angiogenesis can be associated with blood-borne tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. Angiogenesis can play a role in the abnormalities in the bone marrow that give rise to leukemia-like tumors.

Angiogenesis may be important in two stages of tumor metastasis. The first stage can be in the vascularization of the tumor which allows tumor cells to enter the blood stream and to circulate throughout the body. After the tumor cells have left the primary site, and have settled into the secondary, metastasis site, angiogenesis occurs before the new tumor can grow and expand. Therefore, prevention of angiogenesis could lead to the prevention of metastasis of tumors and possibly contain the neoplastic growth at the primary site.

Angiogenesis can be a prognostic indicator for breast cancer. The amount of neovascularization found in the primary tumor can be determined by counting the microvessel density in the area of the most intense neovascularization in invasive breast carcinoma. A high level of microvessel density can correlate with tumor recurrence. Control of angiogenesis by therapeutic means could possibly lead to cessation of the recurrence of the tumors.

Angiogenesis can also be involved in normal physiological processes such as reproduction and wound healing. Angiogenesis may be an important step in ovulation and also in implantation of the blastula after fertilization. Prevention of angiogenesis could be used to induce amenorrhea, to block ovulation or to prevent implantation by the blastula. In wound healing, excessive repair or fibroplasia can be a detrimental side effect of surgical procedures and may be caused or exacerbated by angiogenesis. Adhesions can be a frequent complication of surgery and lead to problems such as small bowel obstruction.

Various compounds can be used to prevent angiogenesis. For example, angiogenesis inhibitors can include protamine, heparin and steroids. Steroids, such as tetrahydrocortisol, which lack gluco and mineral corticoid activity, can inhibit angiogenesis.

Other factors found endogenously in animals, such as a 4 kDa glycoprotein from bovine vitreous humor and a cartilage derived factor, can be used to inhibit angiogenesis. Cellular factors such as interferon can inhibit angiogenesis. For example, interferon α or human interferon β can inhibit tumor-induced angiogenesis in mouse dermis stimulated by human neoplastic cells. Human recombinant interferon (alpha/A) can also inhibit angiogenesis.

Other agents which can be used to inhibit angiogenesis include ascorbic acid ethers and related compounds. Sulfated polysaccharide DS 4152 can also show angiogenic inhibition. A fungal product, fumagillin, can be a potent angiostatic agent in vitro. The compound is toxic in vivo, but a synthetic derivative, AGM 12470, can be used in vivo to treat collagen II arthritis. Fumagillin and O-substituted fumagillin derivatives are disclosed in EPO Publication Nos. 0325199A2 and 0357061A1.

Angiogenesis inhibitors may reduce the production of a pro-angiogenic factor, inhibit an interaction between a pro-angiogenic factor and a pro-angiogenic receptor, inhibit a function of a pro-angiogenic factor, inhibit a function of a pro-angiogenic factor receptor, reduce of blood flow by disruption of blood vessels, or inhibit vessel sprouting. Angiogenesis inhibitors can target a VEGF/VEGFR pathway, or a DLL4/Notch signaling pathway.

In some embodiments, the methods provided herein comprise administering a PARP inhibitor and an angiogenesis inhibitor. In some embodiments, the angiogenesis inhibitor reduces the production of a pro-angiogenic factor, inhibits an interaction between a pro-angiogenic factor and a pro-angiogenic receptor, inhibits a function of a pro-angiogenic factor, inhibits a function of a pro-angiogenic factor receptor, reduces of blood flow by disruption of blood vessels, inhibits vessel sprouting, or any combinations thereof. In some embodiments, the angiogenesis inhibitor is selected from the group consisting of bevacizumab, itraconazole, carboxyamidotriazole, TNP-470, fumagillin, CM101, IL-12, platelet factor-4, suramin, SU5416, thrombospondin, angiostatic steroids, heparin, cartilage-derived angiogenesis inhibitory factor (e.g. peptide troponin I and chondromodulin I), matrix metalloproteinase inhibitor, angiostatin, endostatin, 2-methoxyestradiol, tecogalan, tetrathiomolybdate, thrombospondin, thalidomide, prolactin, αvβ3 inhibitor, lenalidomide, linomide, ramucirumab, tasquinimod, ranibizumab, sorafenib, sunitinib, pazopanib, everolimus, tissue inhibitors of metalloproteases (TIMP1 and TIMP2), bFGF soluble receptor, transforming growth factor beta, interferon alpha, interferon beta, soluble KDR and FLT-1 receptors, placental proliferin-related protein, pazopanib, sunitinib, sorafenib, axitinib, ponatinib, cabozantinib, regorafenib, vandetanib, lenvatinib, semaxanib, SU6668, vatalanib, tivozanib, cediranib, protamine, heparin, steroids, ascorbic acid ethers, sulfated polysaccharide DS 4152, fumagillin, AGM 12470, neovastat, RO4929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, OMP-21M18, navicixizumab (OMP-305B83), Flt$_{2\text{-}11}$, CBO-P11, Je-11, V1, and any combination thereof.

In some embodiments, the angiogenesis inhibitor induces homologous recombinant (HR) deficiency. In some embodiments, the angiogenesis inhibitor induces hypoxia. In some embodiments, the angiogenesis inhibitor induces homologous recombinant (HR) deficiency by hypoxia. In some embodiments, the angiogenesis inhibitor comprises a VEGF inhibitor, a VEGFR inhibitor, or a combination thereof.

In some embodiments, the PARP inhibitors of the present disclosure can be used in combination with an agent that inhibits a DLL4/Notch signaling pathway. In some embodiments, the agent inhibiting a DLL4/Notch signaling pathway is a gamma-secretase inhibitor (GSI), a siRNA, or a monoclonal antibody against a Notch receptor or ligand. In some embodiments, the agent inhibiting a DLL4/Notch signaling pathway is selected from the group consisting of R04929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, OMP-21M18, navicixizumab (OMP-305B83), and any combination thereof.

In some embodiments, the PARP inhibitors of the present disclosure can be used in combination with an agent that inhibits a VEGF/VEGFR pathway. In some embodiments, the agent inhibits a VEGF family protein or a VEGFR family protein. In some embodiments, the agent inhibits VEGF-A, VEGF-B, VEGF-C, VEGF-D, PlGF (placental growth factor), VEGF-E (Orf-VEGF), *Trimeresurus flavoviridis* svVEGF, or any combination thereof. In some embodiments, the agent inhibits VEGFR-1, VEGFR-2, VEGFR-3, or any combination thereof.

In some embodiment, the PARP inhibitors of the present disclosure can be used in combination with a VEGF inhibitor or a VEGFR inhibitor such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab). In some embodiments, the VEGF inhibitor or the VEGFR inhibitor is a small organic or inorganic molecule. In some embodiments, the VEGF inhibitor or the VEGFR inhibitor is an antibody or a fragment thereof. In some embodiments, the VEGFR inhibitor is a tyrosine kinase inhibitor. In some embodiments, the VEGF inhibitor or VEGFR inhibitor is selected from the group consisting of bevacizumab, ranibizumab, OPT-302, ziv-aflibercept, pazopanib, sunitinib, sorafenib, axitinib, ponatinib, cabozantinib, regorafenib, vandetanib, lenvatinib, semaxanib, SU6668, vatalanib, tivozanib, cediranib, ramucirumab, Flt$_{2\text{-}11}$, CBO-P11, Je-11, V1, and any combination thereof.

Therapeutic Agents

Therapeutic agents disclosed herein can be a small organic or inorganic molecule; a saccharine; an oligosaccharide; a polysaccharide; a carbohydrate; a peptide; a protein; a protein fragment; a peptide analog; a peptide derivative; a lipid; an antibody; an antibody fragment; a peptidomimetic; a nucleic acid; a nucleic acid analog; a nucleic acid derivative; an extract made from biological materials; a naturally occurring or synthetic composition; a metal; or a toxin. In some embodiments, the therapeutic agent is a small organic or inorganic molecule. In some embodiments, the therapeutic agent is an antibody or a fragment thereof.

In various embodiments, the methods or compositions provided herein comprise a first agent and a second agent. In some embodiments, the first agent is a PARP inhibitor. In some embodiments, the first agent inhibits PARP1, PARP2, or both. In some embodiments, the first agent is selected from the group consisting of ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, the first agent is niraparib, or salts or derivatives thereof. In some embodiments, the second agent is an angiogenesis inhibitor. In some embodiments, the second agent is an angiogenesis inhibitor, wherein the angiogenesis inhibitor is selected from the group consisting of bevacizumab, itraconazole, carboxyamidotriazole, TNP-470, fumagillin, CM101, IL-12, platelet factor-4, suramin, SU5416, thrombospondin, angiostatic steroids, heparin, cartilage-derived angiogenesis inhibitory factor, matrix metalloproteinase inhibitor, angiostatin, endostatin, 2-methoxyestradiol, tecogalan, tetrathiomolybdate, thrombospondin, thalidomide, prolactin, αVβ3 inhibitor, lenalidomide, linomide, ramucirumab, tasquinimod, ranibizumab, sorafenib, sunitinib, pazopanib, everolimus, tissue inhibitors of metalloproteases (TIMP1 and TIMP2), bFGF soluble receptor, transforming growth factor beta, interferon alpha, soluble KDR and FLT-1 receptors, placental proliferin-related protein, pazopanib, sunitinib, sorafenib, axitinib, ponatinib, cabozantinib, regorafenib, vandetanib, lenvatinib, semaxanib, SU6668, vatalanib, tivozanib, cediranib, protamine, heparin, steroids, ascorbic acid ethers, sulfated polysaccharide DS 4152, fumagillin, AGM 12470, neovastat, R04929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, OMP-21M18, navicixizumab (OMP-305B83), Flt2-11, CBO-P11, Je-11, V1, and any combination thereof. In some embodiments, the second agent is an angiogenesis inhibitor, wherein the angiogenesis inhibitor inhibits a VEGF/VEGFR pathway. In some embodiments, the second agent is a VEGF inhibitor. In some embodiments, the second agent is a VEGFR inhibitor. In some embodiments, the angiogenesis inhibitor inhibits a DLL4/Notch signaling pathway.

In some embodiments, the methods and compositions disclosed herein further comprise a third agent. In some embodiments, the third agent comprises an anti-immunosuppressive agent or immunostimulatory agent, a chemotherapeutic agent, or a combination thereof. In some embodiments, the anti-immunosuppressive agent or immunostimulatory agent comprises an anti-PD-1 agent, an anti-PD-L1 agent, an anti-CTLA4 agent, an anti-TIM-3 agent, an anti-LAG-3 agent, a GITR (glucocorticoid-induced TNFR-related protein) stimulating agent, an anti-IDO agent, an anti-ICOS agent, an anti-OX40 agent, an anti-CSF1R agent, a chemokine signaling agent, a cytokine signal stimulating agent, or any combination thereof. In some embodiments, the anti-PD-1 agent is selected from the group consisting of pembrolizumab, nivolumab, PDR001, REGN2810 (SAR-439684), BGB-A317, BI 754091, IBI308, INCSHR-1210, JNJ-63723283, JS-001, MEDI0680 (AMP-514), MGA-012, PF-06801591, REGN-2810, TSR-042, atezolizumab, avelumab, CX-072, durvalumab, FAZ053, LY3300054, PD-L1 millamolecule, and any combinations thereof. In some embodiments, the anti-PD-L1 agent is selected from the group consisting of atezolizumab, durvalumab, avelumab, LY3300054, and any combinations thereof. In some embodiments, the GITR stimulating agent is selected from the group consisting of DTA-1, mGITRL, pGITRL, and any combinations thereof. In some embodiments, the anti-CTLA4 agent is selected from the group consisting of ipilimumab, tremelimumab, and a combination thereof. In some embodiments, the third agent is an anti-immunosuppressive agent or immunostimulatory agent selected from the group consisting of a flavonoid (e.g., flavonoid glycoside), lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin. In some embodiments, the third agent is a chemotherapeutic agent selected from the group consisting of aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, vinorelbine, and any combinations thereof.

In some embodiments, provided herein are compositions, wherein the compositions comprise one or more therapeutic agents disclosed herein. The composition can mean a pharmaceutical composition, and is intended to encompass a therapeutic agent (e.g. drug product) comprising niraparib or its pharmaceutically acceptable salts, esters, solvates, polymorphs, stereoisomers or mixtures thereof, and the other inert ingredient(s) (pharmaceutically acceptable excipients). Such pharmaceutical compositions are synonymous with "formulation" and "dosage form". Pharmaceutical composition of the present disclosure include, but is not limited to, granules, tablets (single layered tablets, multilayered tablets, mini tablets, bioadhesive tablets, caplets, matrix tablets, tablet within a tablet, mucoadhesive tablets, modified release tablets, orally disintegrating tablets, pulsatile release tablets, timed release tablets, delayed release, controlled release, extended release and sustained release tablets), capsules (hard and soft or liquid filled soft gelatin capsules), pills, troches, sachets, powders, microcapsules, minitablets, tablets in capsules and microspheres, matrix composition and the like. In some embodiments, the pharmaceutical composition refers to capsules. In some embodiments, the pharmaceutical composition refers to hard gelatin capsules or HPMC based capsules. In some embodiments, the pharmaceutical composition refers to hard gelatin capsules.

Combination Therapies

As disclosed herein one or more therapeutic agents can be combined to treat a disease or condition. Combination therapy can provide many benefits including synergistic effect. The benefits of synergistic effect can include reducing the dose of each therapeutic agent in the combination therapy, and/or reducing the side effect associated with higher doses.

In one aspect, the present disclosure provides a method of treating a subject with a disease or condition comprising administering to the subject a first agent that inhibits poly [ADP-ribose] polymerase (PARP); and a second agent, wherein the second agent comprises an angiogenesis inhibitor.

In another aspect, the present disclosure provides a method of preventing a tumor cell growth in a subject with a disease or condition comprising administering to the subject a first agent that inhibits poly [ADP-ribose] polymerase (PARP); and a second agent, wherein the second agent comprises an angiogenesis inhibitor.

In a third aspect, the present disclosure provides a method of preventing tumor metastasis in a subject with a disease or condition comprising administering to the subject a first agent that inhibits poly [ADP-ribose] polymerase (PARP); and a second agent, wherein the second agent comprises an angiogenesis inhibitor.

In a fourth aspect, the present disclosure provides a method of inducing an immune response in a subject with a disease or condition comprising administering to the subject a first agent that inhibits poly [ADP-ribose] polymerase (PARP); and a second agent, wherein the second agent comprises an angiogenesis inhibitor.

In a fifth aspect, the present disclosure provides a method of enhancing an immune response in a subject with a disease or condition comprising administering to the subject a first agent that inhibits poly [ADP-ribose] polymerase (PARP); and a second agent, wherein the second agent comprises an angiogenesis inhibitor.

The PARP inhibitors and angiogenesis inhibitors are disclosed herein, and different combinations of PARP inhibitors and angiogenesis inhibitors can be used in the combination therapy. Exemplary combinations include, but are not limited to, niraparib and bevacizumab, or niraparib and cabozantinib. Niraparib is an orally available and selective poly (ADP-ribose) polymerase (PARP)-1/-2 inhibitor approved for maintenance treatment of patients with recurrent epithelial ovarian, fallopian tube, or primary peritoneal cancer in complete or partial response to platinum-based chemotherapy. It is currently being developed in ovarian and other cancers as monotherapy or in combination with other anti-cancer therapies. Bevacizumab (Avastin®) is a recombinant humanized monoclonal antibody that can block angiogenesis and inhibit vascular endothelial growth factor A (VEGF-A). It is approved as treatment for many cancer types including colorectal cancer, lung cancer, kidney cancer, and ovarian cancer. Cabozantinib (COMETRIQ®) is a small molecule inhibitor of the tyrosine kinase VEGFR2. It also inhibits c-Met, AXL and RET. Cabozantinib is approved for the treatment of medullary thyroid cancer and kidney cancer.

In some embodiments, the first agent is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; a toxin; or any combination thereof. In some embodiments, the first agent is a small molecule. In some embodiments, the first agent is selected from the group consisting of: ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, the first agent is selected from the group consisting of: niraparib, olaparib, rucaparib, talazoparib, veliparib, and salts or derivatives thereof. In some embodiments, the first agent is niraparib or a pharmaceutically acceptable salt or derivative thereof.

In some embodiments, the angiogenesis inhibitor reduces the production of a pro-angiogenic factor, inhibits an interaction between a pro-angiogenic factor and a pro-angiogenic receptor, inhibits a function of a pro-angiogenic factor, inhibits a function of a pro-angiogenic factor receptor, reduces of blood flow by disruption of blood vessels, inhibits vessel sprouting, or any combinations thereof. In some embodiments, the pro-angiogenic factor comprises FGFT-14, FGF 15/19, FGF18-23, PDGF, VEGF-A, VEGF-B, VEGF-C, VEGF-D, PlGF (placental growth factor), VEGF-E (Orf-VEGF), Trimeresurus flavoviridis svVEGF, VEGFR-1, VEGFR-2, VEGFR-3, angiogenin, angiopoietin-1, angiopoietin-2, Tie-1, Tie-2, MMP, Dll4, SEMA3s, ephrins, leptin, chemokines, transforming growth factor-β (TGF-β), or any combination thereof. In some embodiments, the angiogenesis inhibitor is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; a toxin; or any combination thereof. In some embodiments, the angiogenesis inhibitor is selected from the group consisting of bevacizumab, itraconazole, carboxyamidotriazole, TNP-470, fumagillin, CM101, IL-12, platelet factor-4, suramin, SU5416, thrombospondin, angiostatic steroids, heparin, cartilage-derived angiogenesis inhibitory factor (e.g. peptide troponin I and chondromodulin I), matrix metalloproteinase inhibitor, angiostatin, endostatin, 2-methoxyestradiol, tecogalan, tetrathiomolybdate, thrombospondin, thalidomide, prolactin, αVβ3 inhibitor, lenalidomide, linomide, ramucirumab, tasquinimod, ranibizumab, sorafenib, sunitinib, pazopanib, everolimus, tissue inhibitors of metalloproteases (TIMP1 and TIMP2), bFGF soluble receptor, transforming growth factor beta, interferon alpha, soluble KDR and FLT-1 receptors, placental proliferin-related protein, and any combination thereof. In some embodiments, the angiogenesis inhibitor is selected from the group consisting of bevacizumab, itraconazole, carboxyamidotriazole, TNP-470, fumagillin, CM101, IL-12, platelet factor-4, suramin, SU5416, thrombospondin, angiostatic steroids, heparin, cartilage-derived angiogenesis inhibitory factor, matrix metalloproteinase inhibitor, angiostatin, endostatin, 2-methoxyestradiol, tecogalan, tetrathiomolybdate, thrombospondin, thalidomide, prolactin, αVβ3 inhibitor, lenalidomide, linomide, ramucirumab, tasquinimod, ranibizumab, sorafenib, sunitinib, pazopanib, everolimus, tissue inhibitors of metalloproteases (TIMP1 and TIMP2), bFGF soluble receptor, transforming growth factor beta, interferon alpha, soluble KDR and FLT-1 receptors, placental proliferin-related protein, pazopanib, sunitinib, sorafenib, axitinib, ponatinib, cabozantinib, regorafenib, vandetanib, lenvatinib, semaxanib, SU6668, vatalanib, tivozanib, cediranib, protamine, heparin, steroids, ascorbic acid ethers, sulfated polysaccharide DS 4152, fumagillin, AGM 12470, neovastat, R04929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, OMP-21M18, navicixizumab (OMP-305B83), Flt2-11, CBO-P11, Je-11, V1, and any combination thereof.

In some embodiments, the angiogenesis inhibitor inhibits a vascular endothelial growth factor (VEGF)/vascular endothelial growth factor receptor (VEGFR) pathway. In some embodiments, the angiogenesis inhibitor inhibits a VEGF family protein and/or a VEGFR family protein. In some embodiments, the VEGF family protein comprises VEGF-A, VEGF-B, VEGF-C, VEGF-D, PlGF (placental growth factor), VEGF-E (Orf-VEGF), Trimeresurus flavoviridis svVEGF, or any combination thereof. In some embodiments, the VEGFR family protein comprises VEGFR-1, VEGFR-2, VEGFR-3, or any combination thereof. In some embodiments, the angiogenesis inhibitor comprises a VEGF inhibitor, a VEGFR inhibitor, or a combination thereof. In some embodiments, the angiogenesis inhibitor induces homologous recombinant (HR) deficiency. In some embodiments, the angiogenesis inhibitor induces hypoxia. In some embodiments, the angiogenesis inhibitor induces homologous recombinant (HR) deficiency by hypoxia. In some embodiments, the VEGF inhibitor is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; a toxin; or any combination thereof. In some embodiments, the VEGF inhibitor is an antibody or a fragment thereof. In some embodiments, the VEGF inhibitor is bevacizumab, ranibizumab, OPT-302, ziv-aflibercept, or any combinations thereof. In some embodiments, the VEGF inhibitor is a small organic or inorganic molecule. In some embodiments, the small organic or inorganic molecule is $Flt_{2-11}$, CBO-P11, Je-11, V1, or any combination thereof. In some embodiments, the VEGFR inhibitor is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; a toxin; or any combination thereof. In some embodiments, the VEGFR inhibitor is a tyrosine kinase inhibitor. In some embodiments, the tyrosine kinase inhibitor is pazopanib, sunitinib, sorafenib, axitinib, ponatinib, cabozantinib, regorafenib, vandetanib, lenvatinib, semaxanib, SU6668, vatalanib, tivozanib, cediranib, or any combination thereof. In some embodiments, the VEGFR inhibitor is an antibody or a fragment thereof. In some embodiments, the VEGFR inhibitor is ramucimmab.

In embodiments, a first agent is niraparib, and a second agent is bevacizumab.

In embodiments, a first agent is niraparib, and a second agent is cabozantinib.

Therapeutic methods of the invention can be combined with additional immunotherapies and therapies. For example, when used for treating cancer, inhibitors of the invention can be used in combination with conventional cancer therapies, such as, e.g., surgery, radiotherapy, chemotherapy or combinations thereof, depending on type of the tumor, patient condition, other health issues, and a variety of factors.

In embodiments, a further therapeutic agent is an immune checkpoint inhibitor. In embodiments, a checkpoint inhibitor is an agent capable of inhibiting any of the following: PD-1 (e.g., inhibition via anti-PD-1, anti-PD-L1, or anti-PD-L2 therapies), CTLA-4, TIM-3, TIGIT, LAGs (e.g., LAG-3), CEACAM (e.g., CEACAM-1, -3 and/or -5), VISTA, BTLA, LAIR1, CD 160, 2B4, CD80, CD86, B7-H3 (CD276), B7-H4 (VTCN1), HVEM (TNFRSF 14 or CD270), KIR, A2aR, MHC class I, MHC class II, GALS, adenosine, TGFR (e.g., TGFR beta), B7-H1, B7-H4 (VTCN1), OX-40, CD137, CD40, IDO, or CSF-1R. In embodiments, a checkpoint inhibitor is a small molecule, a nucleic acid, a polypeptide (e.g., an antibody), a carbohydrate, a lipid, a metal, or a toxin. In embodiments, a checkpoint inhibitor is an antibody, an antibody conjugate, or an antigen-binding fragment thereof.

In certain aspects, other therapeutic agents useful for combination therapy with the inhibitors of the present disclosure include an antigen specific immune response enhancer agent selected from the group consisting of an anti-PD-1 agent, an anti-PD-L1 agent, a GITR (glucocorticoid-induced TNFR-related protein) stimulating agent, an anti-CTLA4 agent, an anti-TIM-3 agent, an anti-LAG-3 agent, a chemokine signaling agent, an anti-VEGF agent, a cytokine signal stimulating agent, and combinations thereof.

In embodiments, an immune checkpoint inhibitor is a PD-1 inhibitor. In embodiments, a PD-1 inhibitor is a small molecule, a nucleic acid, a polypeptide (e.g., an antibody, an antibody conjugate, or an antigen-binding fragment thereof), a carbohydrate, a lipid, a metal, or a toxin. In embodiments, a PD-1 inhibitor is a PD-1 binding agent (e.g., an antibody, an antibody conjugate, or an antigen-binding fragment thereof). In embodiments, a PD-1 binding agent is an antibody, an antibody conjugate, or an antigen-binding fragment thereof. In some embodiments, the anti-PD-1 agent is selected from the group consisting of pembrolizumab, nivolumab, PDR001, REGN2810 (SAR-439684), BGB-A317, BI 754091, IBI308, INCSHR-1210, JNJ-63723283, JS-001, MEDI0680 (AMP-514), MGA-012, PF-06801591, REGN-2810, TSR-042, and combinations thereof. In embodiments, a PD-1 inhibitor is an anti-PD-L1 or anti-PD-L2 agent. In some embodiments, the anti-PD-L1 agent is selected from the group consisting of atezolizumab, durvalumab, avelumab, LY3300054, and combinations thereof. In embodiments, an anti-PD-1 agent is pembrolizumab. In embodiments, an anti-PD-1 agent is nivolumab. In some embodiments, a PD-1 antibody agent is as disclosed in International Patent Application Publication Nos. WO2014/179664, WO 2018/085468, or WO 2018/129559. In further embodiments, a PD-1 antibody agent is administered according to a method disclosed in International Patent Application Publication Nos. WO2014/179664, WO 2018/085468, or WO 2018/129559. In embodiments, an anti-PD-1 agent is TSR-042.

In embodiments, an immune checkpoint inhibitor is a TIM-3 inhibitor. In embodiments, a TIM-3 inhibitor is a small molecule, a nucleic acid, a polypeptide (e.g., an antibody, an antibody conjugate, or an antigen-binding fragment thereof), a carbohydrate, a lipid, a metal, or a toxin. In embodiments, a TIM-3 inhibitor is a TIM-3 binding agent (e.g., an antibody, an antibody conjugate, or an antigen-binding fragment thereof). In embodiments, a TIM-3 binding agent is an antibody, an antibody conjugate, or an antigen-binding fragment thereof. In some embodiments, a TIM-3 antibody agent is MBG453, LY3321367, Sym023, TSR-022, or a derivative thereof. In some embodiments, a TIM-3 antibody agent is as disclosed in International Patent Application Publication Nos. WO2016/161270, WO 2018/085469, or WO 2018/129553. In some embodiments, a TIM-3 antibody agent is administered as disclosed in International Patent Application Publication Nos. WO2016/161270, WO 2018/085469, or WO 2018/129553. In some embodiments, a TIM-3 antibody agent is TSR-022.

In embodiments, an immune checkpoint inhibitor is a LAG-3 inhibitor. In embodiments, an anti-LAG-3 agent is an antibody, an antibody conjugate, or an antigen-binding fragment thereof. In embodiments, an anti-LAG-3 agent is a small molecule, a nucleic acid, a polypeptide (e.g., an antibody), a carbohydrate, a lipid, a metal, or a toxin. In embodiments, an anti-LAG-3 agent is a small molecule. In embodiments, an anti-LAG-3 agent is a LAG-3 binding agent. In embodiments, an anti-LAG-3 agent is an antibody, an antibody conjugate, or an antigen-binding fragment thereof. In embodiments, an anti-LAG-3 agent is IMP321, relatlimab (BMS-986016), BI 754111, GSK2831781 (IMP-731), Novartis LAG525 (IMP701), REGN3767, MK-4280, MGD-013, GSK-2831781, FS-118, XmAb22841, INCAGN-2385, FS-18, ENUM-006, AVA-017, AM-0003, Avacta PD-L1/LAG-3 bispecific affamer, iOnctura anti-LAG-3 antibody, Arcus anti-LAG-3 antibody, or Sym022, or TSR-033. In some embodiments, a LAG-3 antibody agent is as disclosed in International Patent Application Publication WO2016/126858 or in in International Patent Application No. PCT/US18/30027. In some embodiments, a LAG-3 antibody agent is administered as disclosed in International Patent Application Publication WO2016/126858 or in in International Patent Application No. PCT/US18/30027. In embodiments, a LAG-3 antibody agent is TSR-033.

In some embodiments, the GITR stimulating agent is selected from the group consisting of DTA-1, mGITRL, pGITRL, and combinations thereof.

In some embodiments, the anti-CTLA4 agent is selected from the group consisting of ipilimumab, tremelimumab, and combinations thereof.

In some embodiments, the chemokine signaling agent is selected from the group consisting of CXCL16, a CXCR6 chemokine receptor (CD186) agonist, and combinations thereof.

In some embodiments, the cytokine signal stimulating agent is an interleukin or an interferon. In some embodiments, the interleukin is selected from the group consisting of IL-2, IL-1, IL-7, IL-15, IL-12, IL-18 and combinations thereof. In some embodiments, the interferon is IFN alpha.

In some embodiments, the third agent is an antigen specific immune response enhancer agent selected from the group consisting of a flavonoid (e.g., flavonoid glycoside), lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin.

In some embodiments, the third agent is a chemotherapeutic agent. Non-limiting examples of chemotherapeutic agents which can be used in combination treatments of the present disclosure include, for example, aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hex amethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

As used herein, a "chemotherapeutic agent" refers to a chemical agent that inhibits the proliferation, growth, lifespan and/or metastatic activity of cancer cells. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines (e.g., altretamine, triethyl enemelamine, trietylenephosphoramide, triethiylenethiophosphoramide and trimethylolomelamine); acetogenins; delta-9-tetrahydrocannabinol (e.g., dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and raninmustine; antibiotics such as the enediyne antibiotics (e.g., calicheamicin); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; xeloda; ibandronate; topoisomerase inhibitor RFS 2000; difluoromethylornithine (DMFO); retinoids such as retinoic acid; capecitabine; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are "antimetabolite chemotherapeutic agents" that are structurally similar to a metabolite, but cannot be used by the body in a productive manner. Many antimetabolite chemotherapeutic agents interfere with the production of the nucleic acids, RNA and DNA. Examples of antimetabolite chemotherapeutic agents include gemcitabine (GEMZAR®), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U®), dacarbazine (DTIC-DOMED), azocytosine, deoxycytosine, pyridmidene, fludarabine (FLUDARA®), cladrabine, 2-deoxy-D-glucose etc. In some embodiments, an antimetabolite chemotherapeutic agent is gemcitabine. Gemcitabine HCl is sold by Eli Lilly under the trademark GEMZAR®.

Also included in this definition are "platinum-based chemotherapeutic agents" that comprises an organic compound which contains platinum as an integral part of the molecule. In some embodiments, a chemotherapeutic agent is a platinum agent. In some such embodiments, the platinum agent is selected from cisplatin, carboplatin, oxaliplatin, nedaplatin, triplatin tetranitrate, phenanthriplatin, picoplatin, or satraplatin.

Administration

The composition or pharmaceutical composition or therapeutic agent disclosed here can be administered into a subject by various methods. Those of ordinary skill in the art will be aware of a variety of routes that may, in appropriate circumstances, be utilized for administration to a subject, for example a human subject. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time. For further examples, the pharmaceutical composition can be formulated for administration via pH-dependent release delivery, microbially-triggered delivery, time-controlled delivery, osmotically-regulated delivery, pressure-controlled delivery, multi matrix systems delivery, bioadhesion delivery, or multiparticulate delivery.

Pharmaceutical compositions of the present disclosure include, but are not limited to, granules, tablets (single layered tablets, multilayered tablets, mini tablets, bioadhesive tablets, caplets, matrix tablets, tablet within a tablet, mucoadhesive tablets, modified release tablets, orally disintegrating tablets, pulsatile release tablets, timed release tablets, delayed release, controlled release, extended release and sustained release tablets), capsules (hard and soft or liquid filled soft gelatin capsules), pills, troches, sachets, powders, microcapsules, minitablets, tablets in capsules and microspheres, matrix composition and the like. In some embodiments, the pharmaceutical composition refers to capsules. In some embodiments, the pharmaceutical composition refers to hard gelatin capsules or HPMC based capsules. In some embodiments, the pharmaceutical composition refers to hard gelatin capsules.

In some embodiments, a given therapeutic agent is administered according to a regimen, which may involve one or more doses. In some embodiments, a regimen comprises a plurality of doses each of which is separated in time from other doses. In some embodiments, individual doses are separated from one another by a time period of the same length; in some embodiments, a regimen comprises a plurality of doses, wherein the doses are separated by time periods of different length. In some embodiments, a regimen comprises doses of the same amount. In some embodiments, a regimen comprises doses of different amounts. In some embodiments, a regimen comprises at least one dose, wherein the dose comprises one unit dose of the therapeutic agent. In some embodiments, a regimen comprises at least one dose, wherein the dose comprises two or more unit doses of the therapeutic agent.

In various embodiments, the methods provided herein comprise administering a first agent and a second agent. A first agent and a second agent can be administered in any order. In some embodiments, administering comprises administering the first and second agent sequentially. In some embodiments, administering comprises administering the first and second agent simultaneously. In some embodiments, administering comprises administering the first agent before administering the second agent. In some embodiments, administering comprises administering the second agent before administering the first agent.

In some embodiments, the pharmaceutical composition is administered to a subject and the administering comprises administering a composition comprising a capsule, wherein the capsule comprises the first agent. In some embodiments, the capsule comprises a formulation comprising the first agent and one or more pharmaceutically acceptable excipients. In some embodiments, the one or more pharmaceutically acceptable excipients comprise lactose monohydrate, magnesium stearate, or a combination thereof. In some embodiments, a therapeutically effective amount of the first or second agent is administered. In some embodiments, the method further comprises administering a third agent to the subject. In some embodiments, the third agent comprises an antigen specific immune response enhancer agent, a chemotherapeutic agent, or a combination thereof. In some embodiments, the antigen specific immune response enhancer agent comprises an anti-PD-1 agent, an anti-PD-L1 agent, an anti-CTLA4 agent, an anti-TIM-3 agent, or an anti-LAG-3 agent.

Dosing Protocols

As described herein, provided methods comprise administering a therapy that inhibits PARP and a therapy that regulates activity in the tumor microenvironment (e.g., inhibition of angiogenesis) in combination to a patient, a subject, or a population of subjects according to a regimen that achieves a therapeutic effect.

In some embodiments, administration "in combination" includes administration of one or more doses of an agent that inhibits PARP (e.g., niraparib) before, during, or after administration of one or more doses of an agent that enhances activity in the tumor microenvironment. In some embodiments, an agent that inhibits PARP (e.g., niraparib) and an agent that regulates activity in the tumor microenvironment are administered in overlapping regimens. In some embodiments, an agent that inhibits PARP (e.g., niraparib) is administered simultaneously or sequentially to an agent that enhances activity in the tumor microenvironment.

The number of times a composition is administered to an individual in need thereof depends on the discretion of a medical professional, the disorder, the severity of the disorder, and the individual's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of a combination drug product described herein may be administered chronically, that is, for an extended period of time, including throughout the duration of the patient's life in order to ameliorate or otherwise control or limit the symptoms of the patient's disease or condition.

In some embodiments, a therapeutically-effective amount of a therapeutic agent is administered to a subject. The therapeutic agent can be a first, a second, or a third agent. In some embodiments, the therapeutically-effective amount is from about 0.1 milligram per kilogram of body weight per day (mg/kg/day) to about 1 mg/kg/day, from 1 mg/kg/day to about 5 mg/kg/day, from 5 mg/kg/day to about 10 mg/kg/day, from 10 mg/kg/day to about 15 mg/kg/day, from 15 mg/kg/day to about 20 mg/kg/day, from 20 mg/kg/day to about 25 mg/kg/day, from 25 mg/kg/day to about 30 mg/kg/day, from 30 mg/kg/day to about 35 mg/kg/day, or from 35 mg/kg/day to about 40 mg/kg/day. In some embodiments, the therapeutically-effective amount is from 0.1 mg/kg/day to about 40 mg/kg/day. In some embodiments, the therapeutically-effective amount is from 10 mg/kg/day to about 50 mg/kg/day, or from 50 mg/kg/day to about 100 mg/kg/day.

In some embodiments, a first agent is administered at a dose that is equivalent to about 300 mg of niraparib. In some embodiments, the first agent is administered at a reduced dose. In some embodiments, the reduced dose is equivalent to 200 mg of niraparib. In some embodiments, the reduced dose is equivalent to 100 mg~150 mg, or 150 mg~200 mg of niraparib. In some embodiments, the first agent (e.g. niraparib) is administered at an increased dose if the subject's hemoglobin≥9 g/dL, platelets≥100,000/µL and neutrophils≥1500/µL for all labs performed during one or more treatment cycles. In some embodiments, the dose of the first agent (e.g. niraparib) is increased after two cycles of treatment.

Subjects

In practicing the methods of treatment or use provided herein, therapeutically-effective amounts of the therapeutic agents can be administered to a subject having a disease or condition. A therapeutically-effective amount can vary widely depending on the severity of the disease, the age and relative health of the subject, the potency of the compounds used, and other factors.

Subjects can be, for example, mammals, humans, pregnant women, elderly adults, adults, adolescents, pre-adolescents, children, toddlers, infants, newborn, or neonates. A subject can be a patient. In some cases, a subject can be a human. In some cases, a subject can be a child (i.e., a young human being below the age of puberty). In some cases, a subject can be an infant. In some cases, the subject can be a formula-fed infant. In some cases, a subject can be an individual enrolled in a clinical study. In some cases, a subject can be a laboratory animal, for example, a mammal, or a rodent. In some cases, the subject can be a mouse. In some cases, the subject can be an obese or overweight subject.

In some embodiments, the subject has previously been treated with one or more different cancer treatment modalities. In some embodiments, the subject has previously been treated with one or more of radiotherapy, chemotherapy, or immunotherapy. In some embodiments, the subject has been treated with one, two, three, four, or five lines of prior therapy. In some embodiments, the prior therapy is a cytotoxic therapy.

Compositions and Kits

A composition or pharmaceutical composition of the present disclosure can comprise any of the agents disclosed herein. In some embodiments, the composition or pharmaceutical composition comprises one or more therapeutic agents. The composition or pharmaceutical composition can be administered in combination with another therapy, for example, immunotherapy, chemotherapy, radiotherapy, anti-inflammatory agents, anti-viral agents, anti-microbial agents, and anti-fungal agents.

A composition or a pharmaceutical composition of the present disclosure can be packaged as a kit. In some embodiments, a kit comprises a pharmaceutical composition disclosed herein. In some embodiments, a kit comprises a first, a second, and/or a third therapeutic agent disclosed herein. In some applications, a kit includes written instructions on the administration/use of the therapeutic composition. The written material can be, for example, a label. The written material can suggest conditions methods of administration. The instructions provide the subject and the supervising physician with the best guidance for achieving the optimal treatment outcome from the administration of the therapy. The written material can be a label. In some applications, the label can be approved by a regulatory agency, for example the U.S. Food and Drug Administration (FDA), the European Medicines Agency (EMA), or other regulatory agencies.

EXAMPLES

The following examples evaluated antitumor activity of PARP inhibitors in combination with angiogenesis inhibitors. The compounds of these combination therapies serve as examples only, and are not intended to be limiting.

Example 1—Study Design

In vivo studies were designed in order to test the effect of combination treatments. The study design is summarized in Table 1.

TABLE 1

In vivo study design for combination treatment

| Tumor type | Ovarian Cancer | | TNBC |
|---|---|---|---|
| Model | A2780 | A2780, OVC134 | MAXF 574, MAXF 857, MAXF MX1 |
| Mouse Strain | CB-17 SCID female | Balb/C nude female | NMRI nude female |
| Treatment arms | Vehicle Niraparib (N) Bevacizumab (B) N + B | Vehicle Niraparib (N) Cabozantinib (C) N + C | Vehicle Niraparib (N) Bevacizumab (B) Cabozantinib (C) N + B N + C |
| Number of mice per arm | 6 | 6 | 3 |
| Niraparib dosing | 60 mg/kg po qd | 60 mg/kg po qd | 50 mg/kg po qd |
| Bevacizumab dosing | 10 mg/kg iv qw | | 20 mg/kg iv qw |
| Cabozantinib dosing | | 30 mg/kg po qd | 30 mg/kg po qd |

"po" means "by mouth", "qd" means "once a day", "iv" means "intravenous", and "qw" means "once a week"

Example 2—Niraparib and Bevacizumab Combination Therapy Demonstrated Enhanced Anti-Tumor Activity in Both Ovarian and TNBC Models As shown in FIG. 1, one ovarian cancer (OC) model and three triple negative breast cancer (TNBC) models were treated with niraparib, bevacizumab, and their combination. Tumor growth inhibition (TGI) at the end of treatment was calculated and illustrated. Combination benefit (TGI for N+B at least 10% higher than either monotherapy) was observed in OC model A2780 and TNBC model MAXF 574. Combination benefit could not be seen in the other two TNBC models MAXF 857 and MAXF MX1 because the models are sensitive to bevacizumab monotherapy (TGI: 76%) and niraparib monotherapy (TGI: 99%), respectively.

Figure 2:
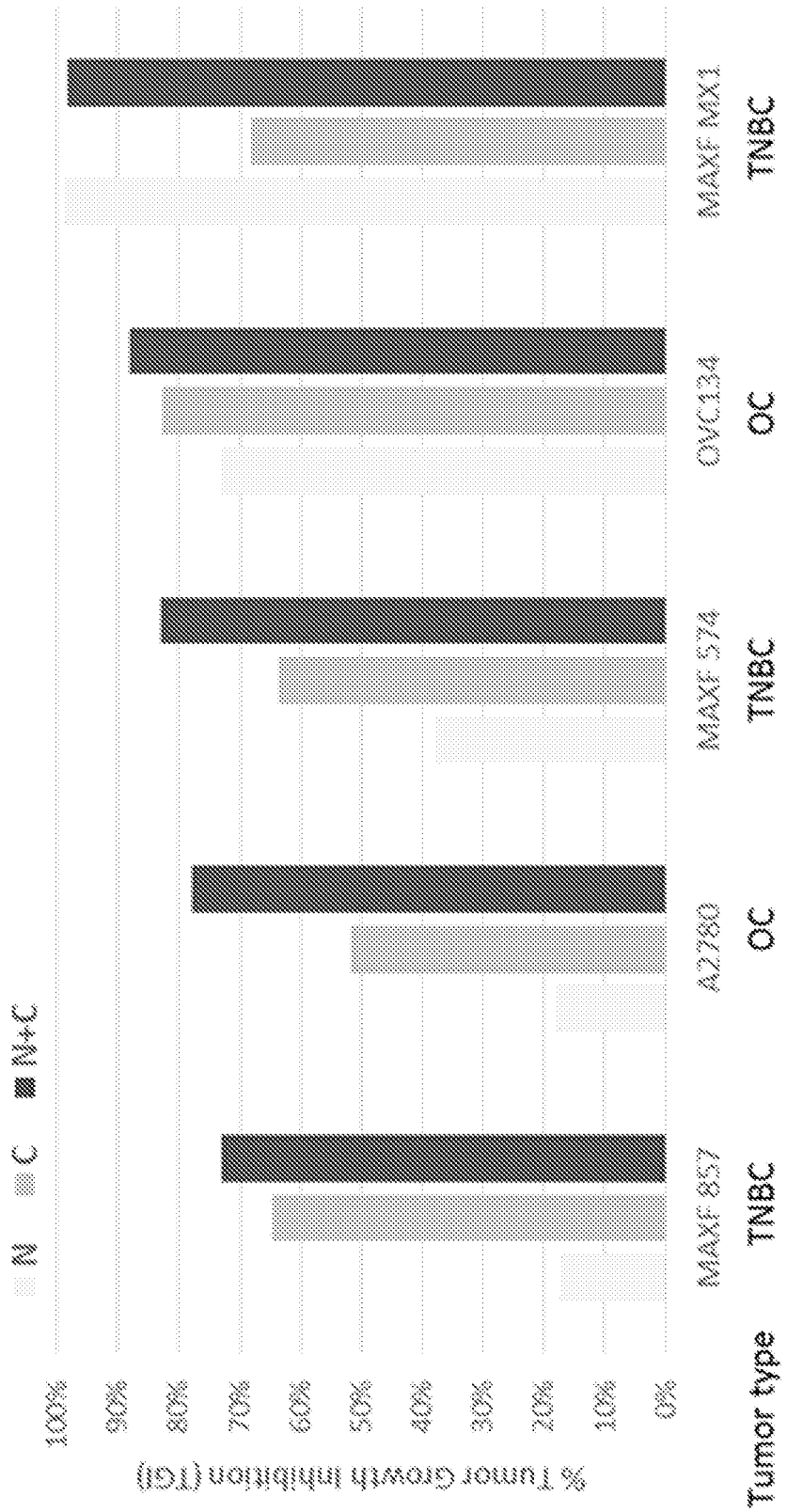
FIG. 2 depicts an exemplary study of niraparib and cabozantinib combination treatment in both ovarian and TNBC models.

Example 3—Niraparib and Cabozantinib Combination Therapy Demonstrated Enhanced Anti-Tumor Activity in Both Ovarian and TNBC Models As shown in FIG. 2, two ovarian cancer models and three TNBC models were treated with niraparib, cabozantinib, and their combinations. Tumor growth inhibition at the end of treatment was calculated and illustrated. Combination benefit (TGI for N+C at least 10% higher than either monotherapy) was observed in OC model A2780 and TNBC model MAXF 574. Combination benefit could not be seen in the other three models because OVC134 and MAXF 857 are sensitive to cabozantinib monotherapy (TGI: 83% and 65% respectively), and MAXF MX1 is sensitive to niraparib monotherapy (TGI: 99%).

Example 4—Results of Tolerability and Antitumor Activity of Niraparib and Bevacizumab Combination in Ovarian Cancer Cell Line-Derived Xenograft Model A2780 (BRCA wt, HRD−)

Figure 3A:
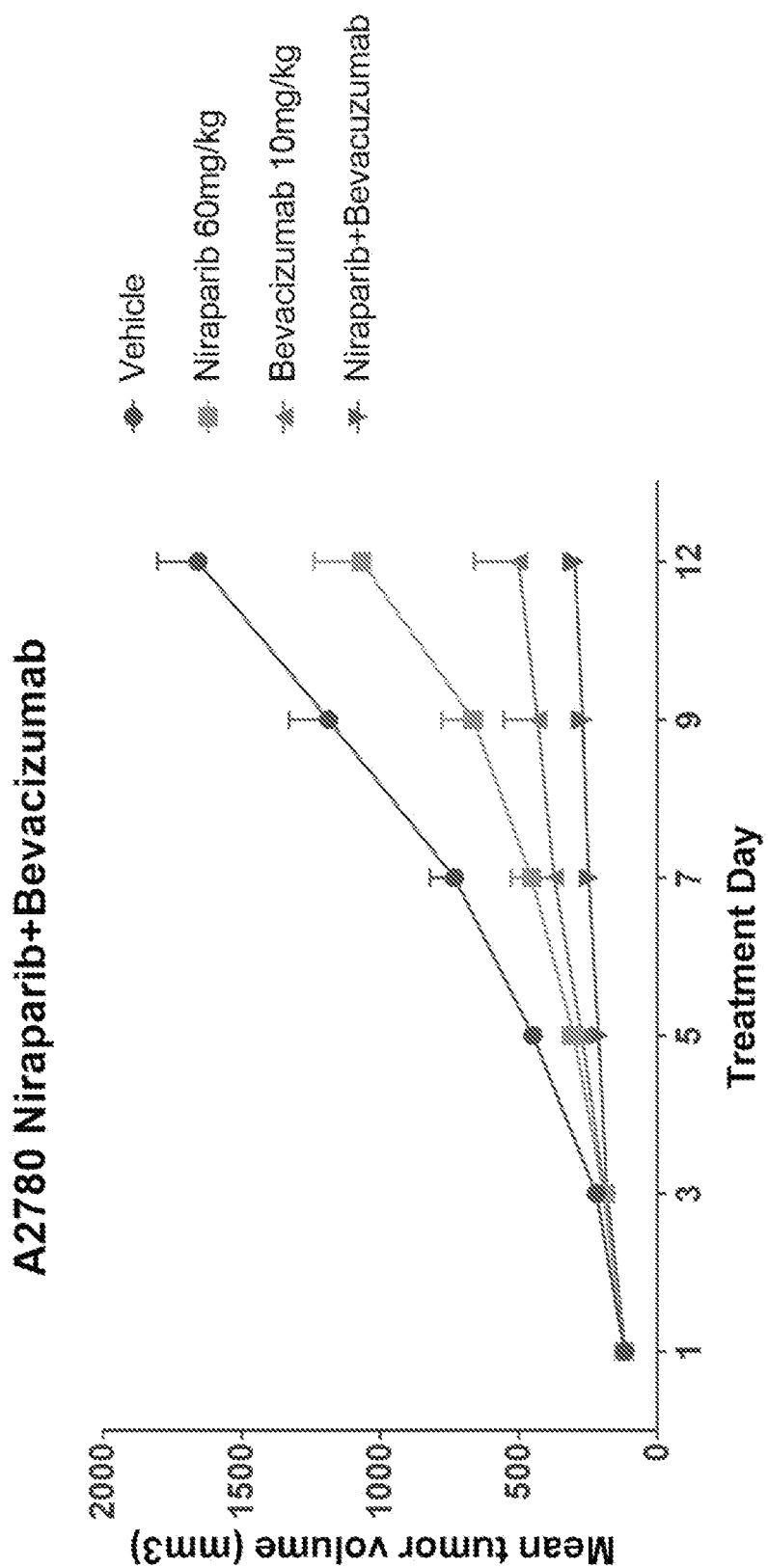
FIG. 3A depicts an exemplary study of tolerability and antitumor activity of niraparib and bevacizumab combination measured by mean tumor volume in ovarian cancer cell line-derived xenograft model A2780 (BRCA wt, homologous recombination deficiency negative (HRD−)).
Figure 3B:
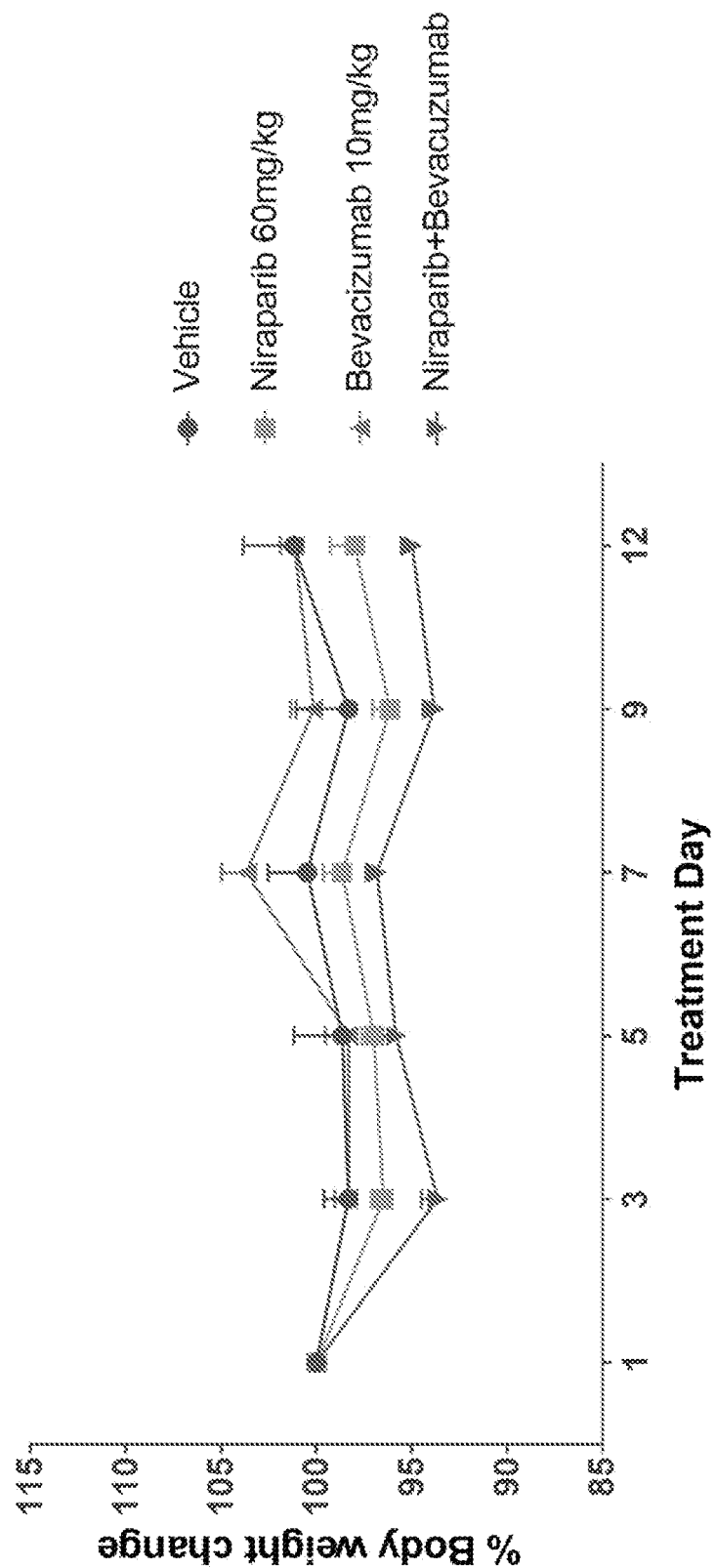
FIG. 3B depicts an exemplary study of tolerability and antitumor activity of niraparib and bevacizumab combination measured by body weight in ovarian cancer cell line-derived xenograft model A2780 (BRCA wt, HRD−).

As shown in FIGS. 3A and 3B, tumor bearing mice were randomized into 4 cohorts and treated with vehicle, niraparib, cabozantinib, and niraparib+cabozantinib for 2 weeks. Tumor size and body weight were measured twice weekly. Both monotherapies and the combination are well tolerated without significant body weight loss. In this BRCA wild type and HRD negative model, combination of niraparib and bevacizumab demonstrated enhanced anti-tumor activity (TGI=68%) compared with niraparib monotherapy (TGI<40%) and bevacizumab monotherapy (TGI=55%).

Example 5—Results of Tolerability and Antitumor Activity of Niraparib and Cabozantinib Combination in Ovarian Cancer Cell Line-Derived Xenograft Model A2780 (BRCA wt, HRD−)

Figure 4A:
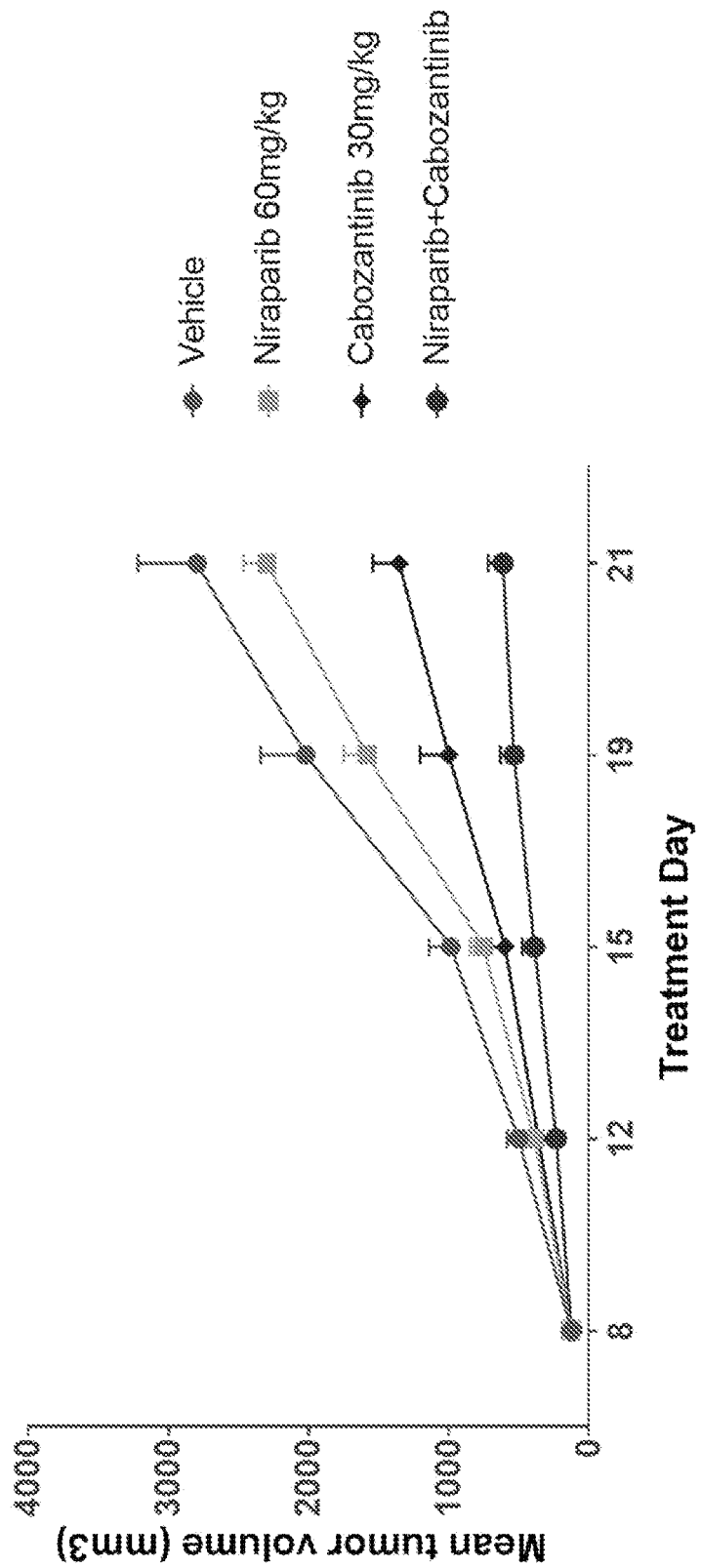
FIG. 4A depicts an exemplary study of tolerability and anti-tumor activity of niraparib and cabozantinib combination measured by mean tumor volume in ovarian cancer cell line-derived xenograft model A2780 (BRCA wt, HRD−).
Figure 4B:
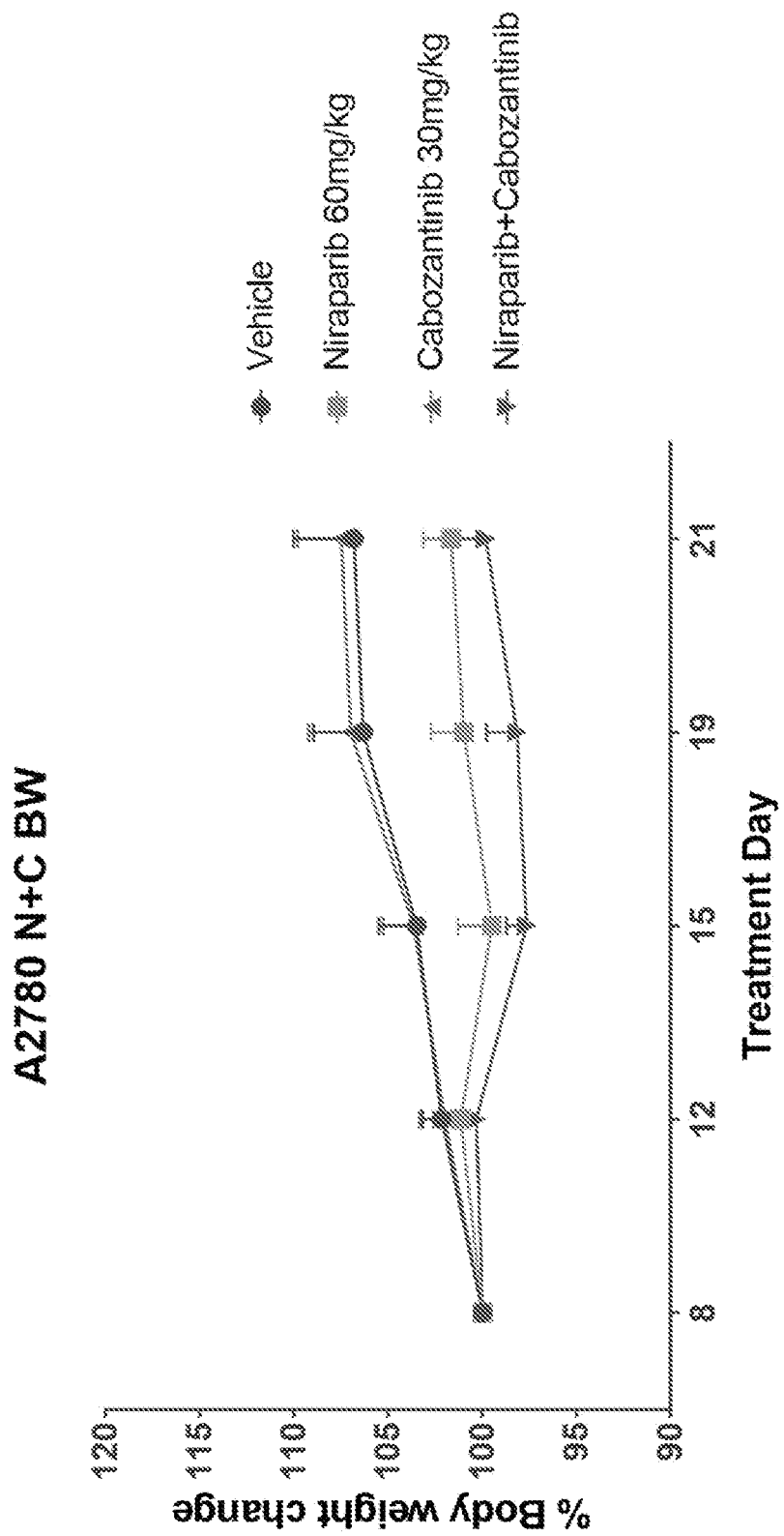
FIG. 4B depicts an exemplary study of tolerability and anti-tumor activity of niraparib and cabozantinib combination measured by body weight in ovarian cancer cell line-derived xenograft model A2780 (BRCA wt, HRD−).

As shown in FIGS. 4A and 4B, tumor bearing mice were randomized into 4 cohorts and treated with vehicle, niraparib, cabozantinib, and niraparib+cabozantinib combination for 2 weeks. Tumor size and body weight were measured twice weekly. Both monotherapies and the combination are well tolerated with no significant body weight loss. In this BRCA wild type and HRD negative model, combination of niraparib and cabozantinib demonstrated enhanced anti-tumor activity (TGI=78%) compared with niraparib monotherapy (TGI 18%) and cabozantinib monotherapy (TGI=51%).

Example 6—Results of Anti-Tumor Activity of Niraparib and Cabozantinib Combination in Ovarian PDX Model OVC134

Figure 5:
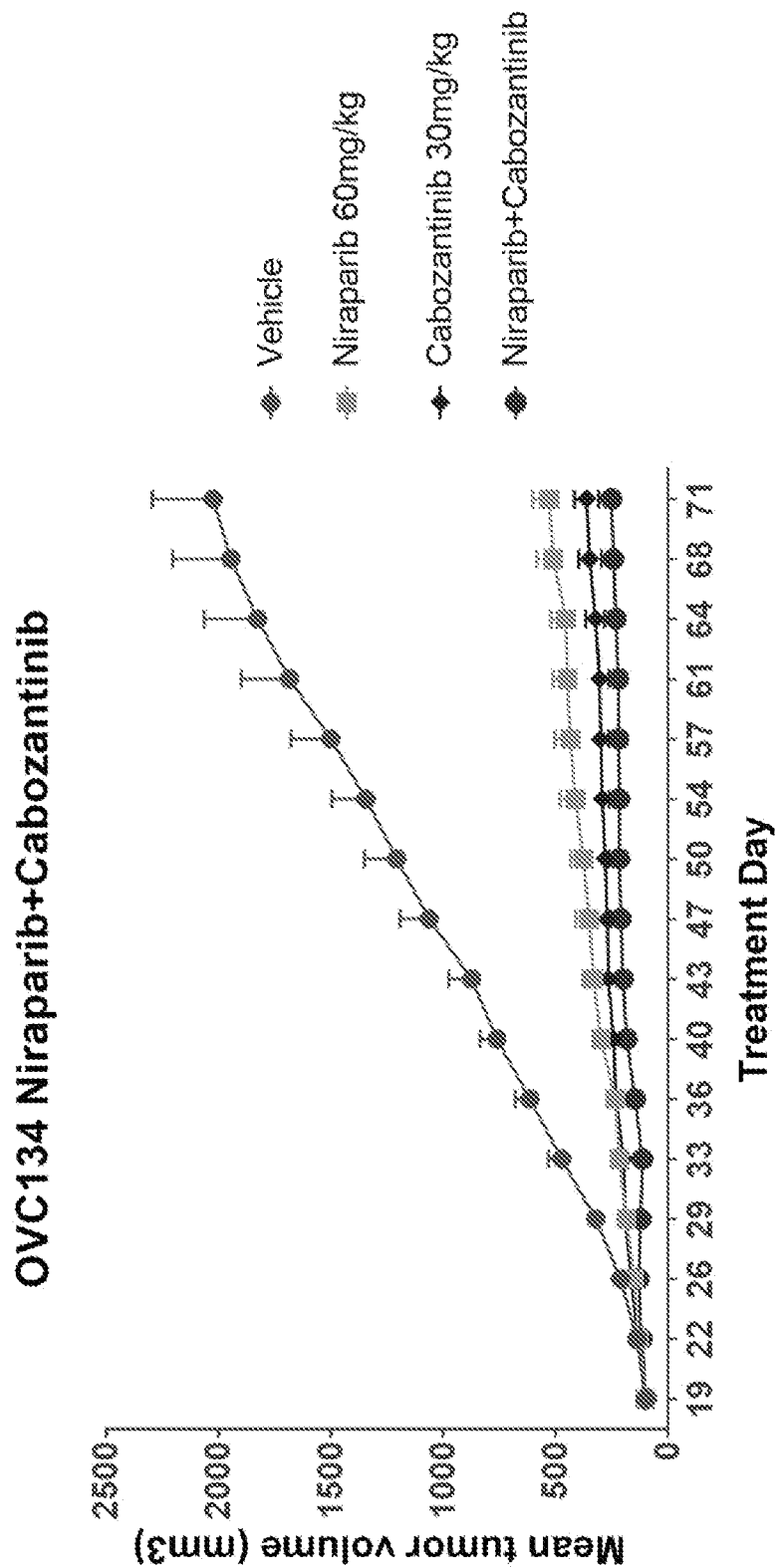
FIG. 5 depicts an exemplary study of anti-tumor activity of niraparib and cabozantinib combination in ovarian patient-derived xenograft (PDX) model OVC134.

As shown in FIG. 5, tumor bearing mice were randomized into 4 cohorts and treated with vehicle, niraparib, cabozantinib, and niraparib+cabozantinib combination for 7 weeks. Tumor size and body weight were measured twice weekly. This model is very sensitive to both niraparib and cabozantinib monotherapy, therefore no additional combination benefit could be observed for the combination.

Example 7—Results of Anti-Tumor Activity of Niraparib+Bevacizumab Combination and Niraparib+Cabozantinib Combination in TNBC PDX Model MAXF 574

Figure 6A:
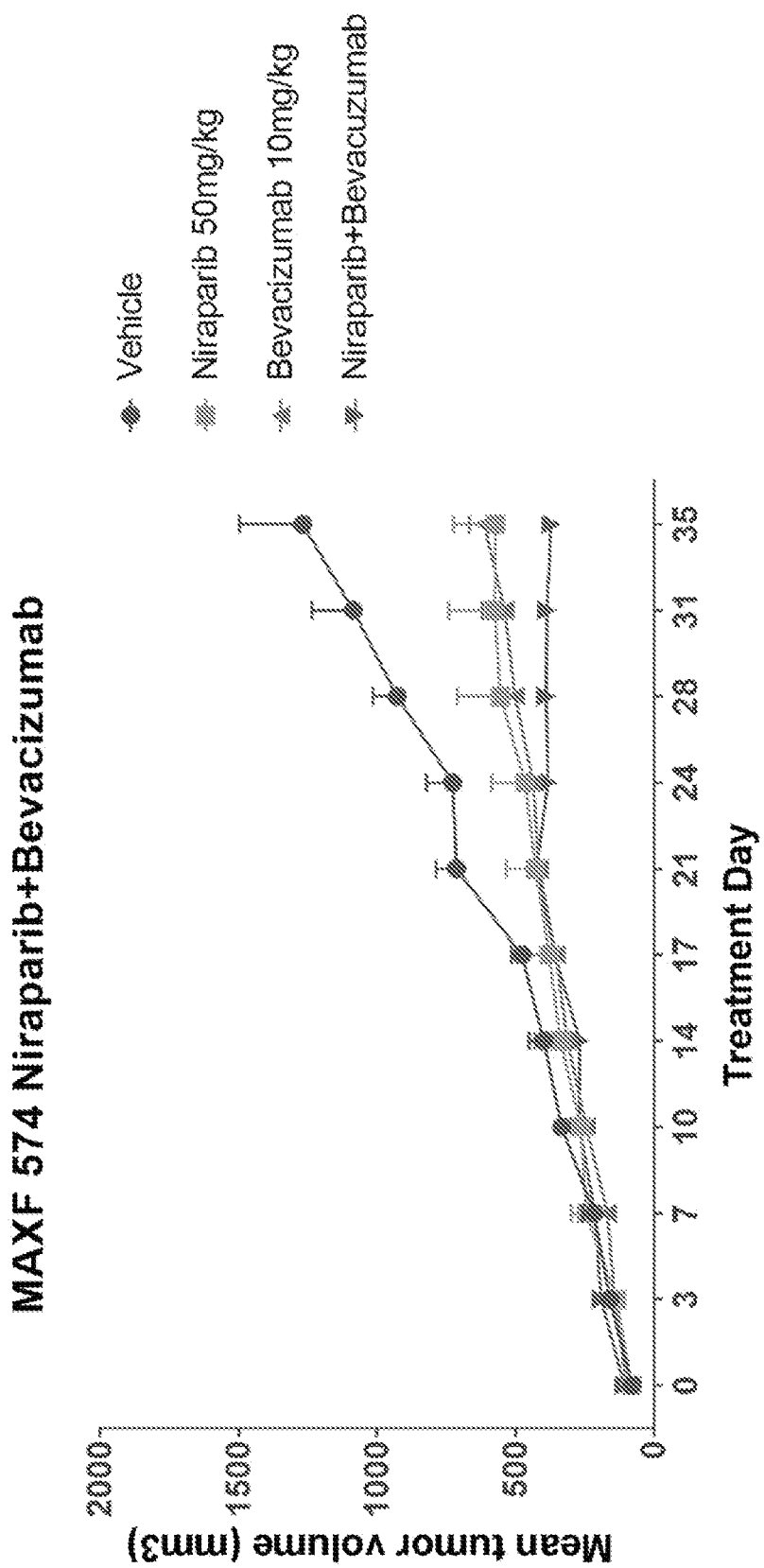
FIG. 6A depicts an exemplary study of anti-tumor activity of niraparib and bevacizumab combination in TNBC PDX model MAXF 574.
Figure 6B:
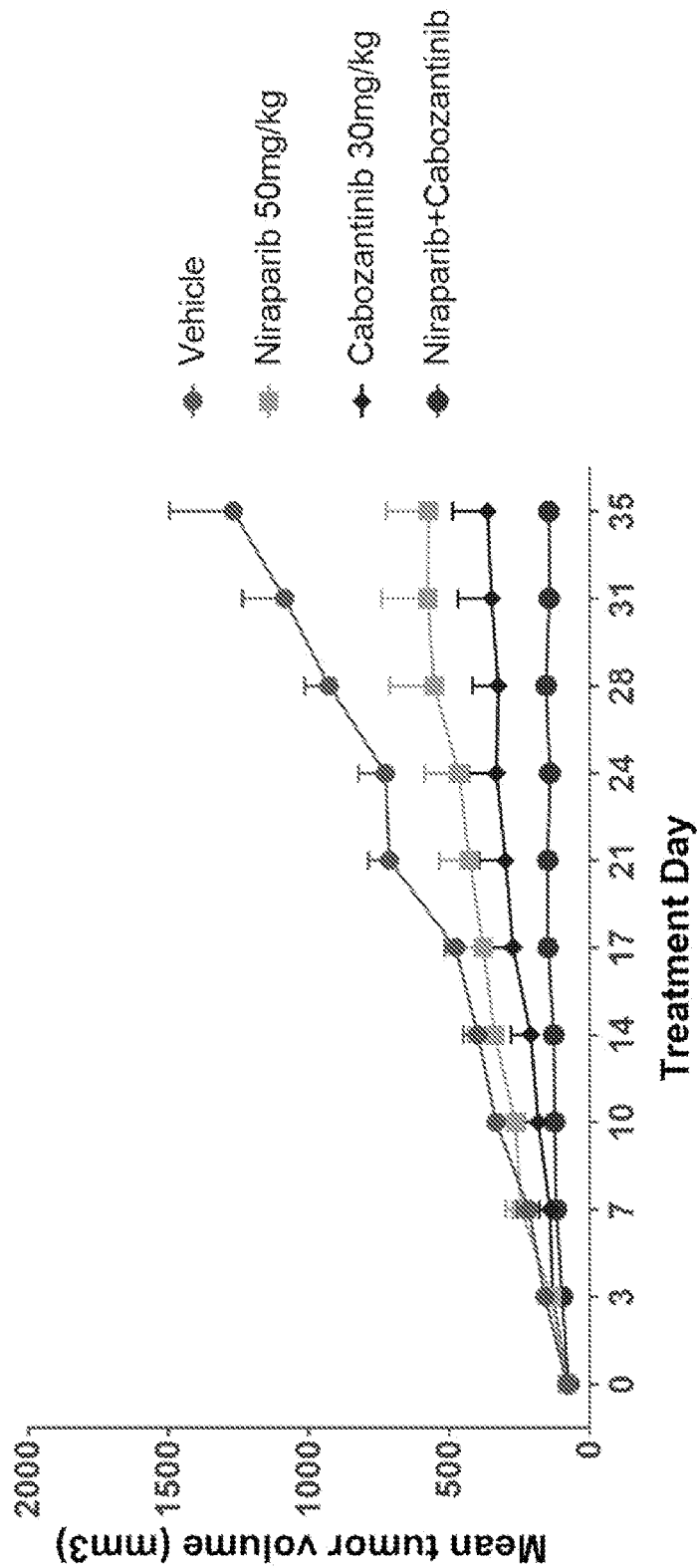
FIG. 6B depicts an exemplary study of anti-tumor activity of niraparib and cabozantinib combination in TNBC PDX model MAXF 574.

As shown in FIGS. 6A and 6B, tumor bearing mice were randomized into 6 cohorts and treated with vehicle, niraparib, bevacizumab, niraparib+bevacizumab combination, cabozantinib, and niraparib+cabozantinib combination for 5 weeks. Tumor size and body weight were measured twice weekly. Combination benefit was observed for both niraparib+bevacizumab and niraparib+cabozantinib combinations.

Example 8—Results of Anti-Tumor Activity of Niraparib+Bevacizumab Combination and Niraparib+Cabozantinib Combination in TNBC PDX Model MAXF 857

Figure 7A:
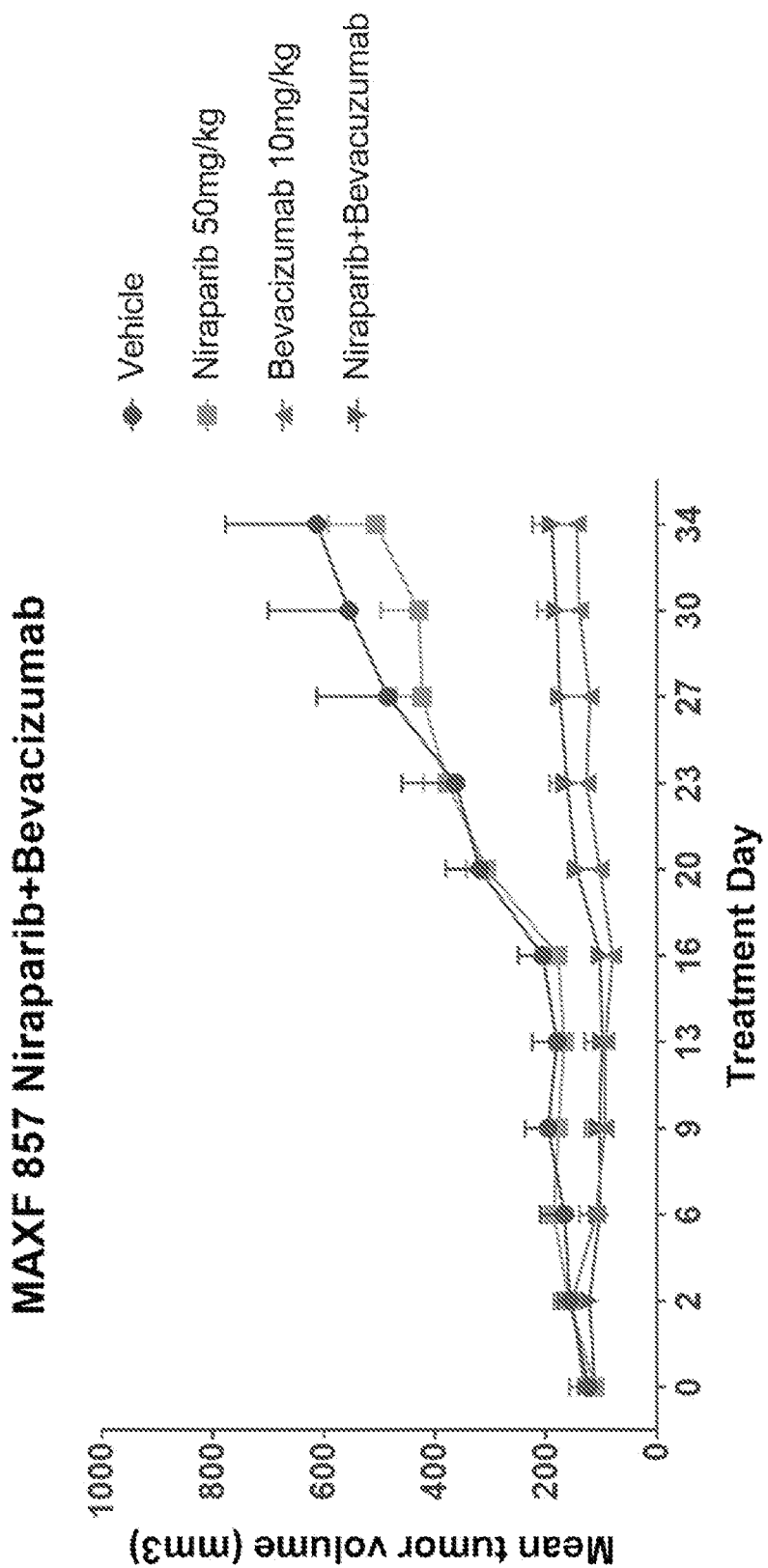
FIG. 7A depicts an exemplary study of anti-tumor activity of niraparib and bevacizumab combination in TNBC PDX model MAXF 857.
Figure 7B:
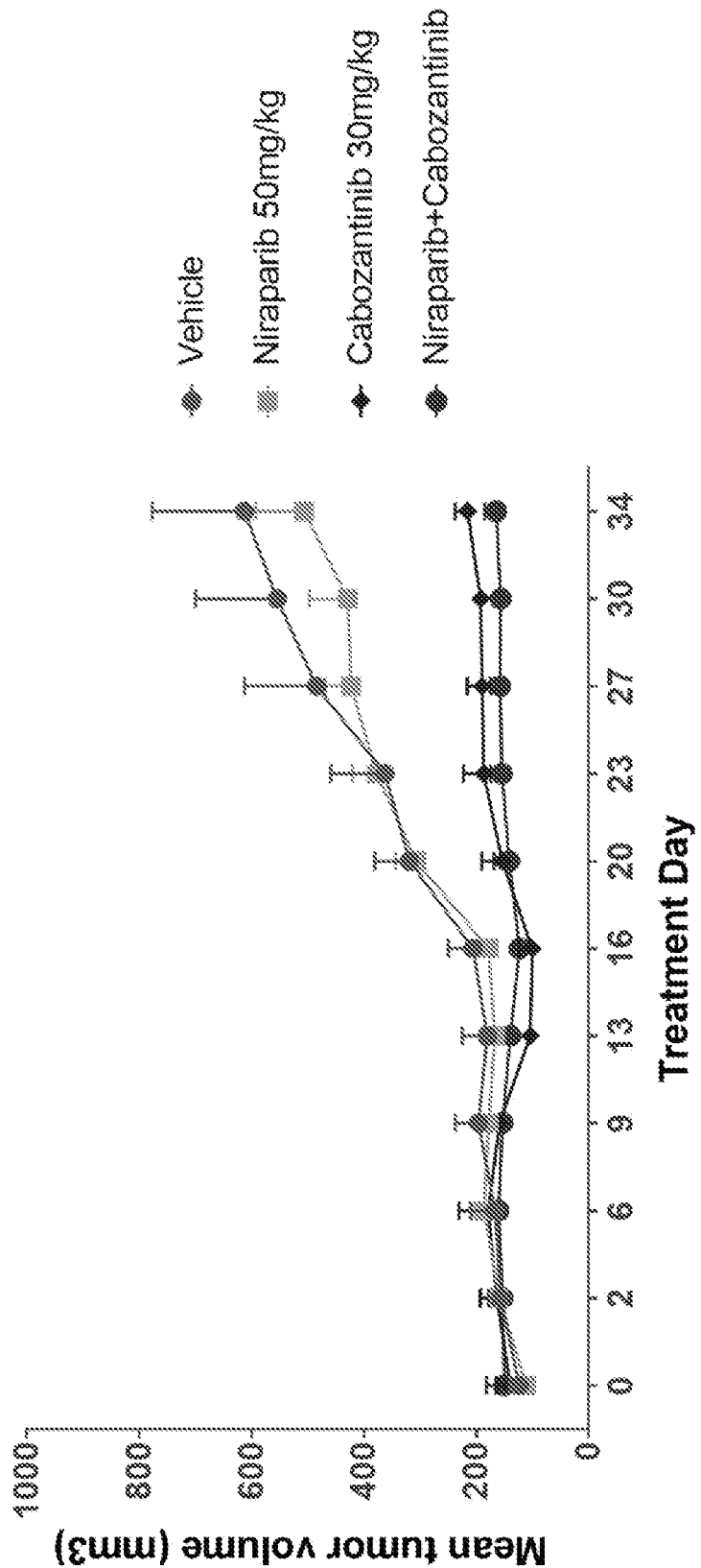
FIG. 7B depicts an exemplary study of anti-tumor activity of niraparib and cabozantinib combination in TNBC PDX model MAXF 857.

As shown in FIGS. 7A and 7B, tumor bearing mice were randomized into 6 cohorts and treated with vehicle, niraparib, bevacizumab, niraparib+bevacizumab, cabozantinib, niraparib+cabozantinib for 5 weeks. Tumor size and body weight were measured twice weekly. Niraparib+bevacizumab combination and niraparib+cabozantinib combination are presented in 2 separated grafts for better viewing. This model is very sensitive to both bevacizumab and cabozantinib monotherapy, therefore no additional combination benefit could be observed for either niraparib+bevacizumab or niraparib+cabozantinib combination.

Example 9—Results of Anti-Tumor Activity of Niraparib+Bevacizumab Combination and Niraparib+Cabozantinib Combination in TNBC PDX Model MAXF MX1

Figure 8A:
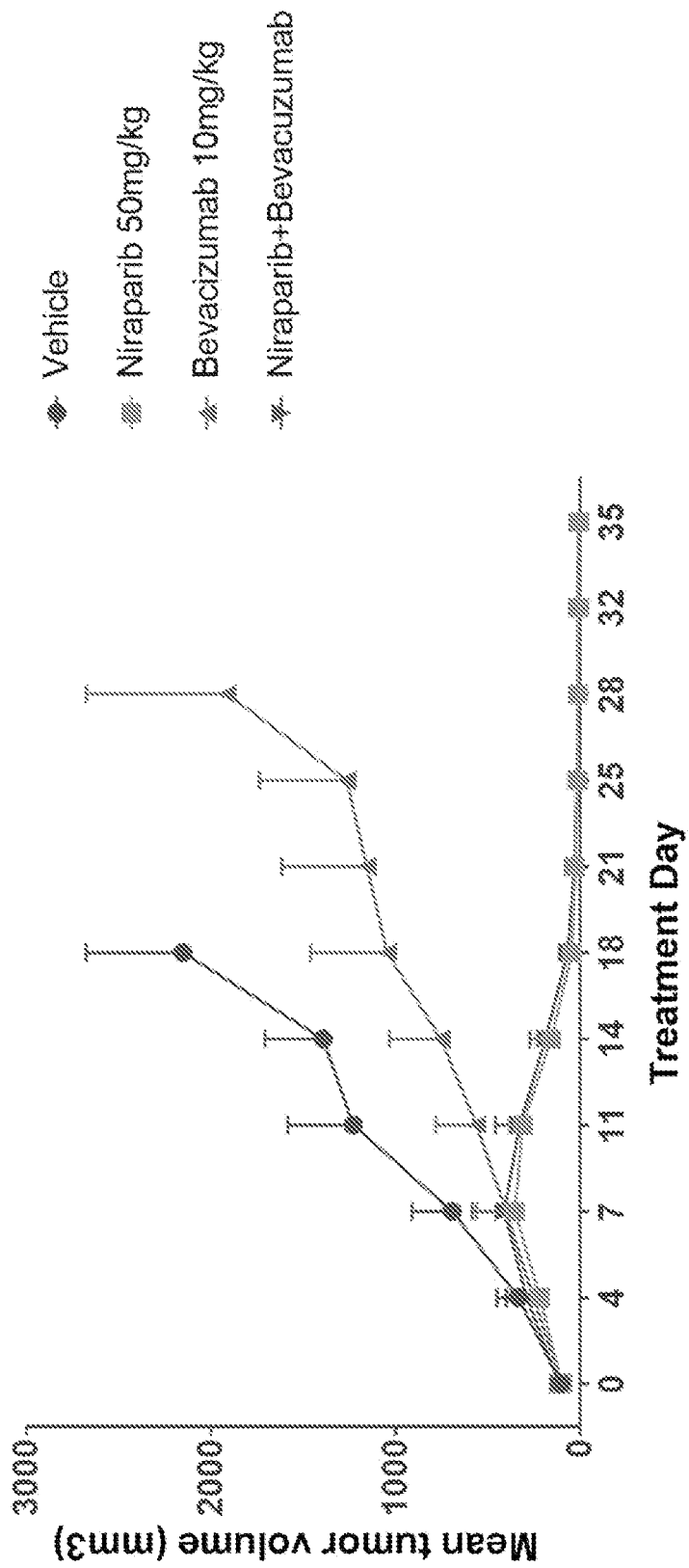
FIG. 8A depicts an exemplary study of anti-tumor activity of niraparib and bevacizumab combination in TNBC PDX model MAXF MX1.
Figure 8B:
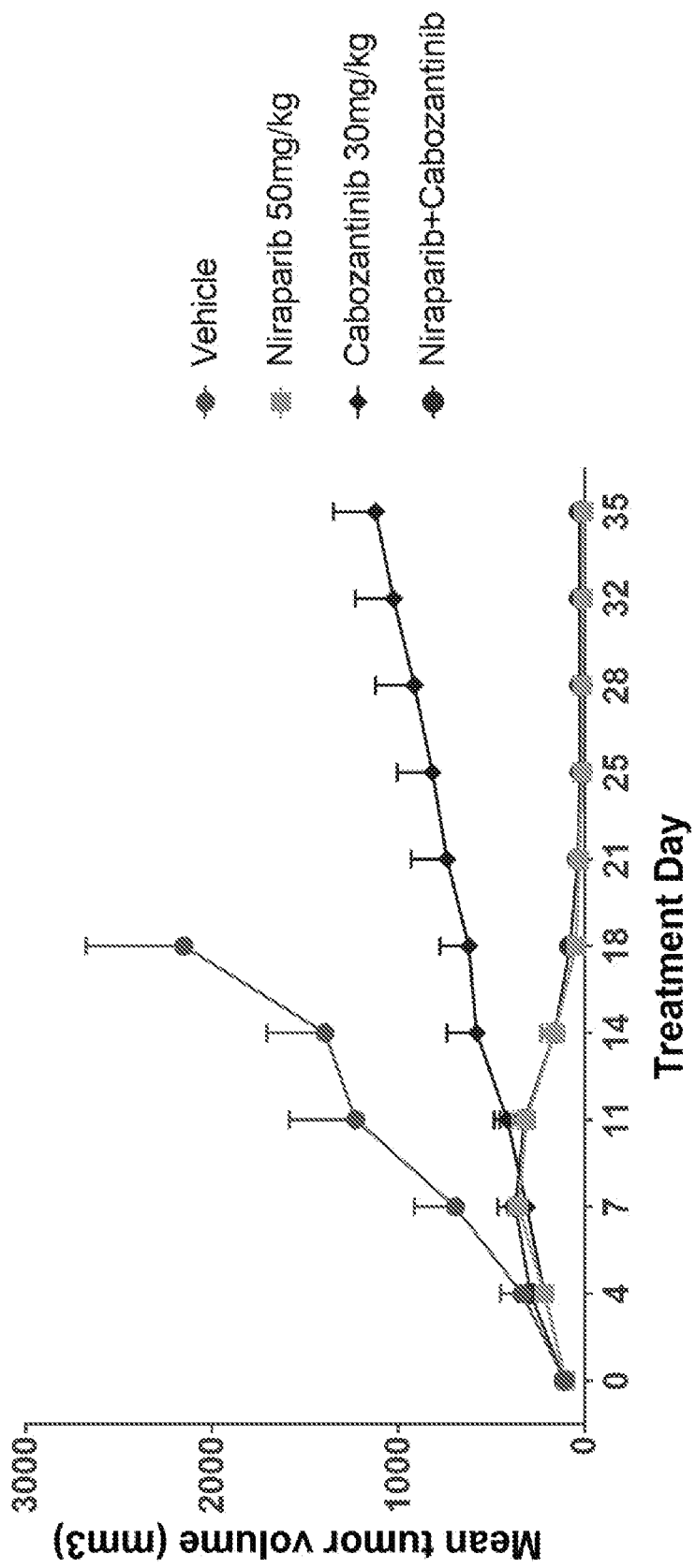
FIG. 8B depicts an exemplary study of anti-tumor activity of niraparib and cabozantinib combination in TNBC PDX model MAXF MX1.

As shown in FIGS. 8A and 8B, TNBC model MAXF MX1 tumor bearing mice were randomized into 6 cohorts and treated with vehicle, niraparib, bevacizumab, niraparib+bevacizumab, cabozantinib, niraparib+cabozantinib for 5 weeks. Tumor size and body weight were measured twice weekly. This model is very sensitive to niraparib monotherapy, therefore no further combination benefit could be observed for either niraparib+bevacizumab or niraparib+cabozantinib.

While various embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating cancer in a human in need thereof comprising administering to the human a therapeutically effective amount of:
   (a) a first agent that is niraparib or a pharmaceutically acceptable salt thereof; and
   (b) a second agent that is an angiogenesis inhibitor;
   wherein the cancer is selected from the group consisting of carcinoma, squamous carcinoma, adenocarcinoma, sarcomata, endometrial cancer, breast cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, and neuroma.

2. The method of claim 1, wherein the angiogenesis inhibitor is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; or a toxin.

3. The method of claim 1, wherein the angiogenesis inhibitor is selected from the group consisting of bevacizumab, itraconazole, carboxyamidotriazole, TNP-470, fumagillin, CM101, IL-12, platelet factor-4, suramin, SU5416, thrombospondin, angiostatic steroids, heparin, cartilage-derived angiogenesis inhibitory factor, matrix metalloproteinase inhibitor, angiostatin, endostatin, 2-methoxyestradiol, tecogalan, tetrathiomolybdate, thrombospondin, thalidomide, prolactin, $\alpha V\beta 3$ inhibitor, lenalidomide, linomide, ramucirumab, tasquinimod, ranibizumab, sorafenib, sunitinib, pazopanib, everolimus, tissue inhibitors of metalloproteases (TIMP1 and TIMP2), bFGF soluble receptor, transforming growth factor beta, interferon alpha, soluble KDR and FLT-1 receptors, placental proliferin-related protein, pazopanib, sunitinib, sorafenib, axitinib, ponatinib, cabozantinib, regorafenib, vandetanib, lenvatinib, semaxanib, SU6668, vatalanib, tivozanib, cediranib, protamine, heparin, steroids, ascorbic acid ethers, sulfated polysaccharide DS 4152, fumagillin, AGM 12470, neovastat, RO4929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, OMP-21M18, navicixizumab (OMP-305B83), $Flt_{2-11}$, CBO-P11, Je-11, and V1.

4. The method of claim 1, wherein the angiogenesis inhibitor inhibits a vascular endothelial growth factor (VEGF) and/or vascular endothelial growth factor receptor (VEGFR) pathway.

5. The method of claim 4, wherein the angiogenesis inhibitor is selected from the group consisting of Akt inhibitor, calcineurin autoinhibitory peptide, ET-18-OCH3, Go 6983, $N^G$-Nitro-L-arginine methyl ester, p21-activated kinase Inhibitor, cPLA2α inhibitor, PI-103, PP2, SB 203580, U0126, VEGFR tyrosine kinase inhibitor V, VEGFR2 kinase inhibitor VI, VEGFR2 kinase inhibitor III, or ZM 336372.

6. The method of claim 4, wherein the angiogenesis inhibitor is a VEGF inhibitor which is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; or a toxin.

7. The method of claim 6, wherein the VEGF inhibitor is an antibody or a fragment thereof.

8. The method of claim 7, wherein the VEGF inhibitor is bevacizumab, ranibizumab, OPT-302, or ziv-aflibercept.

9. The method of claim 4, wherein the angiogenesis inhibitor is a VEGFR inhibitor which is a tyrosine kinase inhibitor.

10. The method of claim 9, wherein the tyrosine kinase inhibitor is pazopanib, sunitinib, sorafenib, axitinib, ponatinib, cabozantinib, regorafenib, vandetanib, lenvatinib, semaxanib, SU6668, vatalanib, tivozanib, or cediranib.

11. The method of claim 4, wherein the angiogenesis inhibitor is a VEGFR inhibitor which is ramucirumab.

12. The method of claim 1, wherein the first agent is niraparib, and the second agent is bevacizumab.

13. The method of claim 1, wherein the cancer is breast cancer.

14. The method of claim 13, wherein the breast cancer is triple negative breast cancer.

15. The method of claim 1, wherein the poly[ADP-ribose] polymerase inhibitor is in the form of a pharmaceutical composition.

16. The method of claim 15, wherein the composition is a capsule.

17. The method of claim 15, wherein the composition is a tablet.

18. The method of claim 1, wherein the human has previously been treated with one or more different cancer treatment modalities.

19. The method of claim 18, wherein the subject has previously been treated with one or more of radiotherapy, chemotherapy, or immunotherapy.

20. The method of claim 18, wherein the subject has been treated with one, two, three, four, or five lines of prior therapy.

21. The method of claim 1, further comprising administering a therapeutically effect amount of another agent or further treating the human with surgery or radiotherapy.

22. The method of claim 21, wherein the third agent comprises a radiotherapeutic agent, an anti-immunosuppressive agent or immunostimulatory agent, or a chemotherapeutic agent.

23. The method of claim 22, wherein the anti-immunosuppressive agent or immunostimulatory agent comprises an anti-PD-1 agent, an anti-PD-L1 agent, an anti-CTLA4 agent, an anti-TIM-3 agent, an anti-LAG-3 agent, a GITR (glucocorticoid-induced TNFR-related protein) stimulating agent, an anti-IDO agent, an anti-ICOS agent, an anti-OX40 agent, an anti-CSF1R agent, a chemokine signaling agent, or a cytokine signal stimulating agent.

24. The method of claim 23, wherein the anti-PD-1 agent is selected from the group consisting of pembrolizumab, nivolumab, PDR001, REGN2810 (SAR-439684), BGB-A317, BI 754091, IBI308, INCSHR-1210, JNJ-63723283, JS-001, MEDI0680 (AMP-514), MGA-012, PF-06801591, REGN-2810, TSR-042, atezolizumab, avelumab, CX-072, durvalumab, FAZ053, LY3300054, and PD-L1 millamolecule.

25. The method of claim 23, wherein the anti-PD-L1 agent is selected from the group consisting of atezolizumab, durvalumab, avelumab, and LY3300054.

26. The method of claim 22, wherein the third agent is a chemotherapeutic agent selected from the group consisting of aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

27. The method of claim 8, wherein the VEGF inhibitor is bevacizumab.

28. A method of treating cancer in a human in need thereof comprising administering to the human a therapeutically effective amount of:
(a) 2-{4-[(3S)-piperidin-3-yl]phenyl}-2H-indazole-7-carboxamide or a pharmaceutically acceptable salt thereof; and
(b) VEGF inhibitor;
wherein the cancer is selected from the group consisting of carcinoma, squamous carcinoma, adenocarcinoma, sarcomata, endometrial cancer, breast cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, and neuroma.

29. The method of claim 28, wherein the VEGF inhibitor is bevacizumab.

30. A method of treating cancer in a human in need thereof comprising administering to the human a therapeutically effective amount of:
(a) 2-{4-[(3S)-piperidin-3-yl]phenyl}-2H-indazole-7-carboxamide 4-methylbenzenesulfonate monohydrate or a pharmaceutically acceptable salt thereof; and
(b) VEGF inhibitor;
wherein the cancer is selected from the group consisting of carcinoma, squamous carcinoma, adenocarcinoma, sarcomata, endometrial cancer, breast cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, and neuroma.

31. The method of claim 30, wherein the VEGF inhibitor is bevacizumab.

* * * * *

UNITED STATES PATENT AND TRADEMARK OFFICE
CERTIFICATE OF CORRECTION

| | | |
|---|---|---|
| PATENT NO. | : 11,801,240 B2 | Page 1 of 1 |
| APPLICATION NO. | : 16/754083 | |
| DATED | : October 31, 2023 | |
| INVENTOR(S) | : Keith W. Mikule, Zebin Wang and Yinghui Zhou | |

It is certified that error appears in the above-identified patent and that said Letters Patent is hereby corrected as shown below:

In the Claims

Claim 2, Column 48, Line 3, delete "fragment," and insert -- fragment; --

Claim 6, Column 48, Line 49, delete "fragment," and insert -- fragment; --

Claim 16, Column 49, Line 8, before "composition" insert -- pharmaceutical --

Claim 17, Column 49, Line 10, before "composition" insert -- pharmaceutical --

Claim 21, Column 49, Line 22, delete "effect" and insert -- effective --

Claim 26, Column 49, Line 50-51, delete "campothecin" and insert -- camptothecin --

Claim 26, Column 49, Line 55, delete "estramnustine" and insert -- estramustine --

Claim 26, Column 49, Line 59, delete "ironotecan"

Claim 30, Column 50, Line 39-40, delete "carboxamide 4-" and insert -- carboxamide-4- --

Signed and Sealed this
Twenty-third Day of January, 2024

Katherine Kelly Vidal
*Director of the United States Patent and Trademark Office*